(12) United States Patent
Zussman et al.

(10) Patent No.: US 9,464,368 B2
(45) Date of Patent: *Oct. 11, 2016

(54) METHODS OF ATTACHING A MOLECULE-OF-INTEREST TO A MICROTUBE

(75) Inventors: Eyal Zussman, Haifa (IL); Yael Dror, Misgav (IL); Jonathan Charles Kuhn, Haifa (IL)

(73) Assignee: TECHNION RESEARCH & DEVELOPMENT FOUNDATION LTD., Haifa (IL)

( * ) Notice: Subject to any disclaimer, the term of this patent is extended or adjusted under 35 U.S.C. 154(b) by 2 days.

This patent is subject to a terminal disclaimer.

(21) Appl. No.: 12/918,372

(22) PCT Filed: Feb. 12, 2009

(86) PCT No.: PCT/IL2009/000171
§ 371 (c)(1),
(2), (4) Date: Dec. 16, 2010

(87) PCT Pub. No.: WO2009/104176
PCT Pub. Date: Aug. 27, 2009

(65) Prior Publication Data
US 2011/0081394 A1  Apr. 7, 2011

Related U.S. Application Data

(60) Provisional application No. 61/064,206, filed on Feb. 21, 2008, provisional application No. 61/064,210, filed on Feb. 21, 2008, provisional application No. 61/064,204, filed on Feb. 21, 2008.

(51) Int. Cl.
*D01D 5/24* (2006.01)
*D01F 1/08* (2006.01)
(Continued)

(52) U.S. Cl.
CPC ............. *D01D 5/003* (2013.01); *A61K 9/0092* (2013.01); *B82Y 30/00* (2013.01); *C02F 3/102* (2013.01);
(Continued)

(58) Field of Classification Search
CPC ........ A61K 9/0092; A61K 9/00; A61K 9/48; A61K 9/50; A61K 9/4816; A61K 9/5005; D01D 5/003; D01D 5/007
See application file for complete search history.

(56) References Cited

U.S. PATENT DOCUMENTS 4,921,475 A  5/1990  Sibalis
5,209,734 A  5/1993  Hurley et al.
(Continued)

FOREIGN PATENT DOCUMENTS

AU  2007303821  4/2008
CN  1799649  7/2006
(Continued)

OTHER PUBLICATIONS

Zhang et al. Biomimetic and bioactive nanofibrous scaffolds from electrospun composite nanofibers. International Journal of Nanomedicine 2007, vol. 2, No. 4, pp. 623-638.*
(Continued)

*Primary Examiner* — Shafiqul Haq
(74) *Attorney, Agent, or Firm* — The Roy Gross Law Firm, LLC; Roy Gross

(57) ABSTRACT

Provided is a method of attaching a molecule-of-interest to a microtube, by co-electrospinning two polymeric solutions through co-axial capillaries, wherein a first polymeric solution of the two polymeric solutions is for forming a shell of the microtube and a second polymeric solution of the two polymeric solutions is for forming a coat over an internal surface of the shell, the first polymeric solution is selected solidifying faster than the second polymeric solution and a solvent of the second polymeric solution is selected incapable of dissolving the first polymeric solution and wherein the second polymeric solution comprises the molecule-of-interest, thereby attaching the molecule-of-interest to the microtube. Also provided is an electrospun microtube comprising an electrospun shell, an electrospun coat over an internal surface of the shell and a molecule-of-interest attached to the microtube.

18 Claims, 12 Drawing Sheets
(6 of 12 Drawing Sheet(s) Filed in Color)

(51) Int. Cl.

| | |
|---|---|
| *A61K 9/00* | (2006.01) |
| *D01D 5/00* | (2006.01) |
| *B82Y 30/00* | (2011.01) |
| *C02F 3/10* | (2006.01) |
| *C02F 3/34* | (2006.01) |
| *D01D 5/247* | (2006.01) |
| *D01F 1/10* | (2006.01) |
| *D01F 8/14* | (2006.01) |
| *G01N 33/543* | (2006.01) |
| *C02F 101/18* | (2006.01) |
| *C02F 101/20* | (2006.01) |
| *C02F 101/30* | (2006.01) |
| *C02F 101/36* | (2006.01) |

(52) U.S. Cl.
 CPC ............ *C02F 3/34* (2013.01); *C02F 3/342* (2013.01); *D01D 5/247* (2013.01); *D01F 1/10* (2013.01); *D01F 8/14* (2013.01); *G01N 33/54393* (2013.01); *C02F 2101/18* (2013.01); *C02F 2101/20* (2013.01); *C02F 2101/306* (2013.01); *C02F 2101/36* (2013.01); *C02F 2305/08* (2013.01); *Y02W 10/15* (2015.05); *Y10T 428/1393* (2015.01)

(56) References Cited

U.S. PATENT DOCUMENTS

| | | | |
|---|---|---|---|
| 5,688,501 | A | 11/1997 | Merril et al. |
| 5,795,340 | A | 8/1998 | Lang |
| 6,537,195 | B2 | 3/2003 | Forman |
| 6,537,241 | B1 | 3/2003 | Odland |
| 7,066,922 | B2 | 6/2006 | Angel et al. |
| 2001/0014394 | A1 | 8/2001 | Soane et al. |
| 2001/0034503 | A1 | 10/2001 | Mehier |
| 2003/0098518 | A1* | 5/2003 | Averdung et al. ............ 264/10 |
| 2003/0135158 | A1 | 7/2003 | Gonnelli |
| 2003/0139727 | A1 | 7/2003 | Angel et al. |
| 2004/0018226 | A1 | 1/2004 | Wnek et al. |
| 2004/0030377 | A1 | 2/2004 | Dubson et al. |
| 2004/0147903 | A1 | 7/2004 | Latini |
| 2004/0223954 | A1 | 11/2004 | Bruessow et al. |
| 2005/0180992 | A1 | 8/2005 | Belcher et al. |
| 2006/0119015 | A1 | 6/2006 | Wehrspohn et al. |
| 2006/0200232 | A1 | 9/2006 | Phaneuf et al. |
| 2006/0226580 | A1 | 10/2006 | Xia et al. |
| 2006/0228435 | A1 | 10/2006 | Andrady et al. |
| 2009/0061496 | A1 | 3/2009 | Kuhn et al. |
| 2010/0129656 | A1 | 5/2010 | Zussman et al. |
| 2010/0303881 | A1 | 12/2010 | Hoke et al. |
| 2011/0081394 | A1 | 4/2011 | Zussman et al. |

FOREIGN PATENT DOCUMENTS

| | | |
|---|---|---|
| EP | 2079860 | 7/2009 |
| WO | WO 03/000381 | 1/2003 |
| WO | WO 2006/019293 | 2/2006 |
| WO | WO 2006/108809 | 10/2006 |
| WO | WO 2008/041183 | 4/2008 |
| WO | WO 2009/104174 | 8/2009 |
| WO | WO 2009/104175 | 8/2009 |
| WO | WO 2009/104176 | 8/2009 |

OTHER PUBLICATIONS

Yarin et al. Material encapsulation and transport in core-shell micro/nanofibers, polymer and carbon nanotubes and micro/nanochannels. J. Mater. Chem., 2007, vol. 17, pp. 2585-2599.*
Kim et al. Controlled protein release from electrospun biodegradable fiber mesh composed of poly(e-caprolactone) and poly(ethylene oxide). International Journal of Pharmaceutics 2007, vol. 338, pp. 276-283.*
Official Action Dated Jun. 20, 2012 From the US Patent and Trademark Office Re. U.S. Appl. No. 12/918,377.
Official Action Dated Feb. 14, 2012 From the US Patent and Trademark Office Re. U.S. Appl. No. 12/311,601.
Response Dated Feb. 1, 2011 to Official Action of Oct. 1, 2010 From the US Patent and Trademark Office Re. U.S. Appl. No. 11/896,130.
Response Dated Mar. 24, 2011 to Office Action of Oct. 13, 2010 From the State Intellectual Property Office of the People's Republic of China Re. Application No. 200780044536.1.
Official Action Dated Apr. 7, 2011 From the US Patent and Trademark Office Re. U.S. Appl. No. 11/896,130.
Zussman et al. "Formation of Nanofiber Crossbar in Electrospinning", Applied Physics Letters, 82(6): 973-975, Feb. 10, 2003.
Response Dated Aug. 2, 2011 to Official Action of Apr. 7, 2011 From the US Patent and Trademark Office Re. U.S. Appl. No. 11/896,130.
Larsson et al. "Detection of Number and Viability of *E. coli* and A. Hydrophila With FISH Technique", Techneau, D.3.5.3, p. 1-30, Apr. 30, 2008.
International Preliminary Report on Patentability Dated Apr. 16, 2009 From the International Bureau of WIPO Re.: Application No. PCT/IB2007/054001.
International Search Report and the Written Opinion Dated Sep. 29, 2009 From the International Searching Authority Re.: Application No. PCT/IL2009/000169.
International Search Report and the Written Opinion Dated Sep. 29, 2009 From the International Searching Authority Re.: Application No. PCT/IL2009/000171.
International Search Report and the Written Opinion Dated Sep. 30, 2009 From the International Searching Authority Re.: Application No. PCT/IL2009/000170.
International Search Report Dated Oct. 14, 2008 From the International Searching Authority Re.: Appliation No. PCT/IB2007/054001.
Written Opinion Dated Oct. 14, 2008 From the International Searching Authority Re.: Application No. PCT/IB2007/054001.
Bognitzki et al. "Polymer, Metal, and Hybrid Nano- and Mesotubes by Coating Degradable Polymer Template Fibers (TUFT Process)", Advanced Materials, 12(9): 637-640, 2000.
Caruso et al. "Titanium Dioxide Tubes From Sol-Gel Coating of Electrospun Polymer Fibers", Advanced Materials, 13: 1577-1579, Oct. 16, 2001.
Dror et al. "One-Step Production of Polymeric Microtubes by Co-Electrospinning", Small, XP002497054, 3(6): 1064-1073, Jun. 4, 2007.
Dror et al. "Viable Encapsulation of Enzymes in Biodegradable Tubular Structures", Faculty of Mechanical Engineering, Faculty of Biology, Technion, Israel Institute of Technology, Haifa, IL, 18 P.
Huang et al. "Encapsulating Drugs in Biodegradable Ultrafine Fibers Through Co-Axial Electrospinning", Journal of Biomedical Materials Research, Part A, 77A: 169-179, 169, 2006.
Jiang et al. "A Facile Technique to Prepare Biodegradable Coaxial Electrospun Nanofibers for Controlled Release of Bioactive Agents", Journal of Controlled Release, XP005163067, 108(2-3): 237-243, Nov. 28, 2005.
Jiang et al. "Modulation of Protein Release From Biodegradable Core-Shell Structured Fibers Prepared by Coaxial Electrospinning", Journal of Biomedical Materials Research Part B: Applied Biomaterials, 79B: 50-57, 2006.
Li et al. "Direct Fabrication of Composite and Ceramic Hollow Nanofibers by Electrospinning", Nano Letters, 4(5): 933-938, 2004.
Li et al. "Electrospinning of Nanofibers: Reinventing the Wheel?", Advanced Materials, 16(14): 1151-1170, Jul. 19, 2004.
Li et al. "Electrospinning: A Simple and Versatile Technique for Producing Ceramic Nanofibers and Nanotubes", Journal of the American Ceramic Society, 89(6): 1861-1869, 2006.
Li et al. "Use of Electrospinning to Directly Fabricate Hollow Nanofibers With Functionalized Inner and Outer Surfaces", Small, XP002497053, 1(1): 83-86, Jan. 1, 2005.
Loscertales et al. "Electrically Forced Coaxial Nanojets for One-Step Hollow Nanofiber Design", Journal of the American Chemical Society, JACS, 126: 5376-5377, 2004.

(56) References Cited

OTHER PUBLICATIONS

Loscertales et al. "Micro/Nano Encapsulation Via Electrified Coaxial Liquid Jets", Science, 295: 1695-1698, Mar. 16, 2002.
Reneker et al. "Electrospinning of Nanofibers From Polymer Solutions and Melts", Advances in Applied Mechanics, 41: 1-3, 103-115, 142-153, 2006.
Reznik et al. "Evolution of A Compound Droplet Attached to a Core-Shell Nozzle Under the Action of a Strong Electric Field", Physics of Fluids, 18: 062101-1 -062101-13, 2006.
Salalha et al. "Encapsulation of Bacteria and Viruses in Electrospun Nanofibres", Nanotechnology, 17: 4675-4681, 2006.
Sun et al. "Compound Core-Shell Polymer Nanofibers by Co-Electrospinning", Advanced Materials, XP002497055, 15(22): 1929-1932, Nov. 17, 2003.
Xie et al. "Ultra-High Surface Fibrous Membranes From Electrospinning of Natural Proteins: Casein and Lipase Enzyme", Journal of Materials Science, 38: 2125-2133, 2003.
Yarin et al. "Material Encapsulation and Transport in Core-Shell Micro/Naonofibers, Polymer and Carbon Nanotubes and Micro/Nanochannels", Journal of Materials Chemistry, XP002546457, 17(25): 2585-2599, Jul. 1, 2007. Chapter III Section (ii).
Yu et al. "Production of Submicrometer Diameter Fibers by Two-Fluid Electrospinning", Advanced Materials, 16(17): 1562-1566, Sep. 3, 2004.
Zhang et al. "Coaxial Electrospinning of (Fluorescein Isothiocyanate-Conjugated Bovine Serum Albumin)-Encapsulated Poly($\epsilon$-Caprolactone) Nanofibers for Sustained Release", Biomacromolecules, 7(4): 1049-1057, 2006.
Zussman et al. "Electrospun Polyacrylonitrile/Poly(Methyl Methacrylate)-Derived Turbostratic Carbon Micro-/Nanotubes", Advanced Materials, 18: 348-353, 2006.
Official Action Dated Nov. 3, 2011 From the US Patent and Trademark Office Re. U.S. Appl. No. 11/896,130.
Communication Pursuant to Article 94(3) EPC Dated Dec. 2, 2011 From the European Patent Office Re. Application No. 07826621.0.
Restriction Official Action Dated Dec. 23, 2011 From the US Patent and Trademark Office Re. U.S. Appl. No. 12/311,601.
Official Action Dated Oct. 1, 2010 From the US Patent and Trademark Office Re. U.S. Appl. No. 11/896,130.
Lee et al. "Virus-Based Fabrication of Micro- and Nanofibers Using Electrospinning", NanoLetters, 4(3): 387-390, 2004.
Salalha et al. "Encapsulation of Bacteria and Viruses in Electrospun Nanofibres", Nanotechnology, 17: 4675-4681, Aug. 30, 2006.
Theron et al. "Electrostatic Field-Assisted Alignment of Electrospun Nanofibres", Nanotechnology, 12: 384-390, 2001.
Interantional Preliminary Report on Patentability Dated Sep. 2, 2010 From the International Bureau of WIPO Re. Application No. PCT/IL2009/000171.
Translation of Office Action Dated Oct. 13, 2010 From the State Intellectual Property Office of the People's Republic of China Re. Application No. 200780044536.1.
He et al. "Recent Development of the Nanocomposites Prepared by Coaxial Jet Technology", Acta Materiae Compositae Sinica, 22(6): 1-8, Dec. 2005. Abstract in English.
Li et al. "Porous Ultrafine Nanofibers Having a Ultrahigh Specific Surface Area", Chinese Science Bulletin, 49(21): 2160-2163, Nov. 2004. Chinese Only!
International Preliminary Report on Patentability Dated Sep. 2, 2010 From the International Bureau of WIPO Re. Application No. PCT/IL2009/000171.
International Preliminary Report on Patentability Dated Sep. 2, 2010 From the International Bureau of WIPO Re.: Application No. PCT/IL2009/000169.
International Preliminary Report on Patentability Dated Sep. 2, 2010 From the International Bureau of WIPO Re.: Application No. PCT/IL2009/0001790.

Translation of Office Action Dated Mar. 1, 2012 From the State Intellectual Property Office of the People's Republic of China Re. Application No. 200780044536.1.
Communication Pursuant to Article 94(3) EPC Dated Jul. 18, 2012 From the European Patent Office Re. Application No. 09713280.7.
Communication Pursuant to Article 94(3) EPC Dated Jul. 19, 2012 From the European Patent Office Re. Application No. 09712148.7.
Communication Pursuant to Article 94(3) EPC Dated Jul. 19, 2012 From the European Patent Office Re. Application No. 09713264.1.
Official Action Dated Aug. 27, 2012 From the US Patent and Trademark Office Re. U.S. Appl. No. 12/311,601.
Official Action Dated Feb. 7, 2013 From the US Patent and Trademark Office Re. U.S. Appl. No. 12/311,601.
Translation of Office Action Dated Dec. 4, 2012 From the State Intellectual Property Office of the People's Republic of China Re. Application No. 200780044536.1.
Patent Examination Report Dated Nov. 19, 2012 From the Australian Government, IP Australia Re. Application No. 2007303821.
Official Action Dated Jun. 18, 2013 From the US Patent and Trademark Office Re. U.S. Appl. No. 12/918,365.
Advisory Action Before the Filing of an Appeal Brief Dated May 16, 2013 From the US Patent and Trademark Office Re. U.S. Appl. No. 12/311,601.
Restriction Official Action Dated May 9, 2012 From the US Patent and Trademark Office Re. U.S. Appl. No. 12/918,365.
Restriction Official Action Dated Mar. 1, 2013 From the US Patent and Trademark Office Re. U.S. Appl. No. 12/918,365.
Advisory Action Before the Filing of an Appeal Brief Dated Apr. 12, 2013 From the US Patent and Trademark Office Re. U.S. Appl. No. 12/311,601.
Official Action Dated Apr. 8, 2013 From the US Patent and Trademark Office Re. U.S. Appl. No. 12/918,377.
Decision to Grant a European Patent Pursuant to Article 97(1) EPC Dated Jul. 11, 2013 From the European Patent Office Re. Application No. 07826621.0.
Translation of Office Action Dated Jun. 4, 2013 From the State Intellectual Property Office of the People's Republic of China Re. Application No. 200780044536.1.
Communication Under Rule 71(3) EPC Dated Mar. 5, 2013 From the European Patent Office Re. Application No. 07826621.0.
Communication Pursuant to Article 94(3) EPC Dated Aug. 20, 2013 From the European Patent Office Re. Application No. 09713264.1.
Advisory Action Before the Filing of an Appeal Brief Dated May 30, 2014 From the US Patent and Trademark Office Re. U.S Appl. No. 12/918,365.
Requisition by the Examiner Dated May 22, 2014 From the Canadian Intellectual Property Office Re. Application No. 2,664,972.
Official Action Dated Oct. 1, 2014 From the US Patent and Trademark Office Re. U.S. Appl. No. 11/896,130.
Office Action Dated Nov. 21, 2013 From the State Intellectual Property Office of the People's Republic of China Re. Application No. 200780044536.1 and Its Translation Into English.
Official Action Dated Jan. 17, 2014 From the US Patent and Trademark Office Re. U.S. Appl. No. 12/918,365.
Official Action Dated Jan. 9, 2015 From the US Patent and Trademark Office Re. U.S. Appl. No. 12/918,377.
Official Action Dated Jan. 14, 2015 From the US Patent and Trademark Office Re. U.S. Appl. No. 12/311,601.
McCann et al. "Electrospinning of Nanofibers With Core-Sheath, Hollow, or Porous Structures", Journal of Materials Chemistry, 15: 735-738, 2005.
Communication Pursuant to Article 94(3) EPC Dated Aug. 23, 2013 From the European Patent Office Re. Application No. 09713280.7.
Official Action Dated Feb. 4, 2015 From the US Patent and Trademark Office Re. U.S. Appl. No. 12/918,365.
Requisition by the Examiner and Examination Search Report Dated Jan. 23, 2015 From the Canadian Intellectual Property Office Re. Application No. 2,664,972.

* cited by examiner

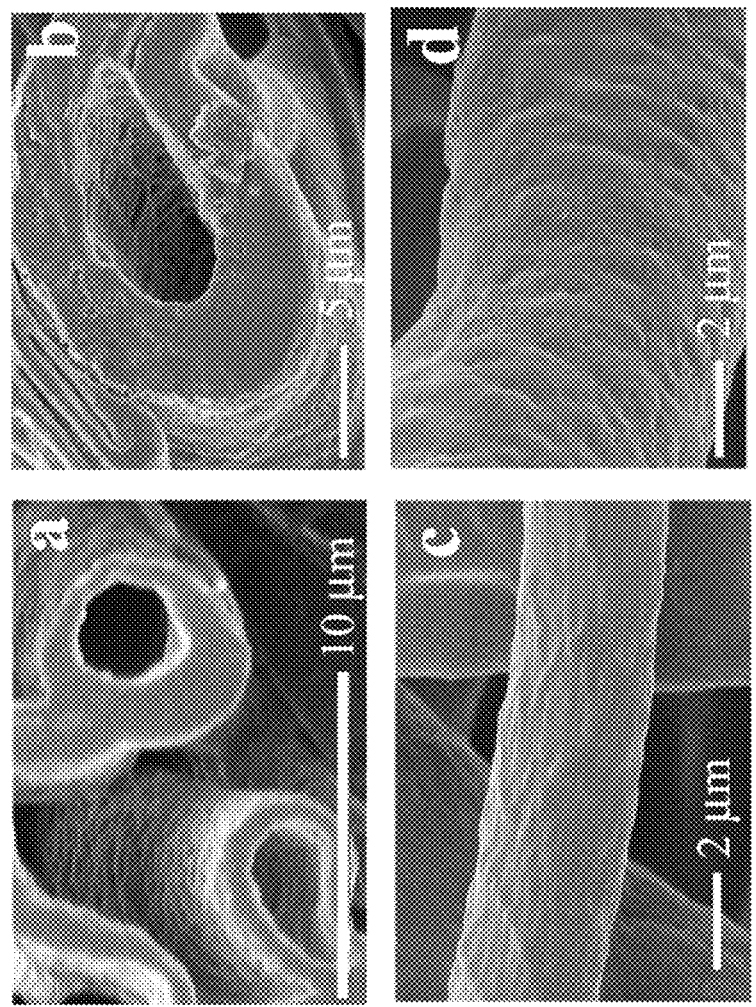
FIGs. 1A-D

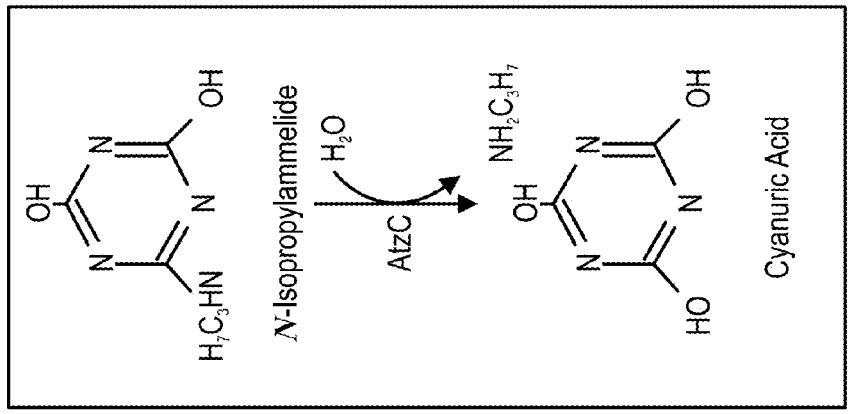
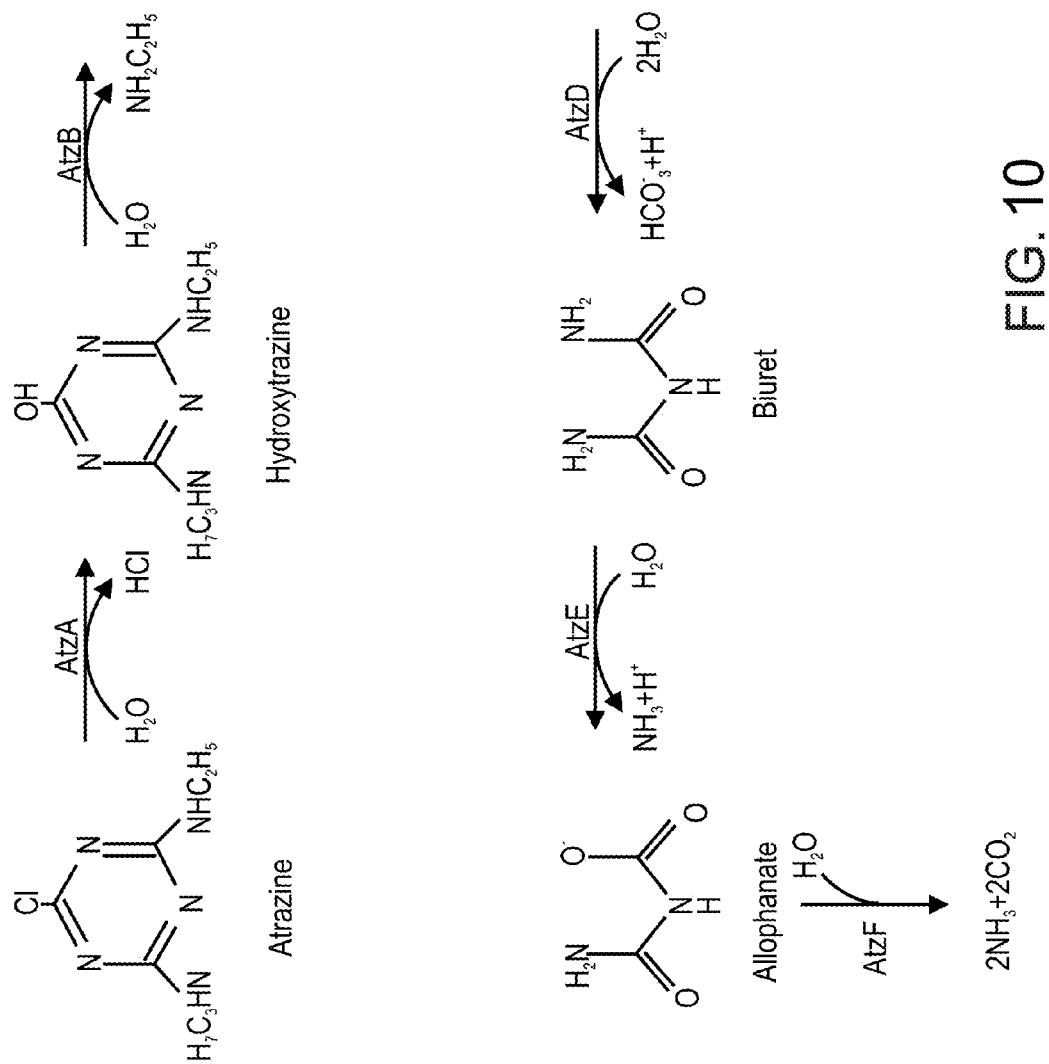
FIG. 10

SEQUENCE LISTING

```
<160> NUMBER OF SEQ ID NOS: 9

<210> SEQ ID NO 1
<211> LENGTH: 524
<212> TYPE: PRT
<213> ORGANISM: Homo sapiens

<400> SEQUENCE: 1

Met Ile Ser Pro Phe Leu Val Leu Ala Ile Gly Thr Cys Leu Thr Asn
1               5                   10                  15
```

```
Ser Leu Val Pro Glu Lys Glu Lys Asp Pro Lys Tyr Trp Arg Asp Gln
             20                  25                  30

Ala Gln Glu Thr Leu Lys Tyr Ala Leu Glu Leu Gln Lys Leu Asn Thr
         35                  40                  45

Asn Val Ala Lys Asn Val Ile Met Phe Leu Gly Asp Gly Met Gly Val
     50                  55                  60

Ser Thr Val Thr Ala Ala Arg Ile Leu Lys Gly Gln Leu His His Asn
 65                  70                  75                  80

Pro Gly Glu Glu Thr Arg Leu Glu Met Asp Lys Phe Pro Phe Val Ala
                 85                  90                  95

Leu Ser Lys Thr Tyr Asn Thr Asn Ala Gln Val Pro Ser Ala Gly
             100                 105                 110

Thr Ala Thr Ala Tyr Leu Cys Gly Val Lys Ala Asn Glu Gly Thr Val
         115                 120                 125

Gly Val Ser Ala Ala Thr Glu Arg Ser Arg Cys Asn Thr Thr Gln Gly
     130                 135                 140

Asn Glu Val Thr Ser Ile Leu Arg Trp Ala Lys Asp Ala Gly Lys Ser
145                 150                 155                 160

Val Gly Ile Val Thr Thr Thr Arg Val Asn His Ala Thr Pro Ser Ala
                 165                 170                 175

Ala Tyr Ala His Ser Ala Asp Arg Asp Trp Tyr Ser Asp Asn Glu Met
             180                 185                 190

Pro Pro Glu Ala Leu Ser Gln Gly Cys Lys Asp Ile Ala Tyr Gln Leu
         195                 200                 205

Met His Asn Ile Arg Asp Ile Asp Val Ile Met Gly Gly Gly Arg Lys
     210                 215                 220

Tyr Met Tyr Pro Lys Asn Lys Thr Asp Val Glu Tyr Glu Ser Asp Glu
225                 230                 235                 240

Lys Ala Arg Gly Thr Arg Leu Asp Gly Leu Asp Leu Val Asp Thr Trp
                 245                 250                 255

Lys Ser Phe Lys Pro Arg Tyr Lys His Ser His Phe Ile Trp Asn Arg
             260                 265                 270

Thr Glu Leu Leu Thr Leu Asp Pro His Asn Val Asp Tyr Leu Leu Gly
         275                 280                 285

Leu Phe Glu Pro Gly Asp Met Gln Tyr Glu Leu Asn Arg Asn Asn Val
     290                 295                 300

Thr Asp Pro Ser Leu Ser Glu Met Val Val Ala Ile Gln Ile Leu
305                 310                 315                 320

Arg Lys Asn Pro Lys Gly Phe Phe Leu Leu Val Glu Gly Gly Arg Ile
                 325                 330                 335

Asp His Gly His His Glu Gly Lys Ala Lys Gln Ala Leu His Glu Ala
             340                 345                 350

Val Glu Met Asp Arg Ala Ile Gly Gln Ala Gly Ser Leu Thr Ser Ser
         355                 360                 365

Glu Asp Thr Leu Thr Val Val Thr Ala Asp His Ser His Val Phe Thr
     370                 375                 380

Phe Gly Gly Tyr Thr Pro Arg Gly Asn Ser Ile Phe Gly Leu Ala Pro
385                 390                 395                 400

Met Leu Ser Asp Thr Asp Lys Lys Pro Phe Thr Ala Ile Leu Tyr Gly
                 405                 410                 415

Asn Gly Pro Gly Tyr Lys Val Val Gly Gly Glu Arg Gly Asn Val Ser
             420                 425                 430
```

```
Met Val Asp Tyr Ala His Asn Asn Tyr Gln Ala Gln Ser Ala Val Pro
            435                 440                 445

Leu Arg His Glu Thr His Gly Gly Glu Asp Val Ala Val Phe Ser Lys
    450                 455                 460

Gly Pro Met Ala His Leu Leu His Gly Val His Glu Gln Asn Tyr Val
465                 470                 475                 480

Pro His Val Met Ala Tyr Ala Ala Cys Ile Gly Ala Asn Leu Gly His
                485                 490                 495

Cys Ala Pro Ala Ser Ser Ala Gly Ser Leu Ala Ala Gly Pro Leu Leu
                500                 505                 510

Leu Ala Leu Ala Leu Tyr Pro Leu Ser Val Leu Phe
        515                 520

<210> SEQ ID NO 2
<211> LENGTH: 1024
<212> TYPE: PRT
<213> ORGANISM: Homo sapiens

<400> SEQUENCE: 2

Met Thr Met Ile Thr Asp Ser Leu Ala Val Val Leu Gln Arg Arg Asp
1               5                   10                  15

Trp Glu Asn Pro Gly Val Thr Gln Leu Asn Arg Leu Ala Ala His Pro
            20                  25                  30

Pro Phe Ala Ser Trp Arg Asn Ser Glu Ala Arg Thr Asp Arg Pro
        35                  40                  45

Ser Gln Gln Leu Arg Ser Leu Asn Gly Glu Trp Arg Phe Ala Trp Phe
    50                  55                  60

Pro Ala Pro Glu Ala Val Pro Glu Ser Trp Leu Glu Cys Asp Leu Pro
65                  70                  75                  80

Glu Ala Asp Thr Val Val Pro Ser Asn Trp Gln Met His Gly Tyr
                85                  90                  95

Asp Ala Pro Ile Tyr Thr Asn Val Thr Tyr Pro Ile Thr Val Asn Pro
                100                 105                 110

Pro Phe Val Pro Thr Glu Asn Pro Thr Gly Cys Tyr Ser Leu Thr Phe
            115                 120                 125

Asn Val Asp Glu Ser Trp Leu Gln Glu Gly Gln Thr Arg Ile Ile Phe
    130                 135                 140

Asp Gly Val Asn Ser Ala Phe His Leu Trp Cys Asn Gly Arg Trp Val
145                 150                 155                 160

Gly Tyr Gly Gln Asp Ser Arg Leu Pro Ser Glu Phe Asp Leu Ser Ala
                165                 170                 175

Phe Leu Arg Ala Gly Glu Asn Arg Leu Ala Val Met Val Leu Arg Trp
                180                 185                 190

Ser Asp Gly Ser Tyr Leu Glu Asp Gln Asp Met Trp Arg Met Ser Gly
            195                 200                 205

Ile Phe Arg Asp Val Ser Leu Leu His Lys Pro Thr Thr Gln Ile Ser
    210                 215                 220

Asp Phe His Val Ala Thr Arg Phe Asn Asp Asp Phe Ser Arg Ala Val
225                 230                 235                 240

Leu Glu Ala Glu Val Gln Met Cys Gly Glu Leu Arg Asp Tyr Leu Arg
                245                 250                 255

Val Thr Val Ser Leu Trp Gln Gly Glu Thr Gln Val Ala Ser Gly Thr
                260                 265                 270

Ala Pro Phe Gly Gly Glu Ile Ile Asp Glu Arg Gly Gly Tyr Ala Asp
            275                 280                 285
```

```
Arg Val Thr Leu Arg Leu Asn Val Glu Asn Pro Lys Leu Trp Ser Ala
    290                 295                 300
Glu Ile Pro Asn Leu Tyr Arg Ala Val Val Glu Leu His Thr Ala Asp
305                 310                 315                 320
Gly Thr Leu Ile Glu Ala Glu Ala Cys Asp Val Gly Phe Arg Glu Val
                325                 330                 335
Arg Ile Glu Asn Gly Leu Leu Leu Leu Asn Gly Lys Pro Leu Leu Ile
                340                 345                 350
Arg Gly Val Asn Arg His Glu His His Pro Leu His Gly Gln Val Met
            355                 360                 365
Asp Glu Gln Thr Met Val Gln Asp Ile Leu Leu Met Lys Gln Asn Asn
370                 375                 380
Phe Asn Ala Val Arg Cys Ser His Tyr Pro Asn His Pro Leu Trp Tyr
385                 390                 395                 400
Thr Leu Cys Asp Arg Tyr Gly Leu Tyr Val Val Asp Glu Ala Asn Ile
                405                 410                 415
Glu Thr His Gly Met Val Pro Met Asn Arg Leu Thr Asp Asp Pro Arg
                420                 425                 430
Trp Leu Pro Ala Met Ser Glu Arg Val Thr Arg Met Val Gln Arg Asp
            435                 440                 445
Arg Asn His Pro Ser Val Ile Ile Trp Ser Leu Gly Asn Glu Ser Gly
450                 455                 460
His Gly Ala Asn His Asp Ala Leu Tyr Arg Trp Ile Lys Ser Val Asp
465                 470                 475                 480
Pro Ser Arg Pro Val Gln Tyr Glu Gly Gly Gly Ala Asp Thr Thr Ala
                485                 490                 495
Thr Asp Ile Ile Cys Pro Met Tyr Ala Arg Val Asp Glu Asp Gln Pro
                500                 505                 510
Phe Pro Ala Val Pro Lys Trp Ser Ile Lys Lys Trp Leu Ser Leu Pro
            515                 520                 525
Gly Glu Thr Arg Pro Leu Ile Leu Cys Glu Tyr Ala His Ala Met Gly
530                 535                 540
Asn Ser Leu Gly Gly Phe Ala Lys Tyr Trp Gln Ala Phe Arg Gln Tyr
545                 550                 555                 560
Pro Arg Leu Gln Gly Gly Phe Val Trp Asp Trp Val Asp Gln Ser Leu
                565                 570                 575
Ile Lys Tyr Asp Glu Asn Gly Asn Pro Trp Ser Ala Tyr Gly Gly Asp
                580                 585                 590
Phe Gly Asp Thr Pro Asn Asp Arg Gln Phe Cys Met Asn Gly Leu Val
            595                 600                 605
Phe Ala Asp Arg Thr Pro His Pro Ala Leu Thr Glu Ala Lys His Gln
610                 615                 620
Gln Gln Phe Phe Gln Phe Arg Leu Ser Gly Gln Thr Ile Glu Val Thr
625                 630                 635                 640
Ser Glu Tyr Leu Phe Arg His Ser Asp Asn Glu Leu Leu His Trp Met
                645                 650                 655
Val Ala Leu Asp Gly Lys Pro Leu Ala Ser Gly Glu Val Pro Leu Asp
                660                 665                 670
Val Ala Pro Gln Gly Lys Gln Leu Ile Glu Leu Pro Glu Leu Pro Gln
            675                 680                 685
Pro Glu Ser Ala Gly Gln Leu Trp Leu Thr Val Arg Val Val Gln Pro
690                 695                 700
```

```
Asn Ala Thr Ala Trp Ser Glu Ala Gly His Ile Ser Ala Trp Gln Gln
705                 710                 715                 720

Trp Arg Leu Ala Glu Asn Leu Ser Val Thr Leu Pro Ala Ala Ser His
                725                 730                 735

Ala Ile Pro His Leu Thr Thr Ser Glu Met Asp Phe Cys Ile Glu Leu
            740                 745                 750

Gly Asn Lys Arg Trp Gln Phe Asn Arg Gln Ser Gly Phe Leu Ser Gln
        755                 760                 765

Met Trp Ile Gly Asp Lys Lys Gln Leu Leu Thr Pro Leu Arg Asp Gln
770                 775                 780

Phe Thr Arg Ala Pro Leu Asp Asn Asp Ile Gly Val Ser Glu Ala Thr
785                 790                 795                 800

Arg Ile Asp Pro Asn Ala Trp Val Glu Arg Trp Lys Ala Ala Gly His
                805                 810                 815

Tyr Gln Ala Glu Ala Ala Leu Leu Gln Cys Thr Ala Asp Thr Leu Ala
            820                 825                 830

Asp Ala Val Leu Ile Thr Thr Ala His Ala Trp Gln His Gln Gly Lys
        835                 840                 845

Thr Leu Phe Ile Ser Arg Lys Thr Tyr Arg Ile Asp Gly Ser Gly Gln
850                 855                 860

Met Ala Ile Thr Val Asp Val Glu Val Ala Ser Asp Thr Pro His Pro
865                 870                 875                 880

Ala Arg Ile Gly Leu Asn Cys Gln Leu Ala Gln Val Ala Glu Arg Val
                885                 890                 895

Asn Trp Leu Gly Leu Gly Pro Gln Glu Asn Tyr Pro Asp Arg Leu Thr
            900                 905                 910

Ala Ala Cys Phe Asp Arg Trp Asp Leu Pro Leu Ser Asp Met Tyr Thr
        915                 920                 925

Pro Tyr Val Phe Pro Ser Glu Asn Gly Leu Arg Cys Gly Thr Arg Glu
930                 935                 940

Leu Asn Tyr Gly Pro His Gln Trp Arg Gly Asp Phe Gln Phe Asn Ile
945                 950                 955                 960

Ser Arg Tyr Ser Gln Gln Gln Leu Met Glu Thr Ser His Arg His Leu
                965                 970                 975

Leu His Ala Glu Glu Gly Thr Trp Leu Asn Ile Asp Gly Phe His Met
            980                 985                 990

Gly Ile Gly Gly Asp Asp Ser Trp  Ser Pro Ser Val Ser  Ala Glu Phe
        995                 1000                1005

Gln Leu Ser Ala Gly Arg Tyr  His Tyr Gln Leu Val  Trp Cys Gln
    1010                1015                1020

Lys

<210> SEQ ID NO 3
<211> LENGTH: 452
<212> TYPE: PRT
<213> ORGANISM: Homo sapiens

<400> SEQUENCE: 3

Met Ser Thr Ala Val Leu Glu Asn Pro Gly Leu Gly Arg Lys Leu Ser
1               5                   10                  15

Asp Phe Gly Gln Glu Thr Ser Tyr Ile Glu Asp Asn Cys Asn Gln Asn
                20                  25                  30

Gly Ala Ile Ser Leu Ile Phe Ser Leu Lys Glu Glu Val Gly Ala Leu
            35                  40                  45
```

```
Ala Lys Val Leu Arg Leu Phe Glu Glu Asn Asp Val Asn Leu Thr His
 50                  55                  60

Ile Glu Ser Arg Pro Ser Arg Leu Lys Lys Asp Glu Tyr Glu Phe Phe
 65                  70                  75                  80

Thr His Leu Asp Lys Arg Ser Leu Pro Ala Leu Thr Asn Ile Ile Lys
                 85                  90                  95

Ile Leu Arg His Asp Ile Gly Ala Thr Val His Glu Leu Ser Arg Asp
                100                 105                 110

Lys Lys Lys Asp Thr Val Pro Trp Phe Pro Arg Thr Ile Gln Glu Leu
            115                 120                 125

Asp Arg Phe Ala Asn Gln Ile Leu Ser Tyr Gly Ala Glu Leu Asp Ala
130                 135                 140

Asp His Pro Gly Phe Lys Asp Pro Val Tyr Arg Ala Arg Arg Lys Gln
145                 150                 155                 160

Phe Ala Asp Ile Ala Tyr Asn Tyr Arg His Gly Gln Pro Ile Pro Arg
                165                 170                 175

Val Glu Tyr Met Glu Glu Glu Lys Lys Thr Trp Gly Thr Val Phe Lys
            180                 185                 190

Thr Leu Lys Ser Leu Tyr Lys Thr His Ala Cys Tyr Glu Tyr Asn His
            195                 200                 205

Ile Phe Pro Leu Leu Glu Lys Tyr Cys Gly Phe His Glu Asp Asn Ile
210                 215                 220

Pro Gln Leu Glu Asp Val Ser Gln Phe Leu Gln Thr Cys Thr Gly Phe
225                 230                 235                 240

Arg Leu Arg Pro Val Ala Gly Leu Leu Ser Ser Arg Asp Phe Leu Gly
                245                 250                 255

Gly Leu Ala Phe Arg Val Phe His Cys Thr Gln Tyr Ile Arg His Gly
                260                 265                 270

Ser Lys Pro Met Tyr Thr Pro Glu Pro Asp Ile Cys His Glu Leu Leu
            275                 280                 285

Gly His Val Pro Leu Phe Ser Asp Arg Ser Phe Ala Gln Phe Ser Gln
            290                 295                 300

Glu Ile Gly Leu Ala Ser Leu Gly Ala Pro Asp Glu Tyr Ile Glu Lys
305                 310                 315                 320

Leu Ala Thr Ile Tyr Trp Phe Thr Val Glu Phe Gly Leu Cys Lys Gln
                325                 330                 335

Gly Asp Ser Ile Lys Ala Tyr Gly Ala Gly Leu Leu Ser Ser Phe Gly
                340                 345                 350

Glu Leu Gln Tyr Cys Leu Ser Glu Lys Pro Lys Leu Leu Pro Leu Glu
            355                 360                 365

Leu Glu Lys Thr Ala Ile Gln Asn Tyr Thr Val Thr Glu Phe Gln Pro
            370                 375                 380

Leu Tyr Tyr Val Ala Glu Ser Phe Asn Asp Ala Lys Glu Lys Val Arg
385                 390                 395                 400

Asn Phe Ala Ala Thr Ile Pro Arg Pro Phe Ser Val Arg Tyr Asp Pro
                405                 410                 415

Tyr Thr Gln Arg Ile Glu Val Leu Asp Asn Thr Gln Gln Leu Lys Ile
            420                 425                 430

Leu Ala Asp Ser Ile Asn Ser Glu Ile Gly Ile Leu Cys Ser Ala Leu
            435                 440                 445

Gln Lys Ile Lys
450
```

-continued

```
<210> SEQ ID NO 4
<211> LENGTH: 3677
<212> TYPE: PRT
<213> ORGANISM: Homo sapiens

<400> SEQUENCE: 4
```

Met Glu Asp Glu Arg Glu Asp Val Gln Lys Lys Thr Phe Thr Lys Trp
1               5                   10                  15

Val Asn Ala Gln Phe Ser Lys Phe Gly Lys Gln His Ile Glu Asn Leu
            20                  25                  30

Phe Ser Asp Leu Gln Asp Gly Arg Arg Leu Leu Asp Leu Leu Glu Gly
        35                  40                  45

Leu Thr Gly Gln Lys Leu Pro Lys Glu Lys Gly Ser Thr Arg Val His
    50                  55                  60

Ala Leu Asn Asn Val Asn Lys Ala Leu Arg Val Leu Gln Asn Asn Asn
65                  70                  75                  80

Val Asp Leu Val Asn Ile Gly Ser Thr Asp Ile Val Asp Gly Asn His
                85                  90                  95

Lys Leu Thr Leu Gly Leu Ile Trp Asn Ile Ile Leu His Trp Gln Val
            100                 105                 110

Lys Asn Val Met Lys Asn Ile Met Ala Gly Leu Gln Gln Thr Asn Ser
        115                 120                 125

Glu Lys Ile Leu Leu Ser Trp Val Arg Gln Ser Thr Arg Asn Tyr Pro
    130                 135                 140

Gln Val Asn Val Ile Asn Phe Thr Thr Ser Trp Ser Asp Gly Leu Ala
145                 150                 155                 160

Leu Asn Ala Leu Ile His Ser His Arg Pro Asp Leu Phe Asp Trp Asn
                165                 170                 175

Ser Val Val Cys Gln Gln Ser Ala Thr Gln Arg Leu Glu His Ala Phe
            180                 185                 190

Asn Ile Ala Arg Tyr Gln Leu Gly Ile Glu Lys Leu Leu Asp Pro Glu
        195                 200                 205

Asp Val Asp Thr Thr Tyr Pro Asp Lys Lys Ser Ile Leu Met Tyr Ile
    210                 215                 220

Thr Ser Leu Phe Gln Val Leu Pro Gln Gln Val Ser Ile Glu Ala Ile
225                 230                 235                 240

Gln Glu Val Glu Met Leu Pro Arg Pro Pro Lys Val Thr Lys Glu Glu
                245                 250                 255

His Phe Gln Leu His His Gln Met His Tyr Ser Gln Ile Thr Val
            260                 265                 270

Ser Leu Ala Gln Gly Tyr Glu Arg Thr Ser Ser Pro Lys Pro Arg Phe
        275                 280                 285

Lys Ser Tyr Ala Tyr Thr Gln Ala Ala Tyr Val Thr Thr Ser Asp Pro
    290                 295                 300

Thr Arg Ser Pro Phe Pro Ser Gln His Leu Glu Ala Pro Glu Asp Lys
305                 310                 315                 320

Ser Phe Gly Ser Ser Leu Met Glu Ser Glu Val Asn Leu Asp Arg Tyr
                325                 330                 335

Gln Thr Ala Leu Glu Glu Val Leu Ser Trp Leu Leu Ser Ala Glu Asp
            340                 345                 350

Thr Leu Gln Ala Gln Gly Glu Ile Ser Asn Asp Val Glu Val Val Lys
        355                 360                 365

Asp Gln Phe His Thr His Glu Gly Tyr Met Met Asp Leu Thr Ala His
    370                 375                 380

-continued

Gln Gly Arg Val Gly Asn Ile Leu Gln Leu Gly Ser Lys Leu Ile Gly
385                 390                 395                 400

Thr Gly Lys Leu Ser Glu Asp Glu Thr Glu Val Gln Glu Gln Met
            405                 410                 415

Asn Leu Leu Asn Ser Arg Trp Glu Cys Leu Arg Val Ala Ser Met Glu
            420                 425                 430

Lys Gln Ser Asn Leu His Arg Val Leu Met Asp Leu Gln Asn Gln Lys
            435                 440                 445

Leu Lys Glu Leu Asn Asp Trp Leu Thr Lys Thr Glu Glu Arg Thr Arg
    450                 455                 460

Lys Met Glu Glu Glu Pro Leu Gly Pro Asp Leu Glu Asp Leu Lys Arg
465                 470                 475                 480

Gln Val Gln Gln His Lys Val Leu Gln Glu Asp Leu Glu Gln Glu Gln
                485                 490                 495

Val Arg Val Asn Ser Leu Thr His Met Val Val Val Asp Glu Ser
            500                 505                 510

Ser Gly Asp His Ala Thr Ala Ala Leu Glu Glu Gln Leu Lys Val Leu
    515                 520                 525

Gly Asp Arg Trp Ala Asn Ile Cys Arg Trp Thr Glu Asp Arg Trp Val
    530                 535                 540

Leu Leu Gln Asp Ile Leu Leu Lys Trp Gln Arg Leu Thr Glu Glu Gln
545                 550                 555                 560

Cys Leu Phe Ser Ala Trp Leu Ser Glu Lys Glu Asp Ala Val Asn Lys
                565                 570                 575

Ile His Thr Thr Gly Phe Lys Asp Gln Asn Glu Met Leu Ser Ser Leu
            580                 585                 590

Gln Lys Leu Ala Val Leu Lys Ala Asp Leu Glu Lys Lys Lys Gln Ser
    595                 600                 605

Met Gly Lys Leu Tyr Ser Leu Lys Gln Asp Leu Leu Ser Thr Leu Lys
    610                 615                 620

Asn Lys Ser Val Thr Gln Lys Thr Glu Ala Trp Leu Asp Asn Phe Ala
625                 630                 635                 640

Arg Cys Trp Asp Asn Leu Val Gln Lys Leu Glu Lys Ser Thr Ala Gln
            645                 650                 655

Ile Ser Gln Ala Val Thr Thr Thr Gln Pro Ser Leu Thr Gln Thr Thr
            660                 665                 670

Val Met Glu Thr Val Thr Thr Val Thr Thr Arg Glu Gln Ile Leu Val
            675                 680                 685

Lys His Ala Gln Glu Glu Leu Pro Pro Pro Pro Gln Lys Lys Arg
    690                 695                 700

Gln Ile Thr Val Asp Ser Glu Ile Arg Lys Arg Leu Asp Val Asp Ile
705                 710                 715                 720

Thr Glu Leu His Ser Trp Ile Thr Arg Ser Glu Ala Val Leu Gln Ser
            725                 730                 735

Pro Glu Phe Ala Ile Phe Arg Lys Glu Gly Asn Phe Ser Asp Leu Lys
            740                 745                 750

Glu Lys Val Asn Ala Ile Glu Arg Glu Lys Ala Glu Lys Phe Arg Lys
            755                 760                 765

Leu Gln Asp Ala Ser Arg Ser Ala Gln Ala Leu Val Glu Gln Met Val
    770                 775                 780

Asn Glu Gly Val Asn Ala Asp Ser Ile Lys Gln Ala Ser Glu Gln Leu
785                 790                 795                 800

Asn Ser Arg Trp Ile Glu Phe Cys Gln Leu Leu Ser Glu Arg Leu Asn

```
                    805                 810                 815
Trp Leu Glu Tyr Gln Asn Asn Ile Ile Ala Phe Tyr Asn Gln Leu Gln
                820                 825                 830

Gln Leu Glu Gln Met Thr Thr Thr Ala Glu Asn Trp Leu Lys Ile Gln
                835                 840                 845

Pro Thr Thr Pro Ser Glu Pro Thr Ala Ile Lys Ser Gln Leu Lys Ile
                850                 855                 860

Cys Lys Asp Glu Val Asn Arg Leu Ser Gly Leu Gln Pro Gln Ile Glu
865                 870                 875                 880

Arg Leu Lys Ile Gln Ser Ile Ala Leu Lys Glu Lys Gly Gln Gly Pro
                885                 890                 895

Met Phe Leu Asp Ala Asp Phe Val Ala Phe Thr Asn His Phe Lys Gln
                900                 905                 910

Val Phe Ser Asp Val Gln Ala Arg Glu Lys Glu Leu Gln Thr Ile Phe
                915                 920                 925

Asp Thr Leu Pro Pro Met Arg Tyr Gln Glu Thr Met Ser Ala Ile Arg
                930                 935                 940

Thr Trp Val Gln Gln Ser Glu Thr Lys Leu Ser Ile Pro Gln Leu Ser
945                 950                 955                 960

Val Thr Asp Tyr Glu Ile Met Glu Gln Arg Leu Gly Glu Leu Gln Ala
                965                 970                 975

Leu Gln Ser Ser Leu Gln Glu Gln Ser Gly Leu Tyr Tyr Leu Ser
                980                 985                 990

Thr Thr Val Lys Glu Met Ser Lys Lys Ala Pro Ser Glu Ile Ser Arg
                995                 1000                1005

Lys Tyr Gln Ser Glu Phe Glu Glu Ile Glu Gly Arg Trp Lys Lys
                1010                1015                1020

Leu Ser Ser Gln Leu Val Glu His Cys Gln Lys Leu Glu Glu Gln
                1025                1030                1035

Met Asn Lys Leu Arg Lys Ile Gln Asn His Ile Gln Thr Leu Lys
                1040                1045                1050

Lys Trp Met Ala Glu Val Asp Val Phe Leu Lys Glu Glu Trp Pro
                1055                1060                1065

Ala Leu Gly Asp Ser Glu Ile Leu Lys Lys Gln Leu Lys Gln Cys
                1070                1075                1080

Arg Leu Leu Val Ser Asp Ile Gln Thr Ile Gln Pro Ser Leu Asn
                1085                1090                1095

Ser Val Asn Glu Gly Gly Gln Lys Ile Lys Asn Glu Ala Glu Pro
                1100                1105                1110

Glu Phe Ala Ser Arg Leu Glu Thr Glu Leu Lys Glu Leu Asn Thr
                1115                1120                1125

Gln Trp Asp His Met Cys Gln Gln Val Tyr Ala Arg Lys Glu Ala
                1130                1135                1140

Leu Lys Gly Gly Leu Glu Lys Thr Val Ser Leu Gln Lys Asp Leu
                1145                1150                1155

Ser Glu Met His Glu Trp Met Thr Gln Ala Glu Glu Glu Tyr Leu
                1160                1165                1170

Glu Arg Asp Phe Glu Tyr Lys Thr Pro Asp Glu Leu Gln Lys Ala
                1175                1180                1185

Val Glu Glu Met Lys Arg Ala Lys Glu Glu Ala Gln Gln Lys Glu
                1190                1195                1200

Ala Lys Val Lys Leu Leu Thr Glu Ser Val Asn Ser Val Ile Ala
                1205                1210                1215
```

-continued

```
Gln Ala Pro Pro Val Ala Gln Glu Ala Leu Lys Lys Glu Leu Glu
    1220            1225            1230

Thr Leu Thr Thr Asn Tyr Gln Trp Leu Cys Thr Arg Leu Asn Gly
    1235            1240            1245

Lys Cys Lys Thr Leu Glu Glu Val Trp Ala Cys Trp His Glu Leu
    1250            1255            1260

Leu Ser Tyr Leu Glu Lys Ala Asn Lys Trp Leu Asn Glu Val Glu
    1265            1270            1275

Phe Lys Leu Lys Thr Thr Glu Asn Ile Pro Gly Gly Ala Glu Glu
    1280            1285            1290

Ile Ser Glu Val Leu Asp Ser Leu Glu Asn Leu Met Arg His Ser
    1295            1300            1305

Glu Asp Asn Pro Asn Gln Ile Arg Ile Leu Ala Gln Thr Leu Thr
    1310            1315            1320

Asp Gly Gly Val Met Asp Glu Leu Ile Asn Glu Glu Leu Glu Thr
    1325            1330            1335

Phe Asn Ser Arg Trp Arg Glu Leu His Glu Glu Ala Val Arg Arg
    1340            1345            1350

Gln Lys Leu Leu Glu Gln Ser Ile Gln Ser Ala Gln Glu Thr Glu
    1355            1360            1365

Lys Ser Leu His Leu Ile Gln Glu Ser Leu Thr Phe Ile Asp Lys
    1370            1375            1380

Gln Leu Ala Ala Tyr Ile Ala Asp Lys Val Asp Ala Ala Gln Met
    1385            1390            1395

Pro Gln Glu Ala Gln Lys Ile Gln Ser Asp Leu Thr Ser His Glu
    1400            1405            1410

Ile Ser Leu Glu Glu Met Lys Lys His Asn Gln Gly Lys Glu Ala
    1415            1420            1425

Ala Gln Arg Val Leu Ser Gln Ile Asp Val Ala Gln Lys Lys Leu
    1430            1435            1440

Gln Asp Val Ser Met Lys Phe Arg Leu Phe Gln Lys Pro Ala Asn
    1445            1450            1455

Phe Glu Gln Arg Leu Gln Glu Ser Lys Met Ile Leu Asp Glu Val
    1460            1465            1470

Lys Met His Leu Pro Ala Leu Glu Thr Lys Ser Val Glu Gln Glu
    1475            1480            1485

Val Val Gln Ser Gln Leu Asn His Cys Val Asn Leu Tyr Lys Ser
    1490            1495            1500

Leu Ser Glu Val Lys Ser Glu Val Glu Met Val Ile Lys Thr Gly
    1505            1510            1515

Arg Gln Ile Val Gln Lys Lys Gln Thr Glu Asn Pro Lys Glu Leu
    1520            1525            1530

Asp Glu Arg Val Thr Ala Leu Lys Leu His Tyr Asn Glu Leu Gly
    1535            1540            1545

Ala Lys Val Thr Glu Arg Lys Gln Gln Leu Glu Lys Cys Leu Lys
    1550            1555            1560

Leu Ser Arg Lys Met Arg Lys Glu Met Asn Val Leu Thr Glu Trp
    1565            1570            1575

Leu Ala Ala Thr Asp Met Glu Leu Thr Lys Arg Ser Ala Val Glu
    1580            1585            1590

Gly Met Pro Ser Asn Leu Asp Ser Glu Val Ala Trp Gly Lys Ala
    1595            1600            1605
```

-continued

```
Thr Gln Lys Glu Ile Glu Lys Gln Lys Val His Leu Lys Ser Ile
    1610            1615                1620
Thr Glu Val Gly Glu Ala Leu Lys Thr Val Leu Gly Lys Lys Glu
    1625            1630                1635
Thr Leu Val Glu Asp Lys Leu Ser Leu Leu Asn Ser Asn Trp Ile
    1640            1645                1650
Ala Val Thr Ser Arg Ala Glu Glu Trp Leu Asn Leu Leu Leu Glu
    1655            1660                1665
Tyr Gln Lys His Met Glu Thr Phe Asp Gln Asn Val Asp His Ile
    1670            1675                1680
Thr Lys Trp Ile Ile Gln Ala Asp Thr Leu Leu Asp Glu Ser Glu
    1685            1690                1695
Lys Lys Lys Pro Gln Gln Lys Glu Asp Val Leu Lys Arg Leu Lys
    1700            1705                1710
Ala Glu Leu Asn Asp Ile Arg Pro Lys Val Asp Ser Thr Arg Asp
    1715            1720                1725
Gln Ala Ala Asn Leu Met Ala Asn Arg Gly Asp His Cys Arg Lys
    1730            1735                1740
Leu Val Glu Pro Gln Ile Ser Glu Leu Asn His Arg Phe Ala Ala
    1745            1750                1755
Ile Ser His Arg Ile Lys Thr Gly Lys Ala Ser Ile Pro Leu Lys
    1760            1765                1770
Glu Leu Glu Gln Phe Asn Ser Asp Ile Gln Lys Leu Leu Glu Pro
    1775            1780                1785
Leu Glu Ala Glu Ile Gln Gln Gly Val Asn Leu Lys Glu Glu Asp
    1790            1795                1800
Phe Asn Lys Asp Met Asn Glu Asp Asn Glu Gly Thr Val Lys Glu
    1805            1810                1815
Leu Leu Gln Arg Gly Asp Asn Leu Gln Gln Arg Ile Thr Asp Glu
    1820            1825                1830
Arg Lys Arg Glu Glu Ile Lys Ile Lys Gln Gln Leu Leu Gln Thr
    1835            1840                1845
Lys His Asn Ala Leu Lys Asp Leu Arg Ser Gln Arg Arg Lys Lys
    1850            1855                1860
Ala Leu Glu Ile Ser His Gln Trp Tyr Gln Tyr Lys Arg Gln Ala
    1865            1870                1875
Asp Asp Leu Leu Lys Cys Leu Asp Asp Ile Glu Lys Lys Leu Ala
    1880            1885                1890
Ser Leu Pro Glu Pro Arg Asp Glu Arg Lys Ile Lys Glu Ile Asp
    1895            1900                1905
Arg Glu Leu Gln Lys Lys Lys Glu Glu Leu Asn Ala Val Arg Arg
    1910            1915                1920
Gln Ala Glu Gly Leu Ser Glu Asp Gly Ala Ala Met Ala Val Glu
    1925            1930                1935
Pro Thr Gln Ile Gln Leu Ser Lys Arg Trp Arg Glu Ile Glu Ser
    1940            1945                1950
Lys Phe Ala Gln Phe Arg Arg Leu Asn Phe Ala Gln Ile His Thr
    1955            1960                1965
Val Arg Glu Glu Thr Met Met Val Met Thr Glu Asp Met Pro Leu
    1970            1975                1980
Glu Ile Ser Tyr Val Pro Ser Thr Tyr Leu Thr Glu Ile Thr His
    1985            1990                1995
Val Ser Gln Ala Leu Leu Glu Val Glu Gln Leu Leu Asn Ala Pro
```

```
                2000                2005                2010
Asp Leu Cys Ala Lys Asp Phe Glu Asp Leu Phe Lys Gln Glu Glu
    2015                2020                2025

Ser Leu Lys Asn Ile Lys Asp Ser Leu Gln Gln Ser Ser Gly Arg
    2030                2035                2040

Ile Asp Ile Ile His Ser Lys Lys Thr Ala Ala Leu Gln Ser Ala
    2045                2050                2055

Thr Pro Val Glu Arg Val Lys Leu Gln Glu Ala Leu Ser Gln Leu
    2060                2065                2070

Asp Phe Gln Trp Glu Lys Val Asn Lys Met Tyr Lys Asp Arg Gln
    2075                2080                2085

Gly Arg Phe Asp Arg Ser Val Glu Lys Trp Arg Arg Phe His Tyr
    2090                2095                2100

Asp Ile Lys Ile Phe Asn Gln Trp Leu Thr Glu Ala Glu Gln Phe
    2105                2110                2115

Leu Arg Lys Thr Gln Ile Pro Glu Asn Trp Glu His Ala Lys Tyr
    2120                2125                2130

Lys Trp Tyr Leu Lys Glu Leu Gln Asp Gly Ile Gly Gln Arg Gln
    2135                2140                2145

Thr Val Val Arg Thr Leu Asn Ala Thr Gly Glu Glu Ile Ile Gln
    2150                2155                2160

Gln Ser Ser Lys Thr Asp Ala Ser Ile Leu Gln Glu Lys Leu Gly
    2165                2170                2175

Ser Leu Asn Leu Arg Trp Gln Glu Val Cys Lys Gln Leu Ser Asp
    2180                2185                2190

Arg Lys Lys Arg Leu Glu Glu Gln Lys Asn Ile Leu Ser Glu Phe
    2195                2200                2205

Gln Arg Asp Leu Asn Glu Phe Val Leu Trp Leu Glu Glu Ala Asp
    2210                2215                2220

Asn Ile Ala Ser Ile Pro Leu Glu Pro Gly Lys Glu Gln Gln Leu
    2225                2230                2235

Lys Glu Lys Leu Glu Gln Val Lys Leu Leu Val Glu Glu Leu Pro
    2240                2245                2250

Leu Arg Gln Gly Ile Leu Lys Gln Leu Asn Glu Thr Gly Gly Pro
    2255                2260                2265

Val Leu Val Ser Ala Pro Ile Ser Pro Glu Glu Gln Asp Lys Leu
    2270                2275                2280

Glu Asn Lys Leu Lys Gln Thr Asn Leu Gln Trp Ile Lys Val Ser
    2285                2290                2295

Arg Ala Leu Pro Glu Lys Gln Gly Glu Ile Glu Ala Gln Ile Lys
    2300                2305                2310

Asp Leu Gly Gln Leu Glu Lys Lys Leu Glu Asp Leu Glu Glu Gln
    2315                2320                2325

Leu Asn His Leu Leu Leu Trp Leu Ser Pro Ile Arg Asn Gln Leu
    2330                2335                2340

Glu Ile Tyr Asn Gln Pro Asn Gln Glu Gly Pro Phe Asp Val Gln
    2345                2350                2355

Glu Thr Glu Ile Ala Val Gln Ala Lys Gln Pro Asp Val Glu Glu
    2360                2365                2370

Ile Leu Ser Lys Gly Gln His Leu Tyr Lys Glu Lys Pro Ala Thr
    2375                2380                2385

Gln Pro Val Lys Arg Lys Leu Glu Asp Leu Ser Ser Glu Trp Lys
    2390                2395                2400
```

```
Ala Val Asn Arg Leu Leu Gln Glu Leu Arg Ala Lys Gln Pro Asp
    2405                2410                2415

Leu Ala Pro Gly Leu Thr Thr Ile Gly Ala Ser Pro Thr Gln Thr
    2420                2425                2430

Val Thr Leu Val Thr Gln Pro Val Val Thr Lys Glu Thr Ala Ile
    2435                2440                2445

Ser Lys Leu Glu Met Pro Ser Ser Leu Met Leu Glu Val Pro Ala
    2450                2455                2460

Leu Ala Asp Phe Asn Arg Ala Trp Thr Glu Leu Thr Asp Trp Leu
    2465                2470                2475

Ser Leu Leu Asp Gln Val Ile Lys Ser Gln Arg Val Met Val Gly
    2480                2485                2490

Asp Leu Glu Asp Ile Asn Glu Met Ile Ile Lys Gln Lys Ala Thr
    2495                2500                2505

Met Gln Asp Leu Glu Gln Arg Arg Pro Gln Leu Glu Glu Leu Ile
    2510                2515                2520

Thr Ala Ala Gln Asn Leu Lys Asn Lys Thr Ser Asn Gln Glu Ala
    2525                2530                2535

Arg Thr Ile Ile Thr Asp Arg Ile Glu Arg Ile Gln Asn Gln Trp
    2540                2545                2550

Asp Glu Val Gln Glu His Leu Gln Asn Arg Arg Gln Gln Leu Asn
    2555                2560                2565

Glu Met Leu Lys Asp Ser Thr Gln Trp Leu Glu Ala Lys Glu Glu
    2570                2575                2580

Ala Glu Gln Val Leu Gly Gln Ala Arg Ala Lys Leu Glu Ser Trp
    2585                2590                2595

Lys Glu Gly Pro Tyr Thr Val Asp Ala Ile Gln Lys Lys Ile Thr
    2600                2605                2610

Glu Thr Lys Gln Leu Ala Lys Asp Leu Arg Gln Trp Gln Thr Asn
    2615                2620                2625

Val Asp Val Ala Asn Asp Leu Ala Leu Lys Leu Leu Arg Asp Tyr
    2630                2635                2640

Ser Ala Asp Asp Thr Arg Lys Val His Met Ile Thr Glu Asn Ile
    2645                2650                2655

Asn Ala Ser Trp Arg Ser Ile His Lys Arg Val Ser Glu Arg Glu
    2660                2665                2670

Ala Ala Leu Glu Glu Thr His Arg Leu Leu Gln Gln Phe Pro Leu
    2675                2680                2685

Asp Leu Glu Lys Phe Leu Ala Trp Leu Thr Glu Ala Glu Thr Thr
    2690                2695                2700

Ala Asn Val Leu Gln Asp Ala Thr Arg Lys Glu Arg Leu Leu Glu
    2705                2710                2715

Asp Ser Lys Gly Val Lys Glu Leu Met Lys Gln Trp Gln Asp Leu
    2720                2725                2730

Gln Gly Glu Ile Glu Ala His Thr Asp Val Tyr His Asn Leu Asp
    2735                2740                2745

Glu Asn Ser Gln Lys Ile Leu Arg Ser Leu Glu Gly Ser Asp Asp
    2750                2755                2760

Ala Val Leu Leu Gln Arg Arg Leu Asp Asn Met Asn Phe Lys Trp
    2765                2770                2775

Ser Glu Leu Arg Lys Lys Ser Leu Asn Ile Arg Ser His Leu Glu
    2780                2785                2790
```

```
Ala Ser Ser Asp Gln Trp Lys Arg Leu His Leu Ser Leu Gln Glu
2795                2800                2805

Leu Leu Val Trp Leu Gln Leu Lys Asp Asp Glu Leu Ser Arg Gln
2810                2815                2820

Ala Pro Ile Gly Gly Asp Phe Pro Ala Val Gln Lys Gln Asn Asp
2825                2830                2835

Val His Arg Ala Phe Lys Arg Glu Leu Lys Thr Lys Glu Pro Val
2840                2845                2850

Ile Met Ser Thr Leu Glu Thr Val Arg Ile Phe Leu Thr Glu Gln
2855                2860                2865

Pro Leu Glu Gly Leu Glu Lys Leu Tyr Gln Glu Pro Arg Glu Leu
2870                2875                2880

Pro Pro Glu Glu Arg Ala Gln Asn Val Thr Arg Leu Leu Arg Lys
2885                2890                2895

Gln Ala Glu Glu Val Asn Thr Glu Trp Glu Lys Leu Asn Leu His
2900                2905                2910

Ser Ala Asp Trp Gln Arg Lys Ile Asp Glu Thr Leu Glu Arg Leu
2915                2920                2925

Gln Glu Leu Gln Glu Ala Thr Asp Glu Leu Asp Leu Lys Leu Arg
2930                2935                2940

Gln Ala Glu Val Ile Lys Gly Ser Trp Gln Pro Val Gly Asp Leu
2945                2950                2955

Leu Ile Asp Ser Leu Gln Asp His Leu Glu Lys Val Lys Ala Leu
2960                2965                2970

Arg Gly Glu Ile Ala Pro Leu Lys Glu Asn Val Ser His Val Asn
2975                2980                2985

Asp Leu Ala Arg Gln Leu Thr Thr Leu Gly Ile Gln Leu Ser Pro
2990                2995                3000

Tyr Asn Leu Ser Thr Leu Glu Asp Leu Asn Thr Arg Trp Lys Leu
3005                3010                3015

Leu Gln Val Ala Val Glu Asp Arg Val Arg Gln Leu His Glu Ala
3020                3025                3030

His Arg Asp Phe Gly Pro Ala Ser Gln His Phe Leu Ser Thr Ser
3035                3040                3045

Val Gln Gly Pro Trp Glu Arg Ala Ile Ser Pro Asn Lys Val Pro
3050                3055                3060

Tyr Tyr Ile Asn His Glu Thr Gln Thr Thr Cys Trp Asp His Pro
3065                3070                3075

Lys Met Thr Glu Leu Tyr Gln Ser Leu Ala Asp Leu Asn Asn Val
3080                3085                3090

Arg Phe Ser Ala Tyr Arg Thr Ala Met Lys Leu Arg Arg Leu Gln
3095                3100                3105

Lys Ala Leu Cys Leu Asp Leu Leu Ser Leu Ser Ala Ala Cys Asp
3110                3115                3120

Ala Leu Asp Gln His Asn Leu Lys Gln Asn Asp Gln Pro Met Asp
3125                3130                3135

Ile Leu Gln Ile Ile Asn Cys Leu Thr Thr Ile Tyr Asp Arg Leu
3140                3145                3150

Glu Gln Glu His Asn Asn Leu Val Asn Val Pro Leu Cys Val Asp
3155                3160                3165

Met Cys Leu Asn Trp Leu Leu Asn Val Tyr Asp Thr Gly Arg Thr
3170                3175                3180

Gly Arg Ile Arg Val Leu Ser Phe Lys Thr Gly Ile Ile Ser Leu
```

-continued

```
                3185                3190                3195

Cys Lys Ala His Leu Glu Asp Lys Tyr Arg Tyr Leu Phe Lys Gln
    3200                3205                3210

Val Ala Ser Ser Thr Gly Phe Cys Asp Gln Arg Arg Leu Gly Leu
    3215                3220                3225

Leu Leu His Asp Ser Ile Gln Ile Pro Arg Gln Leu Gly Glu Val
    3230                3235                3240

Ala Ser Phe Gly Gly Ser Asn Ile Glu Pro Ser Val Arg Ser Cys
    3245                3250                3255

Phe Gln Phe Ala Asn Asn Lys Pro Glu Ile Glu Ala Ala Leu Phe
    3260                3265                3270

Leu Asp Trp Met Arg Leu Glu Pro Gln Ser Met Val Trp Leu Pro
    3275                3280                3285

Val Leu His Arg Val Ala Ala Glu Thr Ala Lys His Gln Ala
    3290                3295                3300

Lys Cys Asn Ile Cys Lys Glu Cys Pro Ile Ile Gly Phe Arg Tyr
    3305                3310                3315

Arg Ser Leu Lys His Phe Asn Tyr Asp Ile Cys Gln Ser Cys Phe
    3320                3325                3330

Phe Ser Gly Arg Val Ala Lys Gly His Lys Met His Tyr Pro Met
    3335                3340                3345

Val Glu Tyr Cys Thr Pro Thr Thr Ser Gly Glu Asp Val Arg Asp
    3350                3355                3360

Phe Ala Lys Val Leu Lys Asn Lys Phe Arg Thr Lys Arg Tyr Phe
    3365                3370                3375

Ala Lys His Pro Arg Met Gly Tyr Leu Pro Val Gln Thr Val Leu
    3380                3385                3390

Glu Gly Asp Asn Met Glu Thr Pro Val Thr Leu Ile Asn Phe Trp
    3395                3400                3405

Pro Val Asp Ser Ala Pro Ala Ser Ser Pro Gln Leu Ser His Asp
    3410                3415                3420

Asp Thr His Ser Arg Ile Glu His Tyr Ala Ser Arg Leu Ala Glu
    3425                3430                3435

Met Glu Asn Ser Asn Gly Ser Tyr Leu Asn Asp Ser Ile Ser Pro
    3440                3445                3450

Asn Glu Ser Ile Asp Asp Glu His Leu Leu Ile Gln His Tyr Cys
    3455                3460                3465

Gln Ser Leu Asn Gln Asp Ser Pro Leu Ser Gln Pro Arg Ser Pro
    3470                3475                3480

Ala Gln Ile Leu Ile Ser Leu Glu Ser Glu Glu Arg Gly Glu Leu
    3485                3490                3495

Glu Arg Ile Leu Ala Asp Leu Glu Glu Glu Asn Arg Asn Leu Gln
    3500                3505                3510

Ala Glu Tyr Asp Arg Leu Lys Gln Gln His Glu His Lys Gly Leu
    3515                3520                3525

Ser Pro Leu Pro Ser Pro Pro Glu Met Met Pro Thr Ser Pro Gln
    3530                3535                3540

Ser Pro Arg Asp Ala Glu Leu Ile Ala Glu Ala Lys Leu Leu Arg
    3545                3550                3555

Gln His Lys Gly Arg Leu Glu Ala Arg Met Gln Ile Leu Glu Asp
    3560                3565                3570

His Asn Lys Gln Leu Glu Ser Gln Leu His Arg Leu Arg Gln Leu
    3575                3580                3585
```

Leu Glu Gln Pro Gln Ala Glu Ala Lys Val Asn Gly Thr Thr Val
    3590            3595                3600

Ser Ser Pro Ser Thr Ser Leu Gln Arg Ser Asp Ser Ser Gln Pro
3605            3610                3615

Met Leu Leu Arg Val Val Gly Ser Gln Thr Ser Asp Ser Met Gly
    3620            3625                3630

Glu Glu Asp Leu Leu Ser Pro Pro Gln Asp Thr Ser Thr Gly Leu
    3635            3640                3645

Glu Glu Val Met Glu Gln Leu Asn Asn Ser Phe Pro Ser Ser Arg
    3650            3655                3660

Gly Arg Asn Thr Pro Gly Lys Pro Met Arg Glu Asp Thr Met
    3665            3670                3675

<210> SEQ ID NO 5
<211> LENGTH: 536
<212> TYPE: PRT
<213> ORGANISM: Homo sapiens

<400> SEQUENCE: 5

Met Glu Phe Ser Ser Pro Ser Arg Glu Glu Cys Pro Lys Pro Leu Ser
1               5                   10                  15

Arg Val Ser Ile Met Ala Gly Ser Leu Thr Gly Leu Leu Leu Leu Gln
                20                  25                  30

Ala Val Ser Trp Ala Ser Gly Ala Arg Pro Cys Ile Pro Lys Ser Phe
            35                  40                  45

Gly Tyr Ser Ser Val Val Cys Val Cys Asn Ala Thr Tyr Cys Asp Ser
        50                  55                  60

Phe Asp Pro Pro Thr Phe Pro Ala Leu Gly Thr Phe Ser Arg Tyr Glu
65                  70                  75                  80

Ser Thr Arg Ser Gly Arg Arg Met Glu Leu Ser Met Gly Pro Ile Gln
                85                  90                  95

Ala Asn His Thr Gly Thr Gly Leu Leu Leu Thr Leu Gln Pro Glu Gln
            100                 105                 110

Lys Phe Gln Lys Val Lys Gly Phe Gly Gly Ala Met Thr Asp Ala Ala
        115                 120                 125

Ala Leu Asn Ile Leu Ala Leu Ser Pro Pro Ala Gln Asn Leu Leu Leu
    130                 135                 140

Lys Ser Tyr Phe Ser Glu Glu Gly Ile Gly Tyr Asn Ile Ile Arg Val
145                 150                 155                 160

Pro Met Ala Ser Cys Asp Phe Ser Ile Arg Thr Tyr Thr Tyr Ala Asp
                165                 170                 175

Thr Pro Asp Asp Phe Gln Leu His Asn Phe Ser Leu Pro Glu Glu Asp
            180                 185                 190

Thr Lys Leu Lys Ile Pro Leu Ile His Arg Ala Leu Gln Leu Ala Gln
        195                 200                 205

Arg Pro Val Ser Leu Leu Ala Ser Pro Trp Thr Ser Pro Thr Trp Leu
    210                 215                 220

Lys Thr Asn Gly Ala Val Asn Gly Lys Gly Ser Leu Lys Gly Gln Pro
225                 230                 235                 240

Gly Asp Ile Tyr His Gln Thr Trp Ala Arg Tyr Phe Val Lys Phe Leu
                245                 250                 255

Asp Ala Tyr Ala Glu His Lys Leu Gln Phe Trp Ala Val Thr Ala Glu
            260                 265                 270

Asn Glu Pro Ser Ala Gly Leu Leu Ser Gly Tyr Pro Phe Gln Cys Leu

```
                275                 280                 285
Gly Phe Thr Pro Glu His Gln Arg Asp Phe Ile Ala Arg Asp Leu Gly
    290                 295                 300

Pro Thr Leu Ala Asn Ser Thr His His Asn Val Arg Leu Leu Met Leu
305                 310                 315                 320

Asp Asp Gln Arg Leu Leu Leu Pro His Trp Ala Lys Val Val Leu Thr
                325                 330                 335

Asp Pro Glu Ala Ala Lys Tyr Val His Gly Ile Ala Val His Trp Tyr
            340                 345                 350

Leu Asp Phe Leu Ala Pro Ala Lys Ala Thr Leu Gly Glu Thr His Arg
        355                 360                 365

Leu Phe Pro Asn Thr Met Leu Phe Ala Ser Glu Ala Cys Val Gly Ser
    370                 375                 380

Lys Phe Trp Glu Gln Ser Val Arg Leu Gly Ser Trp Asp Arg Gly Met
385                 390                 395                 400

Gln Tyr Ser His Ser Ile Ile Thr Asn Leu Leu Tyr His Val Val Gly
                405                 410                 415

Trp Thr Asp Trp Asn Leu Ala Leu Asn Pro Glu Gly Gly Pro Asn Trp
            420                 425                 430

Val Arg Asn Phe Val Asp Ser Pro Ile Ile Val Asp Ile Thr Lys Asp
        435                 440                 445

Thr Phe Tyr Lys Gln Pro Met Phe Tyr His Leu Gly His Phe Ser Lys
    450                 455                 460

Phe Ile Pro Glu Gly Ser Gln Arg Val Gly Leu Val Ala Ser Gln Lys
465                 470                 475                 480

Asn Asp Leu Asp Ala Val Ala Leu Met His Pro Asp Gly Ser Ala Val
                485                 490                 495

Val Val Val Leu Asn Arg Ser Ser Lys Asp Val Pro Leu Thr Ile Lys
            500                 505                 510

Asp Pro Ala Val Gly Phe Leu Glu Thr Ile Ser Pro Gly Tyr Ser Ile
        515                 520                 525

His Thr Tyr Leu Trp Arg Arg Gln
    530                 535

<210> SEQ ID NO 6
<211> LENGTH: 110
<212> TYPE: PRT
<213> ORGANISM: Homo sapiens

<400> SEQUENCE: 6

Met Ala Leu Trp Met Arg Leu Leu Pro Leu Leu Ala Leu Leu Ala Leu
1               5                   10                  15

Trp Gly Pro Asp Pro Ala Ala Ala Phe Val Asn Gln His Leu Cys Gly
                20                  25                  30

Ser His Leu Val Glu Ala Leu Tyr Leu Val Cys Gly Glu Arg Gly Phe
            35                  40                  45

Phe Tyr Thr Pro Lys Thr Arg Arg Glu Ala Glu Asp Leu Gln Val Gly
        50                  55                  60

Gln Val Glu Leu Gly Gly Gly Pro Gly Ala Gly Ser Leu Gln Pro Leu
65                  70                  75                  80

Ala Leu Glu Gly Ser Leu Gln Lys Arg Gly Ile Val Glu Gln Cys Cys
                85                  90                  95

Thr Ser Ile Cys Ser Leu Tyr Gln Leu Glu Asn Tyr Cys Asn
            100                 105                 110
```

<210> SEQ ID NO 7
<211> LENGTH: 1065
<212> TYPE: PRT
<213> ORGANISM: Homo sapiens

<400> SEQUENCE: 7

```
Met Lys Ile Leu Ile Leu Gly Ile Phe Leu Phe Leu Cys Ser Thr Pro
1               5                   10                  15

Ala Trp Ala Lys Glu Lys His Tyr Tyr Ile Gly Ile Ile Glu Thr Thr
            20                  25                  30

Trp Asp Tyr Ala Ser Asp His Gly Glu Lys Lys Leu Ile Ser Val Asp
        35                  40                  45

Thr Glu His Ser Asn Ile Tyr Leu Gln Asn Gly Pro Asp Arg Ile Gly
    50                  55                  60

Arg Leu Tyr Lys Lys Ala Leu Tyr Leu Gln Tyr Thr Asp Glu Thr Phe
65                  70                  75                  80

Arg Thr Thr Ile Glu Lys Pro Val Trp Leu Gly Phe Leu Gly Pro Ile
                85                  90                  95

Ile Lys Ala Glu Thr Gly Asp Lys Val Tyr Val His Leu Lys Asn Leu
            100                 105                 110

Ala Ser Arg Pro Tyr Thr Phe His Ser His Gly Ile Thr Tyr Tyr Lys
        115                 120                 125

Glu His Glu Gly Ala Ile Tyr Pro Asp Asn Thr Thr Asp Phe Gln Arg
    130                 135                 140

Ala Asp Asp Lys Val Tyr Pro Gly Glu Gln Tyr Thr Tyr Met Leu Leu
145                 150                 155                 160

Ala Thr Glu Glu Gln Ser Pro Gly Glu Gly Asp Gly Asn Cys Val Thr
                165                 170                 175

Arg Ile Tyr His Ser His Ile Asp Ala Pro Lys Asp Ile Ala Ser Gly
            180                 185                 190

Leu Ile Gly Pro Leu Ile Ile Cys Lys Lys Asp Ser Leu Asp Lys Glu
        195                 200                 205

Lys Glu Lys His Ile Asp Arg Glu Phe Val Val Met Phe Ser Val Val
    210                 215                 220

Asp Glu Asn Phe Ser Trp Tyr Leu Glu Asp Asn Ile Lys Thr Tyr Cys
225                 230                 235                 240

Ser Glu Pro Glu Lys Val Asp Lys Asp Asn Glu Asp Phe Gln Glu Ser
                245                 250                 255

Asn Arg Met Tyr Ser Val Asn Gly Tyr Thr Phe Gly Ser Leu Pro Gly
            260                 265                 270

Leu Ser Met Cys Ala Glu Asp Arg Val Lys Trp Tyr Leu Phe Gly Met
        275                 280                 285

Gly Asn Glu Val Asp Val His Ala Ala Phe Phe His Gly Gln Ala Leu
    290                 295                 300

Thr Asn Lys Asn Tyr Arg Ile Asp Thr Ile Asn Leu Phe Pro Ala Thr
305                 310                 315                 320

Leu Phe Asp Ala Tyr Met Val Ala Gln Asn Pro Gly Glu Trp Met Leu
                325                 330                 335

Ser Cys Gln Asn Leu Asn His Leu Lys Ala Gly Leu Gln Ala Phe Phe
            340                 345                 350

Gln Val Gln Glu Cys Asn Lys Ser Ser Ser Lys Asp Asn Ile Arg Gly
        355                 360                 365

Lys His Val Arg His Tyr Tyr Ile Ala Ala Glu Glu Ile Ile Trp Asn
    370                 375                 380
```

```
Tyr Ala Pro Ser Gly Ile Asp Ile Phe Thr Lys Glu Asn Leu Thr Ala
385                 390                 395                 400

Pro Gly Ser Asp Ser Ala Val Phe Phe Glu Gln Gly Thr Thr Arg Ile
            405                 410                 415

Gly Gly Ser Tyr Lys Lys Leu Val Tyr Arg Glu Tyr Thr Asp Ala Ser
            420                 425                 430

Phe Thr Asn Arg Lys Glu Arg Gly Pro Glu Glu His Leu Gly Ile
        435                 440                 445

Leu Gly Pro Val Ile Trp Ala Glu Val Gly Asp Thr Ile Arg Val Thr
450                 455                 460

Phe His Asn Lys Gly Ala Tyr Pro Leu Ser Ile Glu Pro Ile Gly Val
465                 470                 475                 480

Arg Phe Asn Lys Asn Asn Glu Gly Thr Tyr Tyr Ser Pro Asn Tyr Asn
            485                 490                 495

Pro Gln Ser Arg Ser Val Pro Pro Ser Ala Ser His Val Ala Pro Thr
            500                 505                 510

Glu Thr Phe Thr Tyr Glu Trp Thr Val Pro Lys Glu Val Gly Pro Thr
        515                 520                 525

Asn Ala Asp Pro Val Cys Leu Ala Lys Met Tyr Tyr Ser Ala Val Asp
530                 535                 540

Pro Thr Lys Asp Ile Phe Thr Gly Leu Ile Gly Pro Met Lys Ile Cys
545                 550                 555                 560

Lys Lys Gly Ser Leu His Ala Asn Gly Arg Gln Lys Asp Val Asp Lys
            565                 570                 575

Glu Phe Tyr Leu Phe Pro Thr Val Phe Asp Glu Asn Glu Ser Leu Leu
        580                 585                 590

Leu Glu Asp Asn Ile Arg Met Phe Thr Thr Ala Pro Asp Gln Val Asp
        595                 600                 605

Lys Glu Asp Glu Asp Phe Gln Glu Ser Asn Lys Met His Ser Met Asn
610                 615                 620

Gly Phe Met Tyr Gly Asn Gln Pro Gly Leu Thr Met Cys Lys Gly Asp
625                 630                 635                 640

Ser Val Val Trp Tyr Leu Phe Ser Ala Gly Asn Glu Ala Asp Val His
            645                 650                 655

Gly Ile Tyr Phe Ser Gly Asn Thr Tyr Leu Trp Arg Gly Glu Arg Arg
            660                 665                 670

Asp Thr Ala Asn Leu Phe Pro Gln Thr Ser Leu Thr Leu His Met Trp
        675                 680                 685

Pro Asp Thr Glu Gly Thr Phe Asn Val Glu Cys Leu Thr Thr Asp His
        690                 695                 700

Tyr Thr Gly Gly Met Lys Gln Lys Tyr Thr Val Asn Gln Cys Arg Arg
705                 710                 715                 720

Gln Ser Glu Asp Ser Thr Phe Tyr Leu Gly Glu Arg Thr Tyr Tyr Ile
            725                 730                 735

Ala Ala Val Glu Val Glu Trp Asp Tyr Ser Pro Gln Arg Glu Trp Glu
            740                 745                 750

Lys Glu Leu His His Leu Gln Glu Gln Asn Val Ser Asn Ala Phe Leu
        755                 760                 765

Asp Lys Gly Glu Phe Tyr Ile Gly Ser Lys Tyr Lys Lys Val Val Tyr
        770                 775                 780

Arg Gln Tyr Thr Asp Ser Thr Phe Arg Val Pro Val Glu Arg Lys Ala
785                 790                 795                 800
```

Glu Glu Glu His Leu Gly Ile Leu Gly Pro Gln Leu His Ala Asp Val
            805                 810                 815

Gly Asp Lys Val Lys Ile Ile Phe Lys Asn Met Ala Thr Arg Pro Tyr
        820                 825                 830

Ser Ile His Ala His Gly Val Gln Thr Glu Ser Ser Thr Val Thr Pro
        835                 840                 845

Thr Leu Pro Gly Glu Thr Leu Thr Tyr Val Trp Lys Ile Pro Glu Arg
850                 855                 860

Ser Gly Ala Gly Thr Glu Asp Ser Ala Cys Ile Pro Trp Ala Tyr Tyr
865                 870                 875                 880

Ser Thr Val Asp Gln Val Lys Asp Leu Tyr Ser Gly Leu Ile Gly Pro
            885                 890                 895

Leu Ile Val Cys Arg Arg Pro Tyr Leu Lys Val Phe Asn Pro Arg Arg
            900                 905                 910

Lys Leu Glu Phe Ala Leu Leu Phe Leu Val Phe Asp Glu Asn Glu Ser
            915                 920                 925

Trp Tyr Leu Asp Asp Asn Ile Lys Thr Tyr Ser Asp His Pro Glu Lys
            930                 935                 940

Val Asn Lys Asp Asp Glu Glu Phe Ile Glu Ser Asn Lys Met His Ala
945                 950                 955                 960

Ile Asn Gly Arg Met Phe Gly Asn Leu Gln Gly Leu Thr Met His Val
            965                 970                 975

Gly Asp Glu Val Asn Trp Tyr Leu Met Gly Met Gly Asn Glu Ile Asp
            980                 985                 990

Leu His Thr Val His Phe His Gly His Ser Phe Gln Tyr Lys His Arg
            995                 1000                1005

Gly Val Tyr Ser Ser Asp Val Phe Asp Ile Phe Pro Gly Thr Tyr
        1010                1015                1020

Gln Thr Leu Glu Met Phe Pro Arg Thr Pro Gly Ile Trp Leu Leu
        1025                1030                1035

His Cys His Val Thr Asp His Ile His Ala Gly Met Glu Thr Thr
        1040                1045                1050

Tyr Thr Val Leu Gln Asn Glu Asp Thr Lys Ser Gly
        1055                1060                1065

<210> SEQ ID NO 8
<211> LENGTH: 471
<212> TYPE: PRT
<213> ORGANISM: Escherichia coli

<400> SEQUENCE: 8

Met Lys Gln Ser Thr Ile Ala Leu Ala Leu Leu Pro Leu Leu Phe Thr
1               5                   10                  15

Pro Val Thr Lys Ala Arg Thr Pro Glu Met Pro Val Leu Glu Asn Arg
            20                  25                  30

Ala Ala Gln Gly Asp Ile Thr Ala Pro Gly Gly Ala Arg Arg Leu Thr
        35                  40                  45

Gly Asp Gln Thr Ala Ala Leu Arg Asp Ser Leu Ser Asp Lys Pro Ala
    50                  55                  60

Lys Asn Ile Ile Leu Leu Ile Gly Asp Gly Met Gly Asp Ser Glu Ile
65                  70                  75                  80

Thr Ala Ala Arg Asn Tyr Ala Glu Gly Ala Gly Gly Phe Phe Lys Gly
                85                  90                  95

Ile Asp Ala Leu Pro Leu Thr Gly Gln Tyr Thr His Tyr Ala Leu Asn
            100                 105                 110

Lys Lys Thr Gly Lys Pro Asp Tyr Val Thr Asp Ser Ala Ala Ser Ala
         115                 120                 125

Thr Ala Trp Ser Thr Gly Val Lys Thr Tyr Asn Gly Ala Leu Gly Val
    130                 135                 140

Asp Ile His Glu Lys Asp His Pro Thr Ile Leu Glu Met Ala Lys Ala
145                 150                 155                 160

Ala Gly Leu Ala Thr Gly Asn Val Ser Thr Ala Glu Leu Gln Asp Ala
                165                 170                 175

Thr Pro Ala Ala Leu Val Ala His Val Thr Ser Arg Lys Cys Tyr Gly
                180                 185                 190

Pro Ser Ala Thr Ser Glu Lys Cys Pro Gly Asn Ala Leu Glu Lys Gly
                195                 200                 205

Gly Lys Gly Ser Ile Thr Glu Gln Leu Leu Asn Ala Arg Ala Asp Val
            210                 215                 220

Thr Leu Gly Gly Gly Ala Lys Thr Phe Ala Glu Thr Ala Thr Ala Gly
225                 230                 235                 240

Glu Trp Gln Gly Lys Thr Leu Arg Glu Gln Ala Gln Ala Arg Gly Tyr
                245                 250                 255

Gln Leu Val Ser Asp Ala Ala Ser Leu Asn Ser Val Thr Glu Ala Asn
            260                 265                 270

Gln Gln Lys Pro Leu Leu Gly Leu Phe Ala Asp Gly Asn Met Pro Val
        275                 280                 285

Arg Trp Leu Gly Pro Lys Ala Thr Tyr His Gly Asn Ile Asp Lys Pro
    290                 295                 300

Ala Val Thr Cys Thr Pro Asn Pro Gln Arg Asn Asp Ser Val Pro Thr
305                 310                 315                 320

Leu Ala Gln Met Thr Asp Lys Ala Ile Glu Leu Leu Ser Lys Asn Glu
                325                 330                 335

Lys Gly Phe Phe Leu Gln Val Glu Gly Ala Ser Ile Asp Lys Gln Asp
                340                 345                 350

His Ala Ala Asn Pro Cys Gly Gln Ile Gly Glu Thr Val Asp Leu Asp
            355                 360                 365

Glu Ala Val Gln Arg Ala Leu Glu Phe Ala Lys Lys Glu Gly Asn Thr
        370                 375                 380

Leu Val Ile Val Thr Ala Asp His Ala His Ala Ser Gln Ile Val Ala
385                 390                 395                 400

Pro Asp Thr Lys Ala Pro Gly Leu Thr Gln Ala Leu Asn Thr Lys Asp
                405                 410                 415

Gly Ala Val Met Val Met Ser Tyr Gly Asn Ser Glu Glu Asp Ser Gln
                420                 425                 430

Glu His Thr Gly Ser Gln Leu Arg Ile Ala Ala Tyr Gly Pro His Ala
            435                 440                 445

Ala Asn Val Val Gly Leu Thr Asp Gln Thr Asp Leu Phe Tyr Thr Met
450                 455                 460

Lys Ala Ala Leu Gly Leu Lys
465                 470

<210> SEQ ID NO 9
<211> LENGTH: 1024
<212> TYPE: PRT
<213> ORGANISM: Escherichia coli

<400> SEQUENCE: 9

Met Thr Met Ile Thr Asp Ser Leu Ala Val Val Leu Gln Arg Arg Asp

-continued

```
1               5                   10                  15
Trp Glu Asn Pro Gly Val Thr Gln Leu Asn Arg Leu Ala Ala His Pro
                20                  25                  30

Pro Phe Ala Ser Trp Arg Asn Ser Glu Glu Ala Arg Thr Asp Arg Pro
                35                  40                  45

Ser Gln Gln Leu Arg Ser Leu Asn Gly Glu Trp Arg Phe Ala Trp Phe
                50                  55                  60

Pro Ala Pro Glu Ala Val Pro Glu Ser Trp Leu Glu Cys Asp Leu Pro
65                  70                  75                  80

Glu Ala Asp Thr Val Val Pro Ser Asn Trp Gln Met His Gly Tyr
                85                  90                  95

Asp Ala Pro Ile Tyr Thr Asn Val Thr Tyr Pro Ile Thr Val Asn Pro
                100                 105                 110

Pro Phe Val Pro Thr Glu Asn Pro Thr Gly Cys Tyr Ser Leu Thr Phe
                115                 120                 125

Asn Val Asp Glu Ser Trp Leu Gln Glu Gly Gln Thr Arg Ile Ile Phe
                130                 135                 140

Asp Gly Val Asn Ser Ala Phe His Leu Trp Cys Asn Gly Arg Trp Val
145                 150                 155                 160

Gly Tyr Gly Gln Asp Ser Arg Leu Pro Ser Glu Phe Asp Leu Ser Ala
                165                 170                 175

Phe Leu Arg Ala Gly Glu Asn Arg Leu Ala Val Met Val Leu Arg Trp
                180                 185                 190

Ser Asp Gly Ser Tyr Leu Glu Asp Gln Asp Met Trp Arg Met Ser Gly
                195                 200                 205

Ile Phe Arg Asp Val Ser Leu Leu His Lys Pro Thr Thr Gln Ile Ser
                210                 215                 220

Asp Phe His Val Ala Thr Arg Phe Asn Asp Asp Phe Ser Arg Ala Val
225                 230                 235                 240

Leu Glu Ala Glu Val Gln Met Cys Gly Glu Leu Arg Asp Tyr Leu Arg
                245                 250                 255

Val Thr Val Ser Leu Trp Gln Gly Glu Thr Gln Val Ala Ser Gly Thr
                260                 265                 270

Ala Pro Phe Gly Gly Glu Ile Ile Asp Glu Arg Gly Gly Tyr Ala Asp
                275                 280                 285

Arg Val Thr Leu Arg Leu Asn Val Glu Asn Pro Lys Leu Trp Ser Ala
                290                 295                 300

Glu Ile Pro Asn Leu Tyr Arg Ala Val Val Glu Leu His Thr Ala Asp
305                 310                 315                 320

Gly Thr Leu Ile Glu Ala Glu Ala Cys Asp Val Gly Phe Arg Glu Val
                325                 330                 335

Arg Ile Glu Asn Gly Leu Leu Leu Leu Asn Gly Lys Pro Leu Leu Ile
                340                 345                 350

Arg Gly Val Asn Arg His Glu His His Pro Leu His Gly Gln Val Met
                355                 360                 365

Asp Glu Gln Thr Met Val Gln Asp Ile Leu Leu Met Lys Gln Asn Asn
                370                 375                 380

Phe Asn Ala Val Arg Cys Ser His Tyr Pro Asn His Pro Leu Trp Tyr
385                 390                 395                 400

Thr Leu Cys Asp Arg Tyr Gly Leu Tyr Val Val Asp Glu Ala Asn Ile
                405                 410                 415

Glu Thr His Gly Met Val Pro Met Asn Arg Leu Thr Asp Asp Pro Arg
                420                 425                 430
```

Trp Leu Pro Ala Met Ser Glu Arg Val Thr Arg Met Val Gln Arg Asp
         435                 440                 445

Arg Asn His Pro Ser Val Ile Ile Trp Ser Leu Gly Asn Glu Ser Gly
    450                 455                 460

His Gly Asn His Asp Ala Leu Tyr Arg Trp Ile Lys Ser Val Asp
465                 470                 475                 480

Pro Ser Arg Pro Val Gln Tyr Glu Gly Gly Ala Asp Thr Thr Ala
             485                 490                 495

Thr Asp Ile Ile Cys Pro Met Tyr Ala Arg Val Asp Glu Asp Gln Pro
             500                 505                 510

Phe Pro Ala Val Pro Lys Trp Ser Ile Lys Lys Trp Leu Ser Leu Pro
         515                 520                 525

Gly Glu Thr Arg Pro Leu Ile Leu Cys Glu Tyr Ala His Ala Met Gly
         530                 535                 540

Asn Ser Leu Gly Gly Phe Ala Lys Tyr Trp Gln Ala Phe Arg Gln Tyr
545                 550                 555                 560

Pro Arg Leu Gln Gly Gly Phe Val Trp Asp Trp Val Asp Gln Ser Leu
             565                 570                 575

Ile Lys Tyr Asp Glu Asn Gly Asn Pro Trp Ser Ala Tyr Gly Gly Asp
             580                 585                 590

Phe Gly Asp Thr Pro Asn Asp Arg Gln Phe Cys Met Asn Gly Leu Val
         595                 600                 605

Phe Ala Asp Arg Thr Pro His Pro Ala Leu Thr Glu Ala Lys His Gln
610                 615                 620

Gln Gln Phe Phe Gln Phe Arg Leu Ser Gly Gln Thr Ile Glu Val Thr
625                 630                 635                 640

Ser Glu Tyr Leu Phe Arg His Ser Asp Asn Glu Leu Leu His Trp Met
             645                 650                 655

Val Ala Leu Asp Gly Lys Pro Leu Ala Ser Gly Glu Val Pro Leu Asp
             660                 665                 670

Val Ala Pro Gln Gly Lys Gln Leu Ile Glu Leu Pro Glu Leu Pro Gln
         675                 680                 685

Pro Glu Ser Ala Gly Gln Leu Trp Leu Thr Val Arg Val Val Gln Pro
         690                 695                 700

Asn Ala Thr Ala Trp Ser Glu Ala Gly His Ile Ser Ala Trp Gln Gln
705                 710                 715                 720

Trp Arg Leu Ala Glu Asn Leu Ser Val Thr Leu Pro Ala Ala Ser His
             725                 730                 735

Ala Ile Pro His Leu Thr Thr Ser Glu Met Asp Phe Cys Ile Glu Leu
         740                 745                 750

Gly Asn Lys Arg Trp Gln Phe Asn Arg Gln Ser Gly Phe Leu Ser Gln
         755                 760                 765

Met Trp Ile Gly Asp Lys Lys Gln Leu Leu Thr Pro Leu Arg Asp Gln
770                 775                 780

Phe Thr Arg Ala Pro Leu Asp Asn Asp Ile Gly Val Ser Glu Ala Thr
785                 790                 795                 800

Arg Ile Asp Pro Asn Ala Trp Val Glu Arg Trp Lys Ala Ala Gly His
             805                 810                 815

Tyr Gln Ala Glu Ala Ala Leu Leu Gln Cys Thr Ala Asp Thr Leu Ala
         820                 825                 830

Asp Ala Val Leu Ile Thr Thr Ala His Ala Trp Gln His Gln Gly Lys
         835                 840                 845

-continued

```
Thr Leu Phe Ile Ser Arg Lys Thr Tyr Arg Ile Asp Gly Ser Gly Gln
    850             855             860

Met Ala Ile Thr Val Asp Val Glu Val Ala Ser Asp Thr Pro His Pro
865             870             875             880

Ala Arg Ile Gly Leu Asn Cys Gln Leu Ala Gln Val Ala Glu Arg Val
                885             890             895

Asn Trp Leu Gly Leu Gly Pro Gln Glu Asn Tyr Pro Asp Arg Leu Thr
            900             905             910

Ala Ala Cys Phe Asp Arg Trp Asp Leu Pro Leu Ser Asp Met Tyr Thr
        915             920             925

Pro Tyr Val Phe Pro Ser Glu Asn Gly Leu Arg Cys Gly Thr Arg Glu
    930             935             940

Leu Asn Tyr Gly Pro His Gln Trp Arg Gly Asp Phe Gln Phe Asn Ile
945             950             955             960

Ser Arg Tyr Ser Gln Gln Gln Leu Met Glu Thr Ser His Arg His Leu
                965             970             975

Leu His Ala Glu Glu Gly Thr Trp Leu Asn Ile Asp Gly Phe His Met
            980             985             990

Gly Ile Gly Gly Asp Asp Ser Trp  Ser Pro Ser Val Ser Ala Glu Phe
            995             1000            1005

Gln Leu Ser Ala Gly Arg Tyr  His Tyr Gln Leu Val  Trp Cys Gln
    1010            1015            1020

Lys
```

METHODS OF ATTACHING A MOLECULE-OF-INTEREST TO A MICROTUBE

RELATED APPLICATIONS

This application is a National Phase of PCT Patent Application No. PCT/IL2009/000171 having International filing date of Feb. 12, 2009, which claims the benefit of U.S. Provisional Patent Application Nos. 61/064,210, 61/064,206 and 61/064,204 filed on Feb. 21, 2008.

The teachings of PCT/IB2007/054001 are incorporated herein by reference.

The contents of all of the above documents are incorporated by reference as if fully set forth herein.

FIELD AND BACKGROUND OF THE INVENTION

The invention, in some embodiments thereof, relates to a method of attaching a molecule-of-interest to a microtube and, more particularly, but not exclusively, to electrospun microtubes including the molecule-of-interest attached thereto.

In nature there is an enormous variety of enzymes that catalyze reactions, some of which have industrial use. These include oxidoreductases, transferases, hydrolases, lyases, isomerases, and ligases. Immobilization of enzymes on solid substrates sometimes offers advantages over the use of a free enzyme. For example, immobilization can stabilize enzymes, enable better control of enzymatic reactions, allow the reuse of the enzyme and prevent enzyme loss with time. The material bearing the immobilized enzyme has a significant role in evoking these advantages both from architectural and chemical points of view.

Nanofibers and polymeric nanofibers in particular can be produced by an electrospinning process (Reneker D H., et al., 2006; Ramakrishna S., et al., 2005; Li D., et al., 2004; PCT WO 2006/106506 to the present inventors). Electrospun polymeric nanofibers have been widely used in biological applications such as scaffolds, carriers for biologically active molecules like proteins and enzymes (Xie J., et al., 2003; Zhang Y Z., et al., 2006; Jiang H., et al., 2006; and Patel A C., et al., 2006) and encapsulation of viruses and bacteria (Salalha W., et al., 2006).

Several approaches can be used to entrap or attach enzymes to electrospun fibers. One approach is to immobilize the enzyme on the outer surface of the nanofibers by either covalently attaching the desired enzyme to the functional groups of the polymer surface (Ye P., et al., 2006; Jia H., et al., 2002; Kim T G., et al., 2006) or physically absorbing the enzyme to the surface (Huang X J., et al., 2006). The second approach, which results in encapsulation of enzymes, is based on mixing the enzyme with the polymer solution prior to the electrospinning process (Xie J. and Hsieh Y-L, 2003). However, encapsulation is often associated with leaching of the enzymes, e.g., via fiber dissolution and burst releases (Zhang Y Z., et al., 2006), especially, when the host polymer is a water soluble polymer such as poly(vinyl alcohol) (PVA) or dextran. To prevent immediate dissolution of the fibers in a physiological environment (e.g., blood) and the subsequent enzyme leaching, the electrospun fibers can be crosslinked by chemical or physical agents such as glutaraldehyde or UV irradiation. Alternatively Zeng J, et al. (2005) suggested that PVA fibers can be coated with water insoluble polymers using a chemical vapor deposition (CVD). However, the organic solvents of the water insoluble polymers are harmful to biological material and can lead to loss of enzymatic activity. To overcome this problem, Herricks et al. (2005) suggested to use surfactant-stabilized enzymes in an organic solution of polystyrene (PS) as a spinning solution. In this way the electrospun nanofibers are insoluble in water and the enzymatic activity is retained due to surfactant stabilization (Herricks T E., et al., 2005).

Sun and co-workers (Sun Z, et al., 2003) describe the production of core-shell nanofibers (i.e., filled fibers) by co-electrospinning of two polymeric solutions using a two co-axial capillaries spinneret. US patent application No. 20060119015 to Wehrspohn R., et al. describes the production of hollow fibers by introducing a liquid containing a polymer to a porous template material, and removal of the template following polymer solidification. PCT/IB/2007/054001 to the present inventors (which is fully incorporated herein by reference) discloses methods of producing electrospun microtubes (i.e., hollow fibers) which can be further filled with liquids and be used as microfluidics.

SUMMARY OF THE INVENTION

According to an aspect of some embodiments of the present invention there is provided a method of attaching a molecule-of-interest to a microtube, the method comprising: co-electrospinning two polymeric solutions through co-axial capillaries, wherein a first polymeric solution of the two polymeric solutions is for forming a shell of the microtube and a second polymeric solution of the two polymeric solutions is for forming a coat over an internal surface of the shell, the first polymeric solution is selected solidifying faster than the second polymeric solution and a solvent of the second polymeric solution is selected incapable of dissolving the first polymeric solution and wherein the second polymeric solution comprises the molecule-of-interest, thereby attaching the molecule-of-interest to the microtube.

According to an aspect of some embodiments of the present invention there is provided a microtube comprising an electrospun shell, an electrospun coat over an internal surface of the shell and a molecule-of-interest attached to the microtube.

According to an aspect of some embodiments of the present invention there is provided a method of processing a substrate-of-interest, comprising contacting the substrate-of-interest with the microtube of the invention, wherein molecule-of-interest is capable of processing the substrate, thereby processing the substrate-of-interest.

According to an aspect of some embodiments of the present invention there is provided a method of depleting a molecule from a solution, comprising contacting the solution with the microtube of the invention, wherein the member of the affinity pair is selected capable of binding the molecule, thereby depleting the molecule from the solution.

According to an aspect of some embodiments of the present invention there is provided a method of isolating a molecule from a solution, comprising: (a) contacting the solution with the microtube of the invention under conditions which allow binding of the molecule to the microtube via the member of the affinity pair which is selected capable of binding the molecule, and; (b) eluting the molecule from the microtube; thereby isolating the molecule from the solution.

According to an aspect of some embodiments of the present invention there is provided a method of detecting a presence of a molecule in a sample, comprising: (a) contacting the sample with the microtube of the invention, wherein the member of the affinity pair is selected capable of binding the molecule, and; (b) detecting binding of the molecule by the member of the affinity pair; thereby detecting the presence of a molecule in the sample.

According to an aspect of some embodiments of the present invention there is provided a method of releasing a molecule-of-interest to cells of a subject in need thereof, comprising implanting in the subject the microtube of the invention, to thereby release the molecule-of-interest to cells of the subject.

According to some embodiments of the invention, the electrospun shell is formed of a first polymeric solution and the electrospun coat is formed of a second polymeric solution.

According to some embodiments of the invention, the first polymeric solution solidifies faster than the second polymeric solution.

According to some embodiments of the invention, a solvent of the second polymeric solution is incapable of dissolving the first polymeric solution.

According to some embodiments of the invention, the electrospun shell comprises a polymer selected from the group consisting of poly (e-caprolactone) (PCL), polyamide, poly(siloxane), poly(silicone), poly(ethylene), poly(vinyl pyrrolidone), poly(2-hydroxy ethylmethacrylate), poly(N-vinyl pyrrolidone), poly(methyl methacrylate), poly(vinyl alcohol), poly(acrylic acid), poly(vinyl acetate), polyacrylamide, poly(ethylene-co-vinyl acetate), poly(ethylene glycol), poly(methacrylic acid), polylactide, polyglycolide, poly(lactide-coglycolide), polyanhydride, polyorthoester, poly(carbonate), poly(acrylo nitrile), poly(ethylene oxide), polyaniline, polyvinyl carbazole, polystyrene, poly(vinyl phenol), polyhydroxyacid, poly(caprolactone), polyanhydride, polyhydroxyalkanoate, polyurethane, collagen, albumin, alginate, chitosan, starch, hyaluronic acid, and whereas the electrospun coat comprises a polymer selected from the group consisting of poly(acrylic acid), poly(vinyl acetate), polyacrylamide, poly(ethylene-co-vinyl acetate), poly(ethylene glycol), poly(methacrylic acid), polylactide polyglycolide, poly(lactide-coglycolide), polyanhydride, polyorthoester, poly(carbonate), poly(ethylene oxide), polyaniline, polyvinyl carbazole, polystyrene, poly(vinyl phenol), polyhydroxyacid, alginate, starch, hyaluronic acid.

According to some embodiments of the invention, a solvent of the first polymeric solution evaporates faster than a solvent of the second polymeric solution.

According to some embodiments of the invention, the electrospinning is effected using a rotating collector.

According to some embodiments of the invention, a solvent of the second polymeric solution is capable of evaporating through the internal surface of the shell.

According to some embodiments of the invention, the second polymeric solution is capable of wetting the internal surface of the shell.

According to some embodiments of the invention, a thickness of the shell is from about 100 nm to about 20 micrometer.

According to some embodiments of the invention, an internal diameter of the microtube is from about 50 nm to about 20 micrometer.

According to some embodiments of the invention, the first and the second polymeric solutions are selected from the group consisting of: 10% poly (e-caprolactone) (PCL) in chloroform ($CHCl_3$) and dimethylforamide (DMF) (80:20 by weight) as the first polymeric solution and 4% poly (ethylene oxide) (PEO) in water ($H_2O$) and ethanol (60:40 by weight) as the second polymeric solution, 10% PCL in $CHCl_3$ and DMF (80:20 by weight) as the first polymeric solution and 6% PEO in $H_2O$ and ethanol (60:40 by weight) as the second polymeric solution, 9% PCL in $CHCl_3$ and DMF (90:10 by weight) as the first polymeric solution and 7% PEO in $H_2O$ as the second polymeric solution, 10% PCL in $CHCl_3$ and DMF (80:20 by weight) as the first polymeric solution and 9% poly(vinyl alcohol) (PVA) in water and ethanol (50:50 by weight) as the second polymeric solution, and 10% PCL in $CHCl_3$ and DMF (90:10 by weight) as the first polymeric solution and 4% (w/w) PEO in ethanol:$H_2O$ (26:74 by weight) as a second polymeric solution.

According to some embodiments of the invention, the microtube is filled with a liquid.

According to some embodiments of the invention, the first and the second polymeric solutions are biocompatible.

According to some embodiments of the invention, the molecule-of-interest is attached to the coat over the internal surface of the shell.

According to some embodiments of the invention, the molecule-of-interest is attached to the shell of the microtube.

According to some embodiments of the invention, the molecule-of-interest comprises a polypeptide, a polynucleotide, a carbohydrate, a small molecule, or any combination thereof.

According to some embodiments of the invention, the molecule-of-interest comprises a member of an affinity pair.

According to some embodiments of the invention, the polypeptide is an enzyme.

According to some embodiments of the invention, the enzyme is alkaline phosphatase (SEQ ID NO:1 or 8) or beta-galactosidase (SEQ ID NO:2 or 9).

According to some embodiments of the invention, the first polymeric solution comprises polyethylene glycol (PEG).

According to some embodiments of the invention, the shell comprises pores.

According to some embodiments of the invention, the shell prevents diffusion of the molecule-of-interest therethrough.

According to some embodiments of the invention, the substrate-of-interest comprises incorporating the substrate-of-interest in a synthesis reaction catalyzed by the molecule-of-interest.

According to some embodiments of the invention, the substrate-of-interest comprises incorporating the substrate-of-interest in a catabolism reaction catalyzed by the molecule-of-interest.

According to some embodiments of the invention, the method further comprising collecting the solution following the contacting.

According to some embodiments of the invention, the solution comprises blood.

According to some embodiments of the invention, the affinity pair is selected from the group consisting of an enzyme and a substrate, a hormone and a receptor, an antibody and an antigen, a polypeptide and a polynucleotide, a polynucleotide and a cognate polynucleotide, a polypeptide and a metal ion, a polypeptide and a carbohydrate.

According to some embodiments of the invention, a therapeutically effective amount of the molecule-of-interest is capable of treating a pathology in the subject.

According to some embodiments of the invention, the molecule-of-interest comprises a polypeptide, and whereas a therapeutically effective amount of the polypeptide is capable of treating a pathology in the subject.

According to some embodiments of the invention, the pathology is selected from the group consisting of a metabolic disorder, an endocrine disease, an autoimmune disease, and cancer.

According to some embodiments of the invention, the polypeptide is selected from the group consisting of insulin (SEQ ID NO:6), phenylalanine hydroxylase (PAH) (SEQ ID NO:3), dystrophin (SEQ ID NO:4), beta-glucosidase (GBA) (SEQ ID NO:5), and ceruloplasmin ferroxidase (CP) (SEQ ID NO:7).

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

Figure 2A:
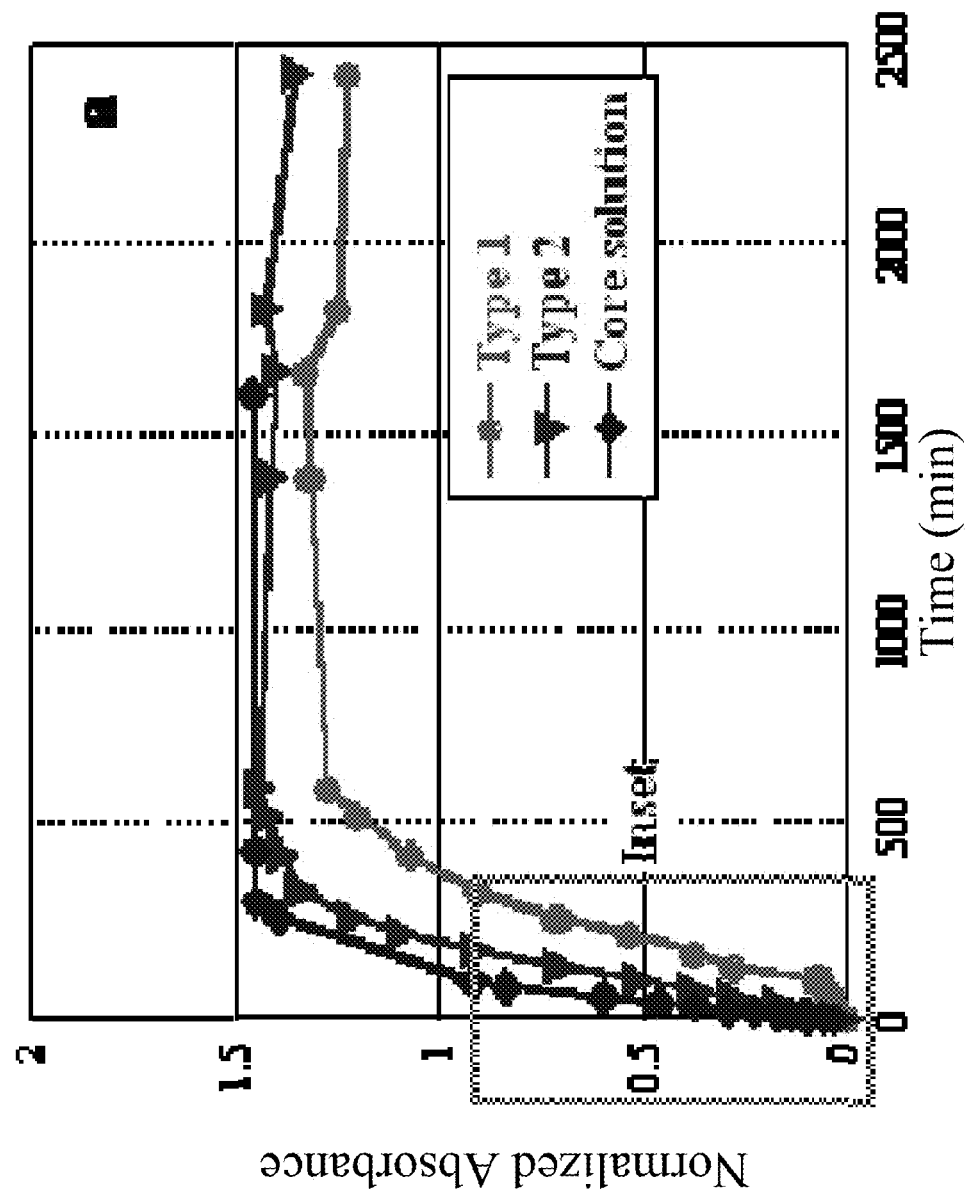
Figure 2B:
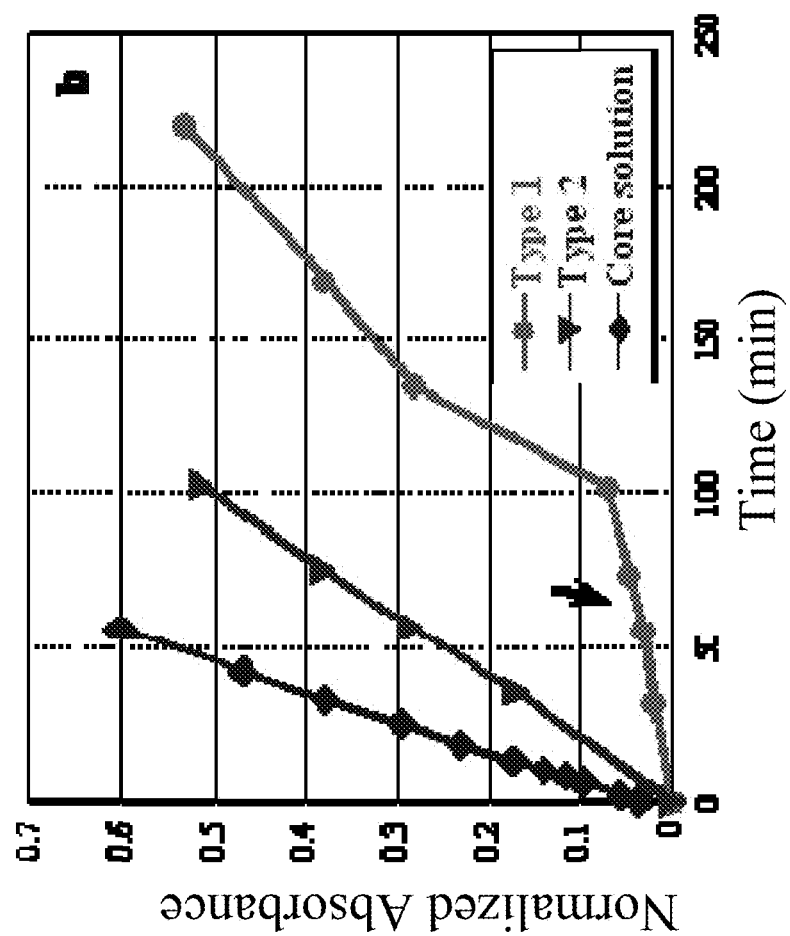
Figure 2C:
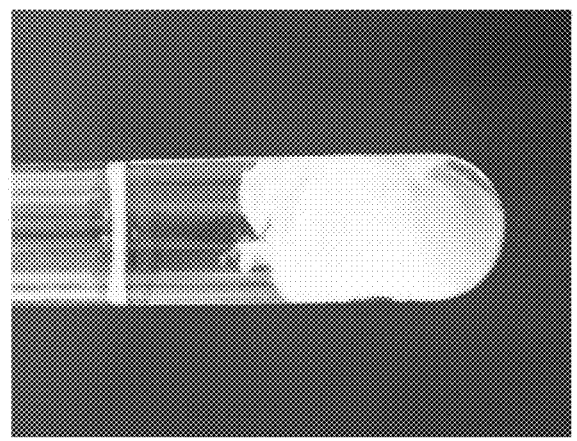
Figure 3:
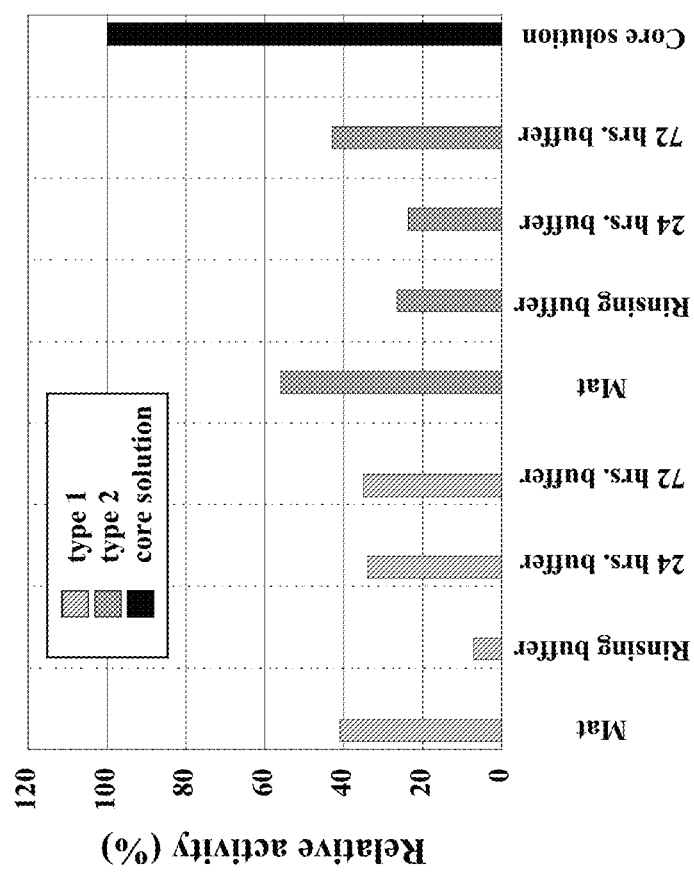

FIGS. 1A-D are images depicting high resolution scanning electron microscope (HRSEM) micrographs of (a) Type 1 fibers with alkaline phosphatase (AP); (b) Type 2 fibers with AP; (c) Type 1 fibers with beta-galactosidase (β-GAL); and (d) Type 2 fibers with β-GAL;

FIGS. 2A-C are graphs (FIGS. 2a-b) and a picture (FIG. 2C) depicting the progress of the AP reactions with time for enzymes attached to (e.g., encapsulated within) the electrospun fibers and the free enzyme in the solution forming the coat over the internal surface of the shell (also referred to herein as a core solution) prior to the electrospinning. FIG. 2A—the progress of the alkaline phosphatase reaction over 2500 minutes; FIG. 2B—inset, the progress of the reaction through over the first 300 minutes; Note that the enzymatic reaction of the enzyme encapsulated within type 2 electrospun microtubes is faster than that of enzyme encapsulated within type 1 electrospun microtubes. FIG. 2C—a photograph of a piece of mat (Type 1) immersed in the assay solution. The presence of the yellow reaction product, p-nitrophenol, is apparent; the reaction substrate was para-nitrophenyl phosphate;

FIG. 3 is a histogram depicting the relative activity of AP enzyme for different types of fibers (type 1 and type 2) and in dwelling buffers. Mat=the electrospun fibers (microtubes) with the attached (encapsulated) enzymes; rinsing buffer=the buffer used to only rinse the fibers, without any additional incubation time; 24 hrs. buffer=the buffer following incubation of the fibers therein for 24 hours; 72 hrs. buffer=the buffer following incubation of the fibers therein for 72 hours; core solution=the enzyme in the core solution prior to the electrospinning process.

Figure 4B:
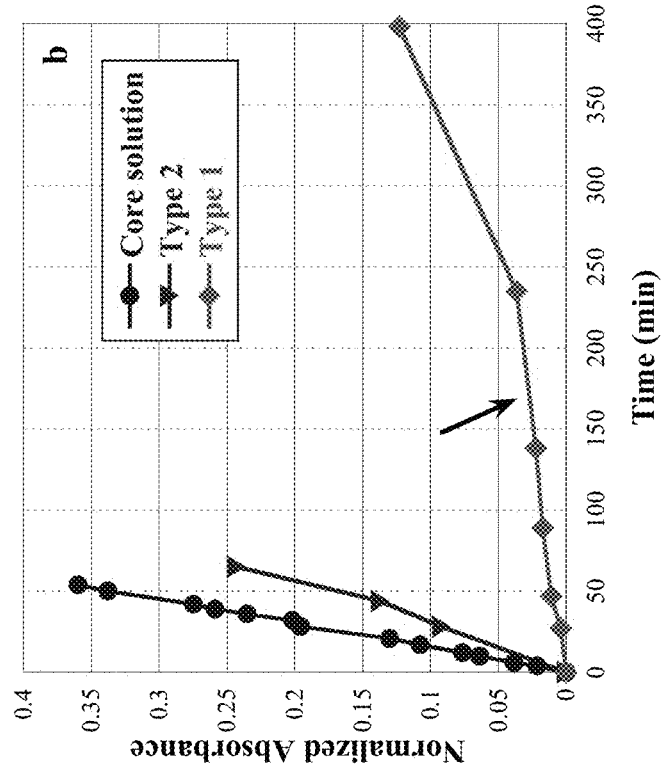
Figure 4A:
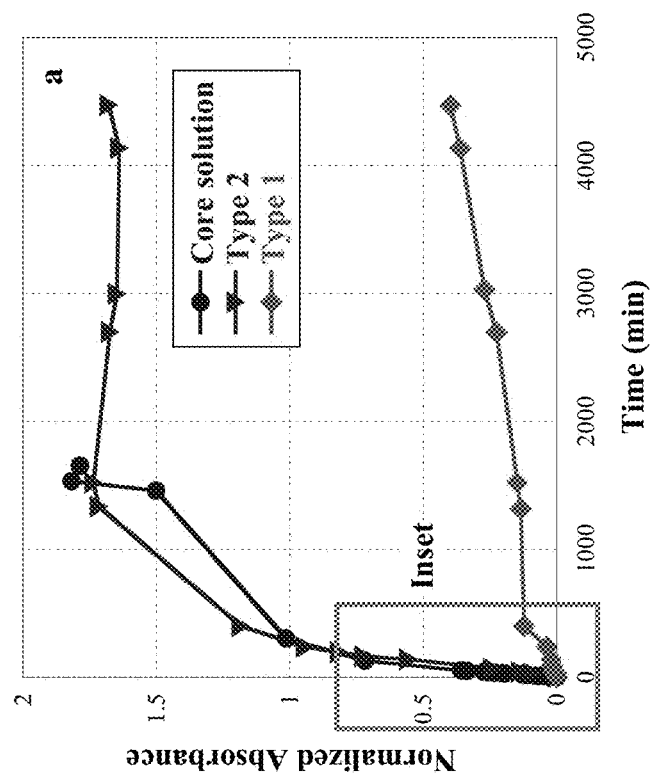
Figure 5:
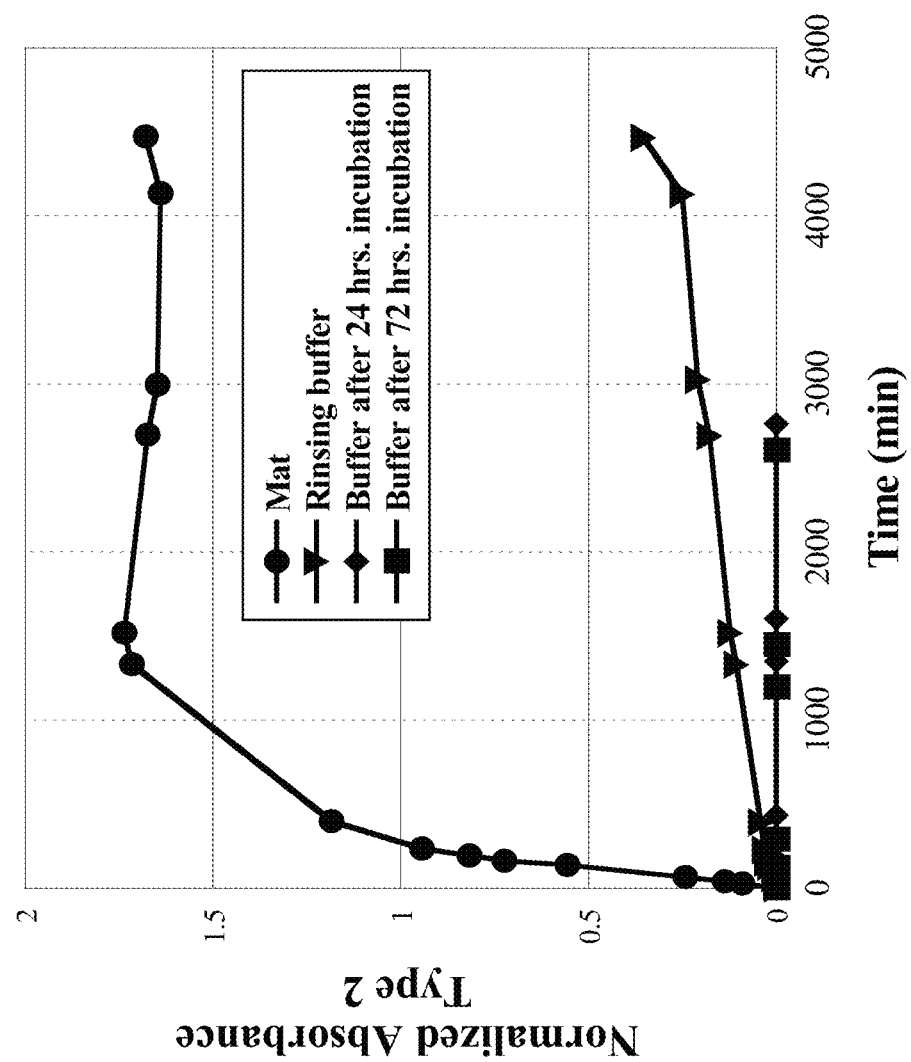
Figure 6:
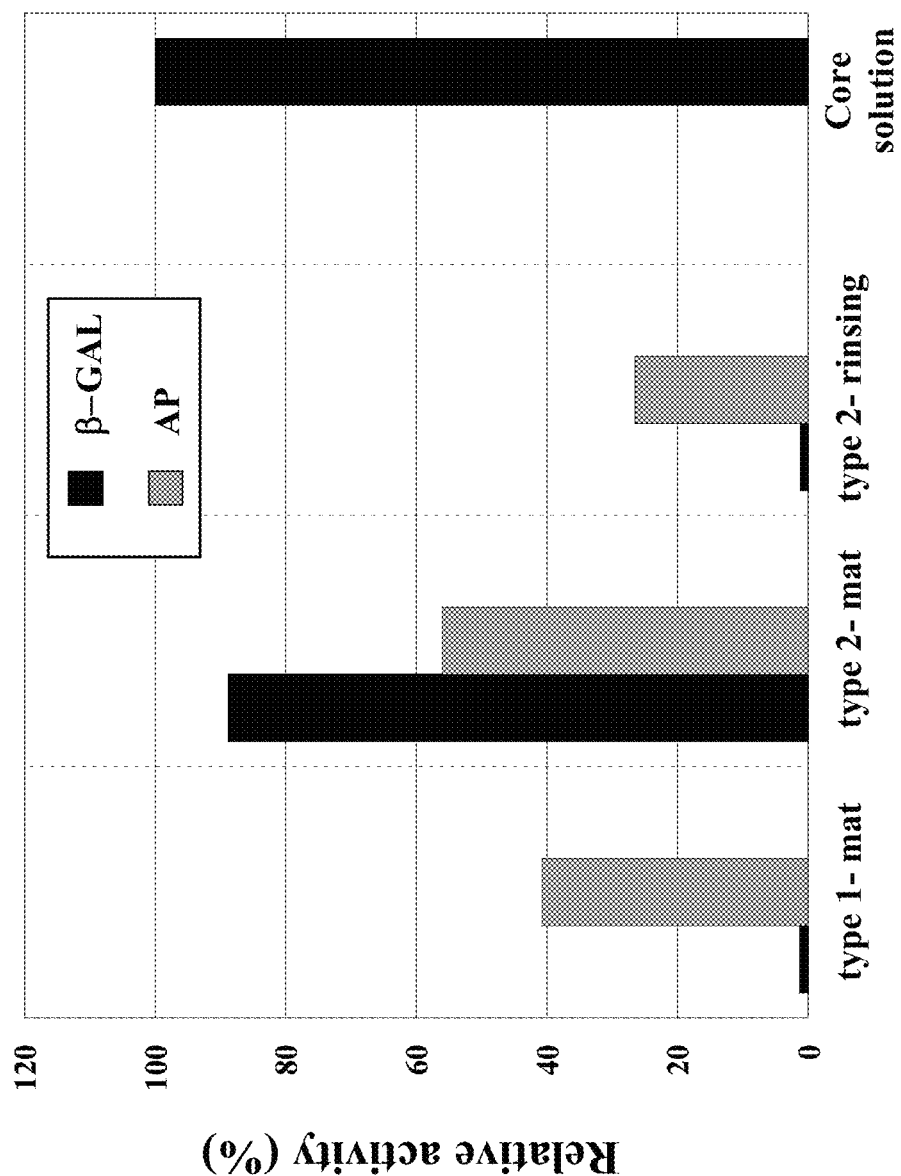
Figure 7A:
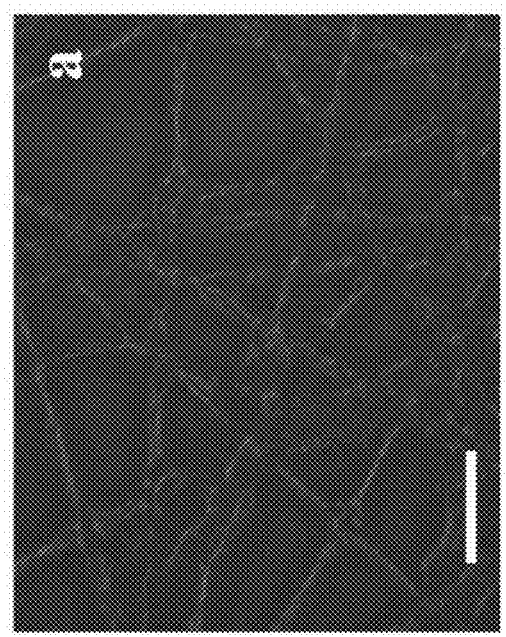
Figure 7B:
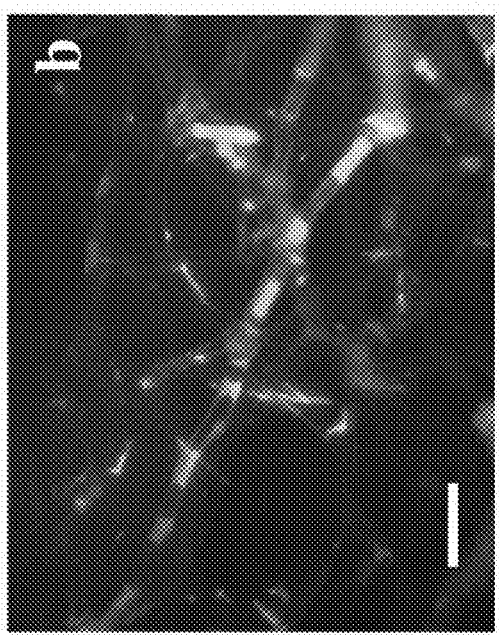

FIGS. 4A-B are graphs depicting the progress of the β-GAL reactions with time for the two types of electrospun fibers and the free enzyme in the core solution. The substrate was ortho-nitrophenyl galactoside. FIG. 4A—the progress of the β-GAL reactions over 5000 minutes as measured by the amount of ortho-nitrophenol generated; FIG. 4B—inset of the graph of FIG. 4a, the progress of the β-GAL reactions over the first 50 minutes;

FIG. 5 is a graph depicting the β-GAL reaction versus time for the mat and buffers for Type 2 fibers;

FIG. 6 is a histogram depicting the relative activity of the β-GAL and AP for different types of fibers;

FIGS. 7A-B are fluorescence microscope micrographs depicting Type 1 fibers with AP (FIG. 7A) and β-GAL (FIG. 7B). Size bars: 100 μm (FIG. 7A) and 50 μm (FIG. 7B).

Figure 8:
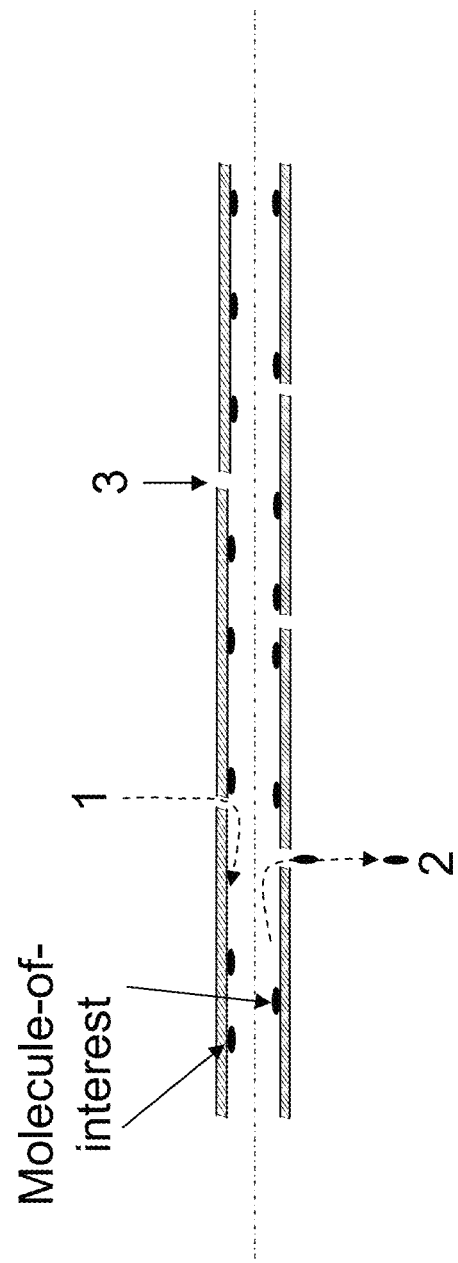

FIG. 8 is a schematic illustration depicting the desorption process of the molecule-of-interest from the microtube of the invention. The molecule-of-interest (e.g., a protein, an enzyme) is attached to the coat over the internal surface of the shell. Following contacting the microtube with a solution, the solution enters the microtube via the pores (an exemplary pore is marked by arrow No. 3) by a capillary rise (see arrow No. 1) and gradually wets and fills the microtube inner volume. The desorption of the molecule-of-interest from the internal surface of the microtube shell (which depends mainly on the rate of the release of the molecule-of-interest from the polymer) is shown by arrow No. 2.

Figure 9:
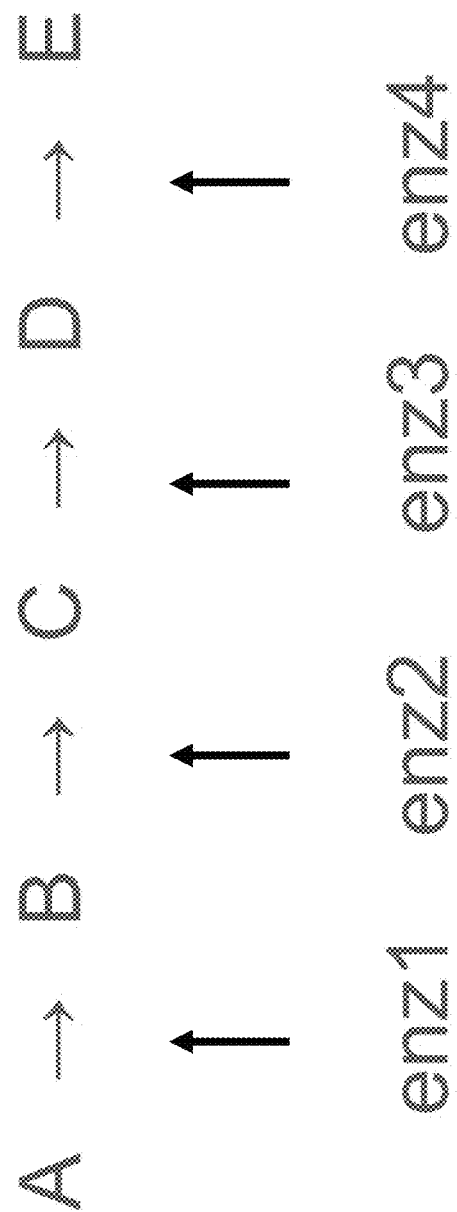

FIG. 9 depicts a multi-step enzymatic reaction performed using encapsulated molecules-of-interest (enzymes 1-4). Enzyme 1 (enz1) catalyzes the conversion of compound A to B; Enzyme 2 (enz2) catalyzes the conversion of compound B to C; Enzyme 3 (enz3) catalyzes the conversion of compound C to D; Enzyme 4 (enz4) catalyzes the conversion of compound D to E.

FIG. 10 is a schematic presentation depicting Atrazine degradation by the isolated *Pseudomonas* ADP enzymes: AtzA (atrazine chlorohydrolase, e.g., GenBank Accession No. NP_862474), AtzB (hydroxyatrazine hydrolase, e.g., GenBank Accession No. NP_862481), AtzC(N-isopropylammelide isopropylamino hydrolase, e.g., GenBank Accession No. NP_862508), AtzD (cyanuric acid amidohydrolase, e.g., GenBank Accession No. NP_862537), AtzE (biuret hydrolase, e.g., GenBank Accession No. NP_862538) and AtzF (allophanate hydrolase, e.g., GenBank Accession No. AAK50333) which are attached to the microtube of the invention.

DESCRIPTION OF SPECIFIC EMBODIMENTS OF THE INVENTION

The present invention, in some embodiments thereof, relates to methods of attaching a molecule-of-interest to a microtube and, more particularly, but not exclusively, to electrospun microtubes which include a molecule-of-interest attached thereto which can be used in various therapeutic, diagnostic, purification and synthesis applications.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

While reducing the invention to practice, the present inventors have uncovered that a molecule-of-interest can be attached to electrospun microtubes. Thus, as is shown in FIGS. 1a-b and described in Example 1 of the Examples section which follows, two types of electrospun microtubes containing active molecules-of-interest (e.g., enzymes such as alkaline phosphatase or beta-galactosidase) were formed: Type 1 microtubes which exhibit a non-porous shell, and Type 2 microtubes which exhibit a porous shell due to the presence of PEG in the polymeric solution forming the shell. The enzymatic activity contained within the microtubes was at the same order of magnitude as that of the polymeric solution prior to the electrospinning process (FIGS. 2a-b, 3,4a-b and 6; Examples 1-3 of the Examples section which follows) indicating that surprisingly the process of production did not compromise the functionality of the delicate protein material incorporated into the tube. In addition, as is shown in FIG. 3 and described in Example 2 of the Examples section which follows, both the porous and non-porous microtubes were capable of releasing enzymes attached thereto. Moreover, during the electrospinning process, some of the alkaline phosphatase enzyme migrated to the outer surface of the microtube shell and was released therefrom into the aqueous environment (FIG. 3, Example 2), while the β-GAL enzyme remained within the internal surface of the shell (FIG. 5, Example 3). In addition, as is further described in Example 3 of the Examples section which follows, the activity of the enzymes attached to the internal surface of the shell was increased in the presence of a porous shell which enabled the passage of substrates therethrough (FIGS. 4a-b). These results support the use of the microtubes of the invention as micro-reactors (e.g., bioreactors) for various synthesis, hydrolysis, isolation and purification reactions.

According to an aspect of the invention there is provided a method of attaching a molecule-of-interest to a microtube. The method is effected by co-electrospinning two polymeric solutions through co-axial capillaries, wherein a first polymeric solution of the two polymeric solutions is for forming a shell of the microtube and a second polymeric solution of the two polymeric solutions is for forming a coat over an internal surface of the shell, the first polymeric solution is selected solidifying faster than the second polymeric solution and a solvent of the second polymeric solution is selected incapable of dissolving the first polymeric solution and wherein the second polymeric solution comprises the molecule-of-interest, thereby attaching the molecule-of-interest to the microtube.

As used herein the term "microtube" refers to a hollow tube having an inner diameter of e.g., about 200 nm to about 50 µm and an outer diameter of e.g., about 0.5 µm to about 100 µm.

According to some embodiments of the invention the thickness of the microtube shell can vary from a few nanometers to several micrometers, such as from about 100 nm to about 20 µm, e.g., from about 200 nm to about 10 µm, from about 100 nm to about 5 µm, from about 100 nm to about 1 µm, e.g., about 500 nm.

According to some embodiments of the invention the internal diameter of the microtube shell can vary from a few nanometers to several micrometers, such as from about 50 nm to about 50 µm, e.g., from about 100 nm to about 20 µm, from about 200 nm to about 10 µm, from about 500 nm to about 5 µm, from about 1 µm to about 5 µm, e.g., about 3 µm.

According to some embodiments of the invention, the microtube may have a length which is from about 0.1 millimeter (mm) to about 20 centimeter (cm), e.g., from about 1-20 cm, e.g., about 5-10 cm.

As used herein the term "attaching" refers to the binding of the molecule-of-interest to the polymer(s) comprised in the microtube of the invention via covalent or non-covalent binding (e.g., via an electrostatic bond, a hydrogen bond, a van-Der Waals interaction) so as to obtain an absorbed, embedded or immobilized molecule-of-interest to the microtube of the invention.

According to some embodiments of the invention, the length (L) of the microtube can be several orders of magnitude higher (e.g., 10 times, 100 times, 1000 times, 10,000 times) than the microtube's diameter (D). Accordingly, a molecule-of-interest which is attached to such a microtube is referred to as being entrapped or encapsulated within the microtube.

According to some embodiments of the invention, covalent attachment of the molecule-of-interest can be via functional groups such as SH groups, amino groups, carboxyl groups which are added to the polymer(s) forming the microtube.

As used herein the phrase "co-electrospinning" refers to a process in which at least two polymeric solutions are electrospun from co-axial capillaries (i.e., at least two capillary dispensers wherein one capillary is placed within the other capillary while sharing a co-axial orientation) forming the spinneret within an electrostatic field in a direction of a collector. The capillary can be, for example, a syringe with a metal needle or a bath provided with one or more capillary apertures from which the polymeric solution can be extruded, e.g., under the action of hydrostatic pressure, mechanical pressure, air pressure and/or high voltage.

The collector serves for collecting the electrospun element (e.g., the electrospun microtube) thereupon. Such a collector can be a rotating collector or a static (non rotating) collector. When a rotating collector is used, such a collector may have a cylindrical shape (e.g., a drum), however, the rotating collector can be also of a planar geometry (e.g., an horizontal disk). The spinneret is typically connected to a source of high voltage, such as of positive polarity, while the collector is grounded, thus forming an electrostatic field between the dispensing capillary (dispenser) and the collector. Alternatively, the spinneret can be grounded while the collector is connected to a source of high voltage, such as with negative polarity. As will be appreciated by one ordinarily skilled in the art, any of the above configurations establishes motion of a positively charged jet from the spinneret to the collector. Reverse polarity for establishing motions of a negatively charged jet from the spinneret to the collector are also contemplated.

For electrospinning, the first polymeric solution is injected into the outer capillary of the co-axial capillaries while the second polymeric solution is injected into the inner capillary of the co-axial capillaries. In order to form a microtube (i.e., a hollow structure, as mentioned above), the first polymeric solution (which is for forming the shell of the microtube) solidifies faster than the second polymeric solution (also referred herein as a core polymeric solution, and is for forming a coat over the internal surface of the shell). In addition, the formation of a microtube also requires that the solvent of the second polymeric solution be incapable of dissolving the first polymeric solution.

The solidification rates of the first and second polymeric solutions are critical for forming the microtube. For example, for a microtube of about 100 µm, the solidification of the first polymer (of the first polymeric solution) can be within about 30 milliseconds (ms) while the solidification of the second polymer (of the second polymeric solution) can be within about 10-20 seconds. The solidification may be a result of polymerization rate and/or evaporation rate.

According to some embodiments of the invention, the solvent of the first polymeric solution evaporates faster than the solvent of second polymeric solution (e.g., the solvent of the first polymeric solution exhibits a higher vapor pressure than the solvent of the second polymeric solution).

According to some embodiments of the invention, the rate of evaporation of the solvent of the first polymeric solution is at least about 10 times faster than that of the solvent of the second polymeric solution. The evaporation rate of the solvent of the first polymeric solution can be at least about 100 times faster or at least about 1000 times faster than the evaporation rate of the solvent of second polymeric solution. For example, the evaporation of chloroform is significantly faster than the evaporation of an aqueous solution (water) due to the high vapor pressure at room temperature of the chloroform (195 mmHg) vs. that of the aqueous solution (23.8 mmHg).

When selecting a solvent of the second polymeric solution which is incapable of dissolving the first polymeric solution (i.e., a non-solvent of the first polymeric solution), the polymer of the first polymeric solution can solidify (e.g., through precipitation) and form a strong microtube shell which does not collapse, and is characterized by an even thickness. According to some embodiments of the invention, the first polymeric solution (e.g., the solvent of the first polymer) is substantially immiscible in the solvent of the second polymeric solution.

The solvent of the second polymeric solution may evaporate while the polymer (of the second polymeric solution) forms a thin layer on the internal surface of the shell.

According to some embodiments of the invention, the solvent of the second polymeric solution is capable of evaporating through the internal surface of the shell.

The flow rates of the first and second polymeric solutions can determine the microtube outer and inner diameter and thickness of shell. Non-limiting examples of microtubes generated by electrospinning using different flow rates are shown in Table 1 hereinbelow.

TABLE 1

Effect of the flow rates of the two polymeric solutions during electrospinning on microtube diameter and thickness of shell

| System No. | System: First polymeric solution/ Second polymeric solution | Flow rates (ml/hr) | R Outer Fiber radius (μm) | d Shell thickness (μm) | V Voltage (kV) | Electro-static field kV/cm |
|---|---|---|---|---|---|---|
| M5 | First polymeric solution | 4 | 3.0-4.5 | 0.5 ± 0.1 | 8.5 | 0.43 |
|  | Second polymeric solution | 0.5 |  |  |  |  |
| M10 | First polymeric solution | 10 | 2.3-4.0 | 1.0 ± 0.1 | 8 | 0.5 |
|  | Second polymeric solution | 0.3 |  |  |  |  |
| M11 | First polymeric solution | 10 | 3-6 | 1.0 ± 0.1 | 9 | 0.56 |
|  | Second polymeric solution | 2 |  |  |  |  |

Table 1: Electrospinning was performed with the following solutions: First polymeric solution (for forming the shell) was 10% PCL in CHCl$_3$/DMF (8:2 weight/weight); Second polymeric solution (for forming the coat) was 4% PEO in H$_2$O/EtOH (6:4, weight/weight). PCL used was PCL 80 K; PEO used was PEO 600 K. The temperature during electrospinning was 22-26° C. The relative humidity during electrospinning was 58%, 52% and 53% for systems M5, M10 and M11, respectively. The flow rates were measured in milliliter per hour (ml/hr); the outer microtube radius (R) and the shell thickness (d) were measured in microns (μm). The voltage was measured in kilo volt (kV), and the electrostatic field was measured in kV per centimeter (cm). The resulting tubes were hollow (good tubes in systems M5 and M11, and mostly good in system M10).

As used herein the phrase "polymeric solution" refers to a soluble polymer, i.e., a liquid medium containing one or more polymers, co-polymers or blends of polymers dissolved in a solvent. The polymer used by the invention can be a natural, synthetic, biocompatible and/or biodegradable polymer.

The phrase "synthetic polymer" refers to polymers that are not found in nature, even if the polymers are made from naturally occurring biomaterials. Examples include, but are not limited to, aliphatic polyesters, poly(amino acids), copoly(ether-esters), polyalkylenes oxalates, polyamides, tyrosine derived polycarbonates, poly(iminocarbonates), polyorthoesters, polyoxaesters, polyamidoesters, polyoxaesters containing amine groups, poly(anhydrides), polyphosphazenes, and combinations thereof.

Suitable synthetic polymers for use by the invention can also include biosynthetic polymers based on sequences found in naturally occurring proteins such as those of collagen, elastin, thrombin, fibronectin, or derivatives thereof or, starches, poly(amino acids), poly(propylene fumarate), gelatin, alginate, pectin, fibrin, oxidized cellulose, chitin, chitosan, tropoelastin, hyaluronic acid, polyethylene, polyethylene terephthalate, poly(tetrafluoroethylene), polycarbonate, polypropylene and poly(vinyl alcohol), ribonucleic acids, deoxyribonucleic acids, polypeptides, proteins, polysaccharides, polynucleotides and combinations thereof.

The phrase "natural polymer" refers to polymers that are naturally occurring. Non-limiting examples of such polymers include, silk, collagen-based materials, chitosan, hyaluronic acid, albumin, fibrinogen, and alginate.

As used herein, the phrase "co-polymer" refers to a polymer of at least two chemically distinct monomers. Non-limiting examples of co-polymers include, polylactic acid (PLA)-polyethyleneglycol (PEG), polyethylene glycol terephthalate (PEGT)/polybutylene terephthalate (PBT), PLA-polyglycolic acid (PGA), PEG-polycaprolactone (PCL) and PCL-PLA.

As used herein, the phrase "blends of polymers" refers to the result of mixing two or more polymers together to create a new material with different physical properties.

The phrase "biocompatible polymer" refers to any polymer (synthetic or natural) which when in contact with cells, tissues or body fluid of an organism does not induce adverse effects such as immunological reactions and/or rejections, cellular death and the like. It will be appreciated that a biocompatible polymer can also be a biodegradable polymer.

According to some embodiments of the invention, the first and the second polymeric solutions are biocompatible.

Non-limiting examples of biocompatible polymers include polyesters (PE), PCL, Calcium sulfate, PLA, PGA, PEG, polyvinyl alcohol, polyvinyl pyrrolidone, Polytetrafluoroethylene (PTFE, teflon), polypropylene (PP), polyvinylchloride (PVC), Polymethylmethacrylate (PMMA), polyamides, segmented polyurethane, polycarbonate-urethane and thermoplastic polyether urethane, silicone-polyether-urethane, silicone-polycarbonate-urethane collagen, PEG-DMA, alginate, hydroxyapatite and chitosan, blends and copolymers thereof.

The phrase "biodegradable polymer" refers to a synthetic or natural polymer which can be degraded (i.e., broken down) in the physiological environment such as by proteases or other enzymes produced by living organisms such as bacteria, fungi, plants and animals. Biodegradability depends on the availability of degradation substrates (i.e., biological materials or portion thereof which are part of the polymer), the presence of biodegrading materials (e.g., microorganisms, enzymes, proteins) and the availability of oxygen (for aerobic organisms, microorganisms or portions thereof), lack of oxygen (for anaerobic organisms, microorganisms or portions thereof) and/or other nutrients. Examples of biodegradable polymers/materials include, but are not limited to, collagen (e.g., Collagen I or IV), fibrin, hyaluronic acid, polylactic acid (PLA), polyglycolic acid (PGA), polycaprolactone (PCL), polydioxanone (PDO), trimethylene carbonate (TMC), polyethyleneglycol (PEG), collagen, PEG-DMA, alginate, chitosan copolymers or mixtures thereof.

According to some embodiments, the polymeric solution can be made of one or more polymers, each can be a polymer or a co-polymer such as described hereinabove.

According to some embodiments of the invention, the polymeric solution of the invention is a mixture of at least one biocompatible polymer and a co-polymer (either biodegradable or non-biodegradable).

According to some embodiments of the invention, the first polymeric solution for forming the shell can be made of a polymer such as poly (e-caprolactone) (PCL), polyamide, poly(siloxane), poly(silicone), poly(ethylene), poly(vinyl pyrrolidone), poly(2-hydroxy ethylmethacrylate), poly(N-vinyl pyrrolidone), poly(methyl methacrylate), poly(vinyl alcohol), poly(acrylic acid), poly(vinyl acetate), polyacrylamide, poly(ethylene-co-vinyl acetate), poly(ethylene glycol), poly(methacrylic acid), polylactide, polyglycolide, poly(lactide-coglycolide), polyanhydride, polyorthoester, poly(carbonate), poly(acrylo nitrile), poly(ethylene oxide), polyaniline, polyvinyl carbazole, polystyrene, poly(vinyl phenol), polyhydroxyacid, poly(caprolactone), polyanhydride, polyhydroxyalkanoate, polyurethane, collagen, albumin, alginate, chitosan, starch, hyaluronic acid, and blends and copolymers thereof.

According to some embodiments of the invention, the second polymeric solution for forming the coat over the internal surface of the shell can be made of a polymer such as poly(acrylic acid), poly(vinyl acetate), polyacrylamide, poly(ethylene-co-vinyl acetate), poly(ethylene glycol), poly(methacrylic acid), polylactide, polyglycolide, poly(lactide-coglycolide), polyanhydride, polyorthoester, poly(carbonate), poly(ethylene oxide), polyaniline, polyvinyl carbazole, polystyrene, poly(vinyl phenol), polyhydroxyacid, alginate, starch, hyaluronic acid, and blends and copolymers thereof.

During the formation of the microtube shell (e.g., following the solidification of the first polymeric solution) the second polymeric solution flows within the internal surface of the shell.

According to some embodiments of the invention, the second polymeric solution is selected capable of wetting the internal surface of the shell.

Various polymeric solutions which are known in the art as capable of wetting other polymeric surfaces (for forming the shell) can be used. Following is a non-limiting list of pairs of polymeric solutions in which the second polymeric solution is capable of wetting the internal surface of the shell formed by the first polymeric solution.

TABLE 2

Pairs of polymeric solutions for producing the microtube of the invention

| First polymeric solution forming the shell | Second polymeric solution capable of wetting the internal surface of the shell |
|---|---|
| 10% poly (e-caprolactone) (PCL); in chloroform (CHCl$_3$) and dimethylforamide (DMF) (80:20 by weight) | 4% poly(ethylene oxide) (PEO); in water (H$_2$O) and ethanol (60:40 by weight) |
| Nylon 6,6 in formic acid 7 to 12 wt % | 4% poly(ethylene oxide) (PEO); in water (H$_2$O) and ethanol (60:40 by weight) |
| Poly(L-lactide-co-glycolide) (PLGA 10:90) in hexafluroisopropanol (HFIP) concentrations ranging from 2 to 7 weight % solution. | 4% poly(ethylene oxide) (PEO) in water (H$_2$O) and ethanol (60:40 by weight) |
| Poly(L-lactide-co-glycolide) (PLGA 15:85) hexafluroisopropanol (HFIP) concentrations ranging from 2 to 7 weight % solution. | 4% poly(ethylene oxide) (PEO); in water (H$_2$O) and ethanol (60:40 by weight) |
| poly(lactide-co-glycolide) (PLGA; l-lactide/glycolide _ 50/50) 1,1,1,3,3,3-hexafluoro-2-propanol (HFIP) concentrations ranging from 2 to 7 weight % solution. | 4% poly(ethylene oxide) (PEO); in water (H$_2$O) and ethanol (60:40 by weight) |
| polyglycolide (PGA) in chloroform 3-10 weight % solution. | 9% poly(vinyl alcohol) (PVA); in water and ethanol (50:50 by weight) |
| poly(L-lactide) (PLA) in chloroform 3-10 weight % solution. | 9% poly(vinyl alcohol) (PVA); in water and ethanol (50:50 by weight) |

TABLE 2-continued

Pairs of polymeric solutions for producing the microtube of the invention

| First polymeric solution forming the shell | Second polymeric solution capable of wetting the internal surface of the shell |
|---|---|
| Segmented polyurethane in DMF and THF (80:20 by weight) | 9% poly(vinyl alcohol) (PVA); in water and ethanol (50:50 by weight) |
| Polyurethane in DMF and tetrahydrofuran, THF (80:20 by weight) | 9% poly(vinyl alcohol) (PVA); in water and ethanol (50:50 by weight) |
| PLGA (poly lactic-co-glycolic acid); in chloroform and DMSO (dimethyl sulfoxide) in chloroform and DMSO (80:20 by weight). | 9% poly(vinyl alcohol) (PVA); in water and ethanol (50:50 by weight) |
| 10% PCL in $CHCl_3$/DMF (80:20 by weight) | 6% PEO in $H_2O$/EtOH (60:40 by weight) |
| 9% PCL in $CHCl_3$/DMSO (90:10 by weight) | 7% PEO in $H_2O$ |
| 10% PCL in $CHCl_3$/DMF (80:20 by weight) | 9% PVA in ethanol/water (50:50 by weight) |
| 10% PCL 80 K $CHCl_3$:DMF (90:10 by weight) | 4% (w/w) PEO 600 K; in ethanol:$H_2O$ (26:74 by weight) |
| 10% PCL 80 K + 1% PEG 6 K $CHCl_3$:DMF (90:10 by weight) | 4% (w/w) PEO 600 K; in ethanol:$H_2O$ (26:74 by weight) |

Table 2 (cont.). The polymers forming the solutions and the solvents are provided by weight ratios, i.e., a weight/weight (w/w) ratio.

According to some embodiments of the invention, the first and the second polymeric solutions are selected from the group consisting of: 10% poly (e-caprolactone) (PCL) in chloroform ($CHCl_3$) and dimethylforamide (DMF) (80:20 by weight) as the first polymeric solution and 4% poly (ethylene oxide) (PEO) in water ($H_2O$) and ethanol (60:40 by weight) as the second polymeric solution, 10% PCL in $CHCl_3$ and DMF (80:20 by weight) as the first polymeric solution and 6% PEO in water and ethanol (60:40 by weight) as the second polymeric solution, 9% PCL in $CHCl_3$ and DMF (90:10 by weight) as the first polymeric solution and 7% PEO in water as the second polymeric solution, 10% PCL in $CHCl_3$ and DMF (80:20 by weight) as the first polymeric solution and 9% poly(vinyl alcohol) (PVA) in water and ethanol (50:50 by weight) as the second polymeric solution and 10% PCL in $CHCl_3$ and DMF (90:10 by weight) as the first polymeric solution and 4% (w/w) PEO in ethanol:$H_2O$ (26:74 by weight) as a second polymeric solution.

To enable a flow of a liquid-of-interest within the microtube, i.e., along the coat polymer covering the internal surface of the shell (which originates from the second polymer solution), the surface (thin film) formed by the coat polymer should be designed such that it can be wetted by the liquid-of-interest. The ability to wet (wettability) polymer films by liquids is known in the art. For example, silicone oil or water can wet a surface made of a PEO polymer. It will be appreciated that the wettability of the coat polymer covering the internal surface of the shell can be controlled (e.g., improved) for example by attaching functional groups such as hydroxyl groups (OH) which increase the hydrophilicity of the coat by a plasma treatment [see Thurston R M, Clay J D, Schulte M D, Effect of atmospheric plasma treatment on polymer surface energy and adhesion, Journal of Plastic Film & Sheeting 23 (1): 63-78 January 2007; which is incorporated within by reference].

As is further discussed hereinabove and in the Examples section which follows, for certain applications the microtube shell may comprise pores, thus creating a "breathing" tube. Methods of forming "breathing" microtube (i.e., microtubes with pores in the shell thereof) are described in PCT/IB2007/054001 to the present inventors, which is fully incorporated herein by reference. Briefly, "breathing" tubes can be formed by the inclusion of a high percent (e.g., at least 80%) of a volatile component such as tetrahydrofuran (THF), chloroform, acetone, or trifluoroethanol (TFE) in the first polymeric solution forming the shell, and/or by the inclusion of a water-soluble polymer such as polyethylene glycol (PEG) in the first polymeric solution forming the shell so that the first polymeric solution comprises a blend of polymers in which one is water-soluble and the other is water-insoluble (e.g., a blend of PEG and PCL). Alternatively, "breathing" microtubes can be formed by inducing pores in the shell after the completion of the electrospinning process, essentially as described in PCT WO 2006/106506 to the present inventors, which is fully incorporated herein by reference, such as by passing an electrical spark or a heated puncturing element through the electrospun shell, or by using a pulsed or continuous laser beam through the electrospun shell.

According to some embodiments of the invention, the first polymeric solution comprises PEG for inducing pores in the shell. For example, to generate pores greater (>) than 150 nm in diameter, the first polymeric solution may include about 4% PEG MW 35 kDa. Similarly, to generate pores smaller (<) than 150 nm in diameter, the first polymeric solution may include about 2% PEG MW 6 kDa.

The microtube shell of the invention can be designed such that it enables the passage of certain molecules (e.g., a substrate of an enzyme) while preventing the passage of other molecules (e.g., a certain enzyme), depending on the geometry (pore size) and/or the electrical charge of the molecules with respect to the geometry (length and radius), surface energy, electrical charge of the nanopore(s) of the shell, and the viscosity and surface tension of the liquid containing the molecules (e.g., the substrate of the enzyme). In addition, the porosity and pore size of the shell can control the release of the molecule-of-interest which is attached to the microtube. For example, a higher porosity and/or pore size can result in increased rate of release of the molecule-of-interest.

Alternatively, the microtube shell can be made such that it prevents diffusion or any passage of the molecule-of-interest therethrough (i.e., substantially devoid of pores, or with pores smaller than the molecule-of-interest).

As mentioned, the second polymeric solution comprises the molecule-of-interest. Such a molecule (or molecules) can be any naturally occurring or synthetic molecule such as a polypeptide, a polynucleotide, a carbohydrate or a polysaccharide, a lipid, a drug molecule, a small molecule (e.g., a nucleotide base, an amino acid, a nucleotide, an antibiotic, a vitamin or a molecule which is smaller than 0.15 kDa), or any combination thereof. The molecule-of-interest can be produced by recombinant DNA technology or by known synthesis methods such as solid phase.

According to some embodiments of the invention, the molecule-of-interest comprises a polypeptide such as an enzyme. Such polypeptides (e.g., enzymes) can be naturally occurring (e.g., mammals such as primates, rodents and Homo sapiens, plants, fungi, protozoa, bacteria and viruses) or synthetic (e.g., derived from in vitro evolution) and can be selected according to the desired application.

The following non-limiting list of enzymes can be attached to the microtube of the invention: DNA polymerase (EC 2.7.7.7), DNase (EC 3.1.11.4), RNA polymerase (EC 2.7.7.6), DNA ligase (EC 6.5.1.1), RNA ligase (EC 6.5.1.3), alcohol dehydrogenase (EC 1.1.1.1), homoserine dehydrogenase (EC 1.1.1.3), acetoin dehydrogenase (EC 1.1.1.5), glycerol dehydrogenase (EC 1.1.1.6), L-xylulose reductase (EC 1.1.1.10), L-arabinitol 2-dehydrogenase (EC 1.1.1.13), L-iditol 2-dehydrogenase (EC 1.1.1.14), mannitol-1-phosphate 5-dehydrogenase (EC 1.1.1.17), mannitol 2-dehydrogenase (EC 1.1.1.138), glucose oxidase (EC 1.1.3.4), L-sorbose oxidase (EC 1.1.3.11), lactate-malate transhydrogenase (EC 1.1.99.7), formaldehyde dehydrogenase (EC 1.2.1.1), aryl-aldehyde dehydrogenase (EC 1.2.1.29), aldehyde oxidase (EC 1.2.3.1), pyruvate synthase (EC 1.2.7.1), cortisone α-reductase (EC 1.3.1.4), lathosterol oxidase (EC 1.3.3.2), D-proline reductase (EC 1.4.4.1), dihydrofolate reductase (EC 1.5.1.3), methylenetetrahydrofolate reductase (NADPH) (EC 1.5.1.20), cystine reductase (NADH) (EC 1.6.1.4), cob(II) alamin reductase (EC 1.6.99.9), sulfite reductase (EC 1.8.1.2), cytochrome-c oxidase (EC 1.9.3.1), NADH peroxidase (EC 1.11.1.1), homogentistate 1,2-dioxygenase (EC 1.13.11.5), *Photinus*-luciferin 4-monooxygenase (1.13.12.7), anthranilate 3-monooxygenase (EC 1.14.13.35), steroid 9α-monooxygenase (EC 1.14.99.25), mercury(II) reductase (EC 1.16.1.1), nicotinamide N-methyltransferase (EC 2.1.1.1), thymidylate synthase (EC 2.1.1.45), site-specific DNA-methyltransferase (adenine-specific) (EC 2.1.1.72), tryptophan 2-C-methyltransferase (EC 2.1.1.106), glycine formininotransferase (EC 2.1.2.4), aspartate carbamoyltransferase (EC 2.1.3.2), transaldolase (EC 2.2.1.2), arylamine N-acetyltransferase (EC 2.3.1.5), arginine N-succinyltransferase (EC 2.3.1.109), phosphorylase (EC 2.4.1.1), glycosaminoglycan galactosyltransferase (EC 2.4.1.74), thymidine phosphorylase (EC 2.4.2.4), β-galactoside α-2,6-sialyltransferase (EC 2.4.99.1), galactose-6-sulfurylase (EC 2.5.1.5), aspartate transaminase (2.6.1.1), hexokinase (EC 2.7.1.1), choline kinase (EC 2.7.1.32), acetate kinase (EC 2.7.2.1), creatine kinase (EC 2.7.3.2), adenylate kinase (EC 2.7.4.3), nucleotide pyrophosphokinase (EC 2.7.6.4), sulfate adenylyltransferase (ADP) (EC 2.7.7.5), aryl sulfotransferase (EC 2.8.2.1), carboxylesterase (3.1.1.1), acetyl-CoA hydrolase (EC 3.1.2.1), alkaline phosphatase (3.1.3.1), phosphodiesterase I (EC 3.1.4.1), dGTPase (EC 3.1.5.1), steryl-sulfatase (EC 3.1.6.2), exodeoxyribonuclease I (EC 3.1.11.1), ribonuclease T1 (EC 3.1.27.3), α-amylase (EC 3.2.1.1), purine nucleosidase (EC 3.2.2.1), epoxide hydrolase (EC 3.3.2.3), lysyl aminopeptidase (EC 3.4.11.15), carboxypeptidase A2 (EC 3.4.17.15), trypsin (EC 3.4.21.4), glutaminase (EC 3.5.1.2), barbiturase (EC 3.5.2.1), ATP deaminase (EC 3.5.4.18), inorganic pyrophosphatase (EC 3.6.1.1), oxaloacetase (EC 3.7.1.1), oxalate decarboxylase (EC 4.1.1.2), mandelonitrile lyase (EC 4.1.2.10), isocitrate lyase (4.1.3.1), fumarate hydratase (EC 4.2.1.2), pectate lyase (EC 4.2.2.2), histidine ammonia-lyase (EC 4.3.1.3), cyanate lyase (4.3.99.1), cysteine lyase (EC 4.4.1.10), DDT-dehydrochlorinase (EC 4.5.1.1), adenylate cyclase (EC 4.6.1.1), alanine racemase (5.1.1.1). tartrate epimerase (EC 5.1.2.5), retinal isomerase (EC 5.2.1.3), L-rhamnose isomerase (EC 5.3.1.14), prostaglandin-D synthase (EC 5.3.99.2), phosphoglucomutase (EC 5.4.2.2), lanosterol synthase (EC 5.4.99.7), DNA topoisomerase (EC 5.99.1.2), tyrosine-tRNA ligase (EC6.1.1.1), acetate-CoA ligase (EC 6.2.1.1), acetylcholinesterase (EC 3.1.1.7), butyrylcholinesterase (EC 3.1.1.8) and glutathione synthase (EC 6.3.2.3).

According to an embodiment of the invention, the enzyme which is attached to the microtube is alkaline phosphatase (e.g., SEQ ID NO:1 or 8; EC 3.1.3.1) or beta-galactosidase (e.g., SEQ ID NO:2 or 9; EC 3.2.1.23).

The term "polynucleotide" as used herein refers to a single stranded or double stranded oligomer or polymer of ribonucleic acid (RNA) or deoxyribonucleic acid (DNA) or mimetics thereof. This term includes polynucleotides composed of naturally-occurring bases, sugars and covalent internucleoside linkages (e.g., backbone) as well as polynucleotides having non-naturally-occurring portions which function similarly to respective naturally-occurring portions.

The polynucleotide which is attached to the microtube of the invention can be generated according to any oligonucleotide synthesis method known in the art such as enzymatic synthesis, liquid phase or solid phase synthesis (using a commercially available equipment from, for example, Applied Biosystems). Equipment and reagents for executing solid-phase synthesis are commercially available from, for example, Applied Biosystems. Any other means for such synthesis may also be employed; the actual synthesis of the oligonucleotides is well within the capabilities of one skilled in the art and can be accomplished via established methodologies as detailed in, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988) and "Oligonucleotide Synthesis" Gait, M. J., ed. (1984) utilizing solid phase chemistry, e.g. cyanoethyl phosphoramidite followed by deprotection, desalting and purification by for example, an automated trityl-on method or HPLC. Liquid phase synthesis of oligonucleotides can be performed using methods known in the art (see for example, Bonora G M, et al., 1998, Biol. Proced. Online. 1: 59-69; Padiya K J and Salunkhe M M., 2000, Bioorg. Med. Chem. 8: 337-42). It will be appreciated that for the preparation of multiple labeled polynucleotides, a large scale oligonucleotide synthesis can be utilized essentially as described elsewhere (Anderson N G. et al., Appl Biochem Biotechnol. 1995 July-September; 54 (1-3):19-42; Rahmann S., Proc IEEE Comput Soc Bioinform Conf. 2002; 1:54-63).

Additionally or alternatively, the polynucleotide which is attached to the microtube of the invention can be generated by recombinant DNA techniques using any known DNA replication or transcription system (e.g., using bacterial cells, eukaryotic cells).

As mentioned, the molecule-of-interest can be a drug molecule. Such a drug can be any synthetic, chemical or biological molecule.

Non-limiting examples of biological drug molecules include antisense oligonucleotides, Ribozymes, DNAzymes, siRNA, receptor agonists, antagonists, hormones, growth factors and antibodies. Non-limiting examples of which chemical drug molecules include chemotherapy agents, Paclitaxel (Taxol®), radiation seed particles (e.g., see Hypertext Transfer Protocol://World Wide Web (dot) oncura (dot) com), as well as natural or synthetic vitamins.

The molecule-of-interest which is attached to the microtube of the invention can be labeled. Such a label can be an intrinsic property of the molecule-of-interest (e.g., as in the case of green fluorescent protein) or can be a label which is attached to the molecule-of-interest using known methods. For example, the label can be a fluorescent labeling in which a fluorophore (i.e., an entity which can be excited by light to emit fluorescence) or a radio-isotope is conjugated via a linker or a chemical bond to the molecule-of-interest. Alternatively, the molecule-of-interest can be indirectly labeled via a covalently conjugated enzyme (e.g., horse radish peroxidase) and a covalently conjugated substrate (e.g., o-phenylenediamine) which upon interaction therebetween yield a colorimetric or fluorescent color.

The molecule-of-interest can also comprise a member of an affinity pair, which is capable of reversibly or non-reversibly binding with high affinity (e.g., less than $10^{-7}$ M, e.g., less than $10^{-8}$ M, less than $10^{-9}$, less than $10^{-10}$ M) to a specific molecule. For example, the affinity pair can be an enzyme-substrate pair, a polypeptide-polypeptide pair (e.g., a hormone and receptor, a ligand and receptor, an antibody and an antigen, two chains of a multimeric protein), a polypeptide-small molecule pair (e.g., avidin or streptavidin with biotin, enzyme-substrate), a polynucleotide and its cognate polynucleotide such as two polynucleotides forming a double strand (e.g., DNA-DNA, DNA-RNA, RNA-DNA), a polypeptide-polynucleotide pair (e.g., a complex formed of a polypeptide and a DNA or RNA e.g., aptamer), a polypeptide-metal pair (e.g., a protein chelator and a metal ion), a polypeptide and a carbohydrate (leptin-carbohydrate), and the like.

The molecule-of-interest, which is comprised within the second polymeric solution, can be attached to the coat over the internal surface of the shell. For example, as shown in FIG. 5 and described in Example 3 of the Examples section which follows, most of the β-GAL enzymatic activity was detected inside the microtube, demonstrating the attachment of the enzyme to the coat over the internal surface of the shell.

During the electrospinning process some molecules-of-interest which are comprised within the second polymeric solution may migrate to the outer surface of the shell (i.e., mixed with the first polymeric solution) depending on their charge state, size and geometry. For example, as shown in FIG. 3 and described in Example 2 of the Examples section which follows, some of the alkaline phosphatase activity was detected in the rinsing buffer of the microtube.

According to some embodiments of the invention attachment of the molecule-of-interest is performed following microtube formation. For example, the microtube can be soaked with a solution containing the molecule-of-interest. The molecule-of-interest can diffuse through the shell pores and enter the inner lumen of the microtube. In addition, the microtube can be covalently attached to the molecule-of-interest (e.g., via SH groups).

Regardless of the method of production, the present invention provides a microtube which comprises an electrospun shell, an electrospun coat over an internal surface of the shell and a molecule-of-interest attached to the microtube.

As used herein, the phrase "electrospun shell" refers to a hollow element of a tubular shape, made of one or more polymers, produced by the process of electrospinning as detailed above.

As used herein the phrase "electrospun coat" refers to a thin layer covering the internal surface of the shell of the microtube of the invention which is made of one or more polymers by the process of electrospinning as detailed above.

One of ordinary skill in the art will know how to distinguish an electrospun object from objects made by means which do not comprise electrospinning by the high orientation of the macromolecules, the skin (e.g., shell) morphology, and the typical dimensions of the microtube which are unique to electrospinning.

The microtube of the invention can be an individual (e.g., single or separated) microtube or can form part of a plurality (e.g., an aligned array) of microtubes which can be either connected to each other or separated (as single, not-connected microtubes).

For the production of a single microtube a fork like clip is attached to the edge of the rotating disk. The disk is rotated for 1-2 seconds and individual microtubes are formed between the sides of the clip. In a similar way individual electrospun fibers were collected (see E. Zussman, M. Burman, A. L. Yarin, R. Khalfin, Y. Cohen, "Tensile Deformation of Electrospun Nylon 6,6 Nanofibers," *Journal of Polymer Science Part B: Polymer Physics*, 44, 1482-1489, 2006, herein incorporated by reference in its entirety).

Alternatively, when using a rotating collector, a plurality of microtubes can be formed and collected on the edge of the collector as described elsewhere for electrospun fibers (A. Theron, E. Zussman, A. L. Yarin, "Electrostatic field-assisted alignment of electrospun nanofibers", *Nanotechnology J.*, 12, 3: 384-390, 2001; herein incorporated by reference in its entirety).

The plurality of microtubes can be arranged on a single layer, or alternatively, the plurality of microtubes define a plurality of layers hence form a three dimensional structure. The microtubes can have a general random orientation, or a preferred orientation, as desired. For example, when the fibers are collected on a cylindrical collector such as a drum, the microtubes can be aligned predominantly axially or predominantly circumferentially. Different layers of the electrospun microtubes can have different orientation characteristics. For example, without limiting the scope of the present invention to any specific ordering or number of layers, the microtubes of a first layer can have a first predominant orientation, the microtubes of a second layer can have a second predominant orientation, and the microtubes of third layer can have general random orientation.

The microtube of the invention can be available as a dry fibrous mat(s) (e.g., as spun dry microtubes) or as a wetted mat(s) (e.g., following immersing or filling the microtube with a liquid).

The microtube of the invention which is attached to the molecule-of-interest may be configured as or in a microfluidics device. "Lab-on-a-chip" is described in a series of review articles [see for example, Craighead, H. Future lab-on-a-chip technologies for interrogating individual molecules. Nature 442, 387-393 (2006); deMello, A. J. Control and detection of chemical reactions in microfluidic systems. Nature 442, 394-402 (2006); El-Ali, J., Sorger, P. K. &

Jensen, K. F. Cells on chips. Nature 442, 403-411 (2006); Janasek, D., Franzke, J. & Manz, A. Scaling and the design of miniaturized chemical-analysis systems. Nature 442, 374-380 (2006); Psaltis, D., Quake, S. R. & Yang, C. H. Developing optofluidic technology through the fusion of microfluidics and optics. Nature 442, 381-386 (2006); Whitesides, G. M. The origins and the future of microfluidics. Nature 442, 368-373 (2006); Yager, P. et al. Microfluidic diagnostic technologies for global public health. Nature 442, 412-418 (2006)] each of which is fully incorporated herein by reference].

According to some embodiments of the invention, the liquid which fills in, flows in or surrounds the microtube enables the desorption (detachment) of the molecule-of-interest from the microtube (e.g., from the polymer included in the coat over the internal surface of the shell). According to of some embodiments of the invention the desorption process facilitates the interaction between the molecule-of-interest and a substrate. According to some embodiments of the invention the desorption process enables the flow and/or the release of the molecule-of-interest within and/or from the microtube.

According to some embodiments of the invention, the molecule-of-interest which is attached to the microtube of the invention remains active, i.e., maintains the activity, or at least a portion thereof, which it possessed prior to the attachment (e.g., of the same molecule-of-interest before electrospinning, or when not-attached to the microtube). The term "activity" as used herein refers to any of a catalytic activity, kinetics, and/or affinity to a substrate, a ligand or an affinity member of the molecule. Such an activity can be any biological activity such as catalysis, binding (with a specific affinity), hybridization, chelation, degradation, synthesis, catabolism, hydrolysis, polymerization, transcription, and the like.

As used herein the phrase "at least a portion of the activity" refers to at least about 10%, at least about 20-50%, e.g., more than about 50%, e.g., more than about 60%, e.g., more than about 70%, e.g., more than about 75%, e.g., more than about 80%, e.g., more than about 90%, e.g., more than about 95% of the activity which the molecule-of-interest possessed prior to the attachment to the microtube.

For example, as mentioned before and described in the Examples section which follows, the enzymes contained within the microtubes preserved the specific activity to their substrates at a kinetic which is comparable (i.e., within the same order of magnitude) to that of the enzyme in the polymeric solution prior to electrospinning.

The microtube of the invention which is attached to an active molecule-of-interest can be used in various applications which require the attachment of active molecules (e.g., enzymes, DNA, RNA) to a support and optionally also the controlled release therefrom.

According to some embodiments of the invention, the microtube of the invention is attached to more than one type of molecule-of-interest. The combination of molecules can be selected according to the intended use. For example, several molecules (e.g., enzymes) which are involved in complex reactions (e.g., processing of a substrate or a mixture of substrates) can be used.

Thus, according to an aspect of the invention, there is provided a method of processing a substrate-of-interest. The method is effected by contacting the substrate-of-interest with the microtube of the invention, wherein the molecule-of-interest is capable of processing the substrate, thereby processing the substrate-of-interest.

As used herein the term "processing" refers to a catalytic activity performed by the molecule-of-interest which is attached to the microtube on its cognate substrate.

According to some embodiments of the invention, such a process can concomitantly incorporate of the substrate-of-interest in a synthesis reaction catalyzed by the molecule-of-interest.

For example, the microtube of some embodiments the invention can be used as a micro-reactor (e.g., bioreactor) for chemical transition reactions requiring high concentrations of several enzymes. As described in Example 4 of the Examples section which follows and schematically illustrated in FIG. 9, the microtube of the invention can be attached to certain molecules (enzymes in this case), which together catalyze a multi-step synthesis reaction (e.g., cascade) which converts an initial substrate (e.g., compound A) to an end-product (e.g., compound E). As mentioned, the selective shell of the microtube can be designed such that it prevents the leakage (escape by diffusion) of the intermediate compounds (e.g., compounds B, C and D) therethrough and thus enables sufficiently high concentrations of such compounds as needed for the synthesis of the end product. The local concentration of the intermediate molecules formed from the initial substrate (entrapped at the time of spinning or externally added after electro spinning to the formed microtube) are about 2-10 orders of magnitude greater than the concentrations formed in an open system. Thus, the microtube of some embodiments of the invention exhibits a great kinetic advantage in multi-step reactions as compared to an open system. Microtubes are in this way similar to living cells which function on the same principle.

For example, to synthesize an indole-glycerol phosphate, an intermediate compound in tryptophan synthesis within cells, a microtube of some embodiments of the invention can be attached to the enzymes anthranilate-phosphoribosyl transferase (EC 2.4.2.18), phosphoribosylanthranilate isomerase (EC 5.3.1.24) and indole-3-glycerol-phosphate synthase (EC 4.1.1.18), and the reaction commences when anthranilate and phosphoribosyl-pyrophosphate interact with the attached enzymes. The substrates (anthranilate and phosphoribosyl-pyrophosphate) can be either added externally to the reaction medium (within which the microtube is placed) or can be attached to the microtube by mixing them within the second polymeric solution. When the substrates are supplied externally, pores of about 2-20 nm in diameter should exist in the shell to allow diffusion of anthranilate and phosphoribosyl-pyrophosphate therethrough.

According to some embodiments of the invention, such a process can be the incorporation of the substrate-of-interest in a catabolism reaction catalyzed by the molecule-of-interest.

A catabolism reaction can be the degradation (e.g., by hydrolysis) of a toxic molecule for the purpose of detoxification (e.g., detoxifying water) or decomposition of an unwanted molecule. Examples include, but are not limited to, the removal of the chlorine entity from atrazine (see FIG. 10) and the degradation of cyanide resulting from silver mining.

According to an aspect of the invention, there is provided a method of depleting a molecule from a solution. The method is effected by contacting the solution with the microtube of the invention, wherein the member of the affinity pair (which is attached to the microtube) is selected capable of binding the molecule (which is to be removed), thereby depleting the molecule from the solution.

According to an embodiment of the invention, the method further comprising collecting the solution following the contacting.

As used herein the phrase "depleting" refers to removing an amount e.g., at least about 50%, at least about 60%, at least about 70%, at least about 80%, at least about 90%, at least about 95%, e.g., 99%, e.g., 100% of the molecule from the solution.

According to some embodiments of the invention, the depletion (removal) of the molecule from the solution is effected within a short time period, such as within minutes (e.g., 1-30 minutes), hours (e.g., 1-10 hours) or several days (e.g., 1-5 days).

As used herein the phrase "contacting" refers to enabling the interaction between the molecule and the member of the affinity pair, which is attached to the microtube, for a time period which is sufficient for depleting the molecule from the solution. Such a contact can take place while the solution is passing through (e.g., via capillary forces) the end(s) of the hollow structure of the microtube and/or through the shell pores. Additionally or alternatively, such a contact between the molecule and the member of the affinity pair can take place by incubating the microtube in the solution (e.g., by placing the microtube in a container including the solution).

The solution can be any water-based solution which includes inorganic or organic molecules, such as a biological sample or a sample from a non-living source such as stream or ocean waters. As used herein the phrase "biological sample" refers to any sample derived from a living organism such as plant, bacteria or mammals, and can include cells or alternatively be cell-free (i.e., include only a biological fluid). For example, a biological sample of an individual can include body fluids such as blood or components thereof (e.g., white blood cells, red blood cells, coagulation factors, leukocytes, neutrophils, serum, plasma), cerebrospinal fluid, urine, lymph fluids, and various external secretions of the respiratory, intestinal and genitourinary tracts, tears, saliva, milk, amniotic fluid and chorionic villi, a tissue biopsy, a tissue section, a malignant tissue, and the like. The sample can be derived from the individual and be further tested in vitro or ex vivo, or alternatively, can be not physically removed from the subject (e.g., for in situ detection and/or diagnosis).

According to some embodiments of the invention, the solution is an aqueous solution such as a drinking water, a groundwater and/or an industrial waste water. According to some embodiments of the invention, the microtube of the invention forms part of an aqueous system designed for treatment of the aqueous solution (e.g., for depleting, eliminating or removing toxic moieties therefrom).

For example, to remove a certain metal ion (e.g., copper, gold, nickel, zinc, lead, mercury, cadmium, silver, iron, manganese, palladium, and platinum) from water, the microtube of the invention can be attached to a water soluble ethylene dichloride ammonia polymer, which contains dithiocarbamate salt groups and is capable of chelating the metal ion (U.S. Pat. No. 5,346,627). Thus, by contacting the water with the microtube the ethylene dichloride ammonia polymer binds to the metal ion and removes it from the water. Water collected after being in contact with the microtube is substantially devoid of the metal ion. Alternatively, these metal ions may be removed by attaching a protein chelator of such metal ions to the microtube.

Alternatively, to remove a ligand (e.g., a hormone, a substrate, a co-factor or a vitamin such as biotin) from a solution containing a biological sample, the microtube can be attached to a polypeptide which is member of an affinity pair such as an enzyme, a hormone or streptavidin, and following contacting the solution with the microtube, the ligand remains attached to the microtube while the solution is substantially devoid of the ligand (e.g., includes less than 0.5%, e.g., less than 0.1%, e.g., less than 0.01% of the ligand).

According to some embodiments of the invention, the molecule which is to be removed from the solution comprises an antigen and the member of the affinity pair comprises the antibody capable of specifically binding the antigen.

For example, the microtube of the invention can be used to remove virus particles from a blood sample. Briefly, an anti-virus antibody (e.g., anti-HIV antibodies such as those described in Tullis, R H., et al., Therapeutic Apheresis and Dialysis, 6: 213-220) can be attached to the microtube and a blood sample containing the virus particles (e.g., HIV particles) can be in contact with the microtube such that the virus particles bind to their respective antibodies and the collected blood sample (after being in contact with the microtube) is substantially devoid of the viral particles.

The member of the affinity pair which is attached to the microtube of the invention can be also used to isolate a molecule from a solution.

According to an aspect of the invention, there is provided a method of isolating a molecule from a solution. The method is effected by: (a) contacting the solution with the microtube of the invention under conditions which allow binding of the molecule to the microtube via the member of the affinity pair which is selected capable of binding the molecule, and (b) eluting the molecule from the microtube, thereby isolating the molecule from the solution.

As used herein the term "isolating" refers to physically separating the molecule from the solution or its other components by binding the molecule to the member of the affinity pair that is attached to the microtube and eluting the bound molecule therefrom. As used herein the term "eluting" refers to dissociating the bound molecule from the microtube. Those of skills in the art are capable of adjusting the conditions required for eluting (e.g., releasing) the molecule from the microtube and/or separating the molecule from the other member of the affinity pair.

As is further described in Example 5 of the Examples section which follows, the present inventors have envisaged the use of the microtube of the invention, which is attached to a member of an affinity pair, as a biosensor, for the detection of molecules in a sample. Such a biosensor can be advantageous over known open field biosensors (e.g., sensors in which the member of the affinity pair is conjugated to a solid support not having a tubular structure, such as a flat support) due to the increased ratio between the size of the microtube surface (which attaches the member of the affinity pair) and the volume of the sample being in contact therewith.

According to an aspect of the invention, there is provided a method of detecting a presence of a molecule in a sample. The method is effected by (a) contacting the sample with the microtube of the invention, wherein the member of the affinity pair is selected capable of binding the molecule, and; (b) detecting binding of the molecule by the member of the affinity pair, thereby detecting the presence of a molecule in the sample.

As used herein the phrase "detecting binding" refers to identifying a change in the concentration, conformation, spectrum or electrical charge of the molecule in the sample and/or the member of the affinity pair that is attached to the microtube following the binding therebetween. Identification of such binding can be performed using methods known in the art such as following the fluorescence or the color of the sample, radioactivity in the sample, the electrical conductivity of the sample and the like.

As mentioned hereinabove and described in Example 2 of the Examples section which follows, the microtube of the invention can release the molecule-of-interest attached thereto (a releasing apparatus).

The microtube of some embodiments the invention (e.g., a microtube made of biocompatible polymers) can be implanted in a subject in need thereof.

As used herein the phrase a "subject in need thereof" refers to any animal subject e.g., a mammal, e.g., a human being which suffers from a pathology (disease, disorder or condition) which can be treated by the molecule that is attached to or flows through the microtube of the invention.

The term "treating" as used herein refers to inhibiting, preventing or arresting the development of a pathology and/or causing the reduction, remission, or regression of a pathology. Those of skill in the art will understand that various methodologies and assays can be used to assess the development of a pathology, and similarly, various methodologies and assays may be used to assess the reduction, remission or regression of a pathology.

Methods of implanting grafts such as the microtube of the invention into a subject are known in the art. For example, the microtube can be implanted subcutaneously, intradermally, or into any body cavity (e.g., abdomen), as well as into the vascular system (using e.g., a hollow catheter delivery system). Alternatively, the microtube of the invention can be connected to a body conduit (e.g., a blood vessel such as a vein or an artery) such that it enables the flow of a fluid therethrough.

For example, the microtube of the invention which is capable of depleting a molecule from a solution as described above, can be connected to a blood vessel of the subject. For example, the proximal end of the microtube (or of a plurality of microtubes) can be connected to a feeding blood vessel and the distal end of the microtube(s) can be connected to a receiving blood vessel. Such a configuration can be used, for example, for hemodialysis and depletion of a specific molecule (e.g., a virus particle such as HIV, hepatitis virus such as HCV) from the blood stream of the subject.

In addition, a microtube which is attached to a drug molecule can be implanted in a subject in need thereof to thereby release a therapeutically effective amount of the drug to cells of the subject.

As used herein the phrase "therapeutically effective amount" means an amount of the molecule-of-interest (e.g., the drug, the active molecule) effective to prevent, alleviate or ameliorate symptoms of a pathology or prolong the survival of the subject being treated. Determination of a therapeutically effective amount is well within the capability of those skilled in the art.

For example, in case the molecule-of-interest comprises a polynucleotide, such a polynucleotide can be used in gene therapy applications to either increase an expression level or activity of a desired polypeptide needed for treating the pathology, or to decrease or inhibit the expression level of a polynucleotide causing the pathology (e.g., antisense technology). Alternatively, the polynucleotide can be used to immunize the subject by inducing an immune response thereagainst.

Alternatively, in case the molecule-of-interest is a polypeptide, such a polypeptide can be used in a subject in need of polypeptide therapy, such as a subject having a decreased or no activity of the polypeptide (e.g., due to a genetic disease, auto-antibodies, pathogen infection, degeneration or a decrease in tissue functioning), as well as for other therapeutic applications such as immunization with the polypeptide.

Non-limiting examples of pathologies which require polypeptide therapy and can be treated using the microtube of the invention include, metabolic disorders such as phenylketonuria (PKU), Gaucher disease, muscular dystrophy [Duchenne (DMD) and Becker (BMD) Muscular Dystrophies], Aceruloplasminemia (an iron metabolic disorder), endocrine diseases such as diabetes, autoimmune diseases such as multiple sclerosis (MS), rheumatoid arthritis (RA), and psoriasis, and various cancers (e.g., lymphoma).

Following is a non-limiting list of polypeptides which can be attached to the microtube of the invention in order to treat pathologies requiring polypeptide therapy. Phenylalanine hydroxylase [(PAH); GenBank Accession Nos. NM_000277.1 (nucleic acid sequence) and NP_000268.1 (SEQ ID NO:3; amino acid sequence)] for treating phenylketonuria (PKU), dystrophin [(DMD); GenBank Accession Nos. NM_000109.2 (nucleic acid sequence) and NP_000100.2 (SEQ ID NO:4; amino acid sequence)] for treating Duchenne (DMD) and Becker (BMD) Muscular Dystrophies, beta-glucosidase [(GBA); GenBank Accession Nos. NM_001005741.1 (nucleic acid sequence) and NP_001005741.1 (amino acid sequence; SEQ ID NO:5)] for treating Gaucher disease, insulin [GenBank Accession Nos. NM_000207.1 (nucleic acid sequence) and NP_000198.1 (amino acid sequence; SEQ ID NO:6)] for treating diabetes, and ceruloplasmin ferroxidase [(CP); GenBank Accession Nos. NM_000096.1 (nucleic acid sequence) and NP_000087.1 (SEQ ID NO:7; amino acid sequence)] for treating aceruloplasminemia, CD20 monoclonal antibodies for treating non-Hodgkin's lymphoma and autoimmune disease (Yazawa N, et al., 2005, Proc Natl Acad Sci USA. 102:15178-83) and T-cell receptor peptides for treating of multiple sclerosis (MS), rheumatoid arthritis (RA), and psoriasis (Vandenbark A A, et al., 2001, Neurochem Res. 26:713-30).

Targeted delivery of a drug molecule to a tissue-of-interest is desired in various pathologies, especially in cases where the effect of the drug is deleterious to non-diseased tissues or when high concentrations of drug molecules are required to achieve a therapeutic effect on the diseased tissue (the tissue-of-interest). Thus, for example it is highly desired to have a targeted delivery of a chemotherapy agent or a radiation seed particle to the liver in case of hepatic cancer, or an angiogenic factor to coronary blood vessels, heart or carotid blood vessels in case of ischemia.

According to an embodiment of the invention, for targeted delivery of a drug molecule to a tissue-of-interest via the opening of the microtube (at the targeted tissue), the microtube of the invention is designed such that the electrospun shell is semi-permeable (i.e., prevents passage of the drug molecule but enables the penetration of water or a physiological solution therethrough) and the coat over the internal surface of the shell is attached to the drug molecule.

Such a microtube can be implanted in a subject such that the distal end of the microtube is implanted in or in close proximity to the tissue-of-interest. As used herein the term "proximity" refers to being in a cavity defined by the tissue, for example, if the tissue in which the drug is released is a blood vessel (artery or vein) the cavity is a lumen of such a blood vessel, or if the tissue in which the medication is released is a heart chamber, then the cavity is an atrium or a ventricle. It will be appreciated that the other end of the microtube can be also implanted in proximity to the tissue-of-interest. Alternatively, the proximal end of the microtube can be either sealed using e.g., a laser beam to prevent delivery of the drug to undesired cells/tissues of the subject, or if needed, could be placed outside the body, or subcutaneously such that the microtube can be replenished with additional drug molecules using extra thin needles (e.g., which can penetrate a 5 μm lumen of the microtube).

Once the microtube of some embodiments of the invention (e.g., a microtube with a semi permeable shell and a drug molecule attached to the coat over the internal surface of the shell) is implanted in the subject it can be filled with a physiological fluid (e.g., of the subject) which is capable of dissolving the water-soluble polymer of the coat over the internal surface of the shell to thereby release the drug molecule therefrom. The released drug molecule flows by capillary forces within the microtube until reaching the end of the open lumen, which is in proximity of the tissue-of-interest.

If needed, the microtube according to this embodiment of the invention, can be also replenished with additional drug molecules or other molecules which can increase the effect of the drug molecule released by the microtube. For example, if the drug molecule attached to the microtube is an angiogenic factor, a solution saturated with gasses (e.g., oxygen) can be administered to the microtube (e.g., after implantation in the subject) to thereby increase the anti-ischemic effect of the angiogenic factor.

Targeted delivery of a drug to a tissue-of-interest can be also effected using a microtube in which the shell enables diffusion of the drug molecule therethrough and accordingly, the drug molecule can be released through the shell pores and/or the distal opening of the microtube at the desired tissue.

The invention further envisages the use of the microtube of the invention, which include a molecule-of-interest attached thereto, for guiding cell growth ex vivo or in vivo. For example, neuronal cells can be placed near or in direct contact with the microtube which is attached to necessary growth factors and nutrients needed for neuronal growth. It will be appreciated that once an initial neuronal growth has occurred ex vivo, such a system (i.e., the microtube and the neuronal cells) can be implanted in a subject in need thereof (e.g., a subject with degenerated, damaged or injured neuronal cells) to thereby enable neuronal growth and guidance.

The microtube of some embodiments of the invention can be included in a kit/article of manufacture along with a packaging material and/or instructions for use in any of the above described methods or applications.

As used herein the term "about" refers to ± 10%.

The terms "comprises", "comprising", "includes", "including", "having" and their conjugates mean "including but not limited to". This term encompasses the terms "consisting of" and "consisting essentially of".

The phrase "consisting essentially of" means that the composition or method may include additional ingredients and/or steps, but only if the additional ingredients and/or steps do not materially alter the basic and novel characteristics of the claimed composition or method.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

An electrospinning apparatus can include a controller programmed with parameters as described herein or measuring output and automatically modifying. Controller can be hardware, software, firmware, with CPU, volatile memory, optional non-volatile memory.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions, illustrate some embodiments of the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W.H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., Eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

General Materials and Experimental Methods

Enzymes and Solutions—

The compositions of the shell and core solutions are given in Table 3, hereinbelow. All polymers and solvents were purchased from Sigma-Aldrich and were used as is. Alkaline phosphatase (AP) and beta-galactosidase (β-GAL) from *E. coli* were also purchased from Sigma-Aldrich. AP cleaves monophosphate esters and has a molecular weight of about 80,000 Da. β-GAL is a tetrameric enzyme of 465,396 Da consisting of four identical subunits each (Zabin I., et al., 1980) and catalyzes the hydrolysis of the terminal galactosidyl group of β-galactosides. Both enzymes were initially dissolved in water and then mixed with the core solution.

TABLE 3

Two types of core-shell microtubes: composition of the solutions

| Type | Shell solution | Core solution |
|---|---|---|
| 1 | 10% PCL 80 K; in CHCl$_3$:DMF (90:10 by weight) | 4% (w/w) PEG 600 K + 0.0733 mg/ml AP or 2.38 units/ml β-GAL; in ethanol:H$_2$O (26:74 by weight) |
| 2 | 10% PCL 80 K + 1% PEG 6 K; in CHCl$_3$:DMF (90:10 by weight) | 4% (w/w) PEG 600 K + 0.0733 mg/ml AP or 2.38 units/ml β-GAL; in ethanol:H$_2$O (26:74 by weight) |

Table 3. Microtubes were formed by co-electrospinning of the shell solution (a first polymeric solution for forming the shell) and a core solution (a second polymeric solution for forming the coat over the internal surface of the shell).

Electrospinning—

Hollow microtubes (core-shell hollow fibers) were fabricated by a co-electrospinning process using the set up described by Sun et al. 2003 and Zussman et al. 2006. All experiments were conducted at room temperature (about 22° C.) and a relative humidity of about 35%. The spinning parameters were as follow: the electrostatic field used was approximately 0.44 kV/cm and the distance between the spinneret and collector plate was 16 cm. The flow rates of both the core and shell solutions were controlled by two syringe pumps and were 3.5 ml/hour for the shell solution and 1 ml/hour for the core solution. The fibers were collected as a strip on the edge of a vertical rotating wheel (Theron A., et al., 2001) having a velocity of 1.2 m/second. For fluorescence microscopy, a few fibers were collected directly onto a microscope slide Imaging—

Images of the fibers were obtained using a Leo Gemini high resolution scanning electron microscope (HRSEM) at an acceleration voltage of 3 kV and a sample to detector distance of 3-5 mm. The specimens were coated with a thin gold film to increase their conductivity. Fluorescence microscope Leica DM IRE2 at excitation and emission wave lengths of 359 and 361 nm, respectively, was used for the imaging of fibers filled with fluorescent product.

Measurement of the Enzyme Activity—

To measure enzyme activity, pieces of mat were weighed and dipped in assay solution according to Table 4, hereinbelow. At each time of sampling, the solution was mixed with a vortex mixer, and 1 ml of the assay mixture was transferred to spectrophotometer cuvette. The absorbance of the solution was measured in a Perkins-Elmer spectrophotometer at a wavelength of 410 nm. For both enzymatic reactions, the substrates are colorless but the products, para-nitrophenol for AP and ortho-nitrophenol for 13-GAL, are yellow with an absorption maximum at 410 nm. After the absorbance was measured, the liquid was returned to the assay vessel. Units, activity and relative activity are defined as follow:

$$\text{Unit} = \frac{\Delta A}{\Delta t} \cdot 1000 \quad (1)$$

$$\text{Activity of the mat} = \text{unit} \cdot C \text{ where } C = \frac{\text{mass of total mat}}{\text{mass of piece}} \quad (2)$$

$$\text{Relative Activity (\%)} = \frac{\text{Activity of the mat}}{\text{Activity of the core solution}} \cdot 100 \quad (3)$$

Where: $\Delta A$ is the difference is the absorbance at difference times, Dt, difference between $t_1$ and $t_2$ (two time points) taken in the linear region of the reaction curve, and C is a normalization factor which takes into account the different weight of each piece.

For the fluorescence microscope imaging a drop of the assay solution was put directly on the microscope slide on which a few fibers had been deposited. The fluorescent substrates were methylumbelliferyl-phosphate for alkaline phosphatase (AP) and methylumbelliferyl-galactoside for beta-galactosidase (β-GAL). These were used at the same concentrations as their nitro-phenyl analogs.

TABLE 4

Composition of the assays

| Enzyme | Substrate | Buffer | H₂O | Products |
|--------|-----------|--------|-----|----------|
| AP | 0.7 mg/ml p-nitrophenyl-phosphate (MW = 217 Da) 1 ml | TRIS-HCl buffer 1.5 ml | 0.5 ml | p-nitrophenol + PO₄ |
|  | 4-methylumbelliferyl-phosphate: fluorescence microscopy |  |  | 4-methylumbelliferone + PO₄ |
| β-GAL | 4 mg/ml o-nitrophenyl-β-D-galactoside 0.2 ml (MW = 301 Da) | Z-buffer 0.7 ml | 0.3 ml | o-nitrophenol + galactose |
|  | 4-methylumbelliferyl-β-D-galactoside: fluorescence microscopy |  |  | 4-methylumbelliferone + galactose |

Table 4.

Example 1

Attachment of Enzymes to Electrospun Microtubes

Experimental Results
Formation of Micro-Tubes—

Two types of electrospun hollow fibers have been fabricated with the polymers listed in Table 3, hereinabove. The resultant fibers are hollow structures, namely micro-tubes, as previously described by the present inventors (Dror, Y et al., 2007 and PCT/IB2007/054001, which is fully incorporated herein by reference). The hollow nature of these structures and the different morphologies of the tube walls are demonstrated in the high resolution scanning electron microscope (HRSEM) micrographs presented in FIGS. 1a-d. Type 1 fibers are made with only PCL in the shell and exhibit a rough surface due to the rapid evaporation of the solvent (FIGS. 1a and c). However, this roughness doesn't affect the intact nature of the walls. As PEG is added to the shell solution (Type 2), the walls become increasingly porous (FIGS. 1b and d) and pores can be seen even in the interior surface of the tubes (FIG. 1b). PEG and PCL are partially miscible due to favorable, but weak, intermolecular polar-interactions (Coleman M M, et al., 1991). During fiber solidification along with the evaporation of the solvents, the concentration of the components increases and phase separation takes place. However, since the PEG has a surfactant-like character it deposits an adherent film around the PCL domains resulting in the formation of pores rather than forming solid domains of PEG.

After electrospinning the tubes form a fibrous non-woven, aligned or non-aligned mat. When the mat material is placed in an aqueous environment, the coat over the internal surface of the shell dissolves and the enzymes are released (through desorption) and become active on their substrate(s). For a further description of the desorption process see FIG. 8 and Example 8 hereinbelow. This arrangement of material allows for flow-through technologies without subjecting the enzyme to the external environment and without the need for chemical attachment and can prevent loss of the entrapped enzyme.

Enzymes Attached to Fibers Maintain Normal Biological Activity—

The kinetics of the enzymatic reaction for alkaline phosphatase was measured as described in the experimental section and is presented in FIGS. 2a-b. The enzymatic reaction with the fibers was compared to the free enzyme in the core solution (before electrospinning) and normalized with respect to the weight of the analyzed pieces. The results strongly indicate that the enzyme attached in the fiber (e.g., encapsulated) maintains its biological activity after electrospinning and exhibits a reaction curve similar to the free enzyme. The curves are characteristic of enzymatic reactions when there is large excess of substrate. The colored product, p-nitrophenol, diffuses out of the fibers into the surrounding medium as shown in FIG. 2c (Type 1). The reaction rates of the enzyme attached (e.g., contained within) the microtubes are slightly reduced in comparison to the free enzyme. Without being bound by any theory, it is possible that the reaction rates are reduced because of the following reasons: (1) the substrate has to diffuse into the fibers in order to reach the active site of the enzyme; and/or (2) the enzyme has to diffuse outside; (3) the product has to diffuse outside in order to be detected; (4) some enzyme activity was lost during the spinning process itself. The attainment of maximum reaction velocity occurs more rapidly with Type 2 fibers, undoubtedly due to their highly porous character. Upon closer examination of the initial kinetics, it can be seen that Type 1 fibers, which do not contain PEG in the shell, exhibit a linear reaction rate that is much reduced (inset—FIG. 2b, marked by dark arrows) than Type 2 fibers (which include PEG in the shell polymer, and consequently, pores in the microtube shell). Without being bound by any theory, the initial low rate seems to result from the time required for the penetration of the substrate into the fibers since these fibers have a less porous morphology and are more hydrophobic. In the porous fibers (Type 2) the penetration of the substrate is barely hampered since the presence of PEG facilitates the wetting of the outer surface of the fibers and thereby allows the access of the aqueous substrate.

Altogether, these results demonstrate that enzymes attached to (e.g., encapsulated within) electrospun microtubes maintain their enzymatic activity.

Thus, the present technology overcomes both the problem of fiber dissolution and subsequent leaching of the enzyme and the exposure of the enzyme to harmful solvents.

Example 2

Electrospun Microtubes can Release Enzymes Attached Thereto

Experimental Results
Enzyme can be Leached Out of the Electrospun Microtubes—

In order to determined whether the substrate diffuses into the fibers or the enzyme diffuses out of the fibers, 3 specimens containing alkaline phosphatase (AP) were cut out from the non-woven mat and placed in buffer. The buffer from the first sample was taken immediately and assayed (initial rinse). For the second and third samples the buffer was taken and assayed after 24 hours and 72 hours, respectively. The first sample was tested in order to evaluate if any removable enzyme resides on the outer surface of the fibers after the spinning. The relative activity of the escaped enzyme in the buffers for the two types of fibers is presented in FIG. 3. The results clearly indicate that a significant fraction of the enzyme has leached out of the fibers within the first 24 hours. Hence it can be concluded that the reaction monitored for the mat (the electrospun microtubes) is a result of both in-fiber and out-fiber reactions. Interestingly however, for Type 1 fibers, which do not contain PEG in the shell, 82% of enzyme has diffused outside the fibers within 24 hours (compared to the mat). For Type 2 fibers, which are more hydrophilic due to PEG, the leaching of the enzyme is less although by no means negligible. The results also point out, as was already mentioned, that Type 2 fibers are the most active system and attains 55% of the activity of the free enzyme.

Alkaline Phosphatase can Migrate to the Outer Surface of the Microtubes During Electrospinning—

Moreover, it is clear that some enzyme is located on the outer surface of the fibers (i.e., attached to the microtube shell) and can immediately enter the surrounding buffer upon rinsing. The migration of the enzyme to the outer surface of the fibers during the spinning is more pronounced in Type 2 and is probably due to PEG which might serve as hydrophilic conduit for the enzyme. It has been already found (Reznik S N, et al., 2006) that in the core-shell process all charges immediately accumulate at the outer surface of the shell in the drop. Ions are preferentially subjected to this migration as the electric field is applied. In the present case, the protein, which is a charged molecule, can also migrate to the outer surface during electrospinning. This may explain the relatively large quantity of enzyme that is released by rinsing.

Altogether, these results demonstrate that type 2 fibers attain more enzymatic activity as compared to type 1 fibers. In addition, the enzyme within the type 2 fibers (which include PEG in the shell) is present in both the outer surface and the inner surface of the microtubes. Thus, these results demonstrate that the even though the enzyme is mixed with the core solution, it is capable of migrating into the outer surface of the shell during the electrospinning process.

Example 3

Electrospun Microtubes can Serve as Microreactors

Experimental Results

β-Galactosidase Remains within the Hollow Fiber Micro-Reactor—

The kinetics of the β-GAL reaction were determined as described hereinabove for AP and the results are presented in FIGS. 4a-b. Briefly, pieces of mat (eletrospun microtubes) were immersed in buffer for a quick rinse, 24 or 72 hours to determine if there is any leaching of the enzyme (FIG. 5, shown are results of Type 2 as an example). Two striking differences between the AP and β-GAL series were observed (FIG. 6): (i) the β-GAL reaction rate of the Type 1 mat is much slower relative to that found for AP, and the activity of AP in the type 1 mat is slower relative to that found for the activity of the free enzyme in the core solution (prior to electrospinning). In type 2, conversely, the activity of the β-GAL is higher than that of AP and the reaction velocity of the β-GAL enzyme is comparable to the free enzyme. This intense response of Type 2 is attributed to the high porosity of these fibers and their hydrophilic nature; (ii) the results shown in FIG. 5 for Type 2 fibers demonstrate that the β-GAL enzyme doesn't diffuse out of the fibers even after 72 hours even though Type 2 might be thought to be the more likely to allow the enzyme to escape. That is, the reaction takes place only within the fibers. Thus, for β-GAL, the hollow fibers act as a micro-reactor; the substrate which enters the "reactor" through the entire porous shell is cleaved by the encapsulated enzyme and the reaction product then diffuses out into the surrounding medium. Thus, without being bound by any theory it seems that the reduction in the reaction rate for Type 1 is related solely to the slow diffusion of the substrate into the fibers. The size of the enzyme seems to affect both the amount of enzyme that can migrate during the spinning to the outer surface of the fibers and its subsequent escape into the surrounding medium. In the case of β-GAL only a small amount of enzyme was detected in the rinsing buffer for Type 2 while for Type 1 no enzyme was detected at all (data not shown). As was argued before, in the fibers which do not contain PEG in the shell (Type 1) an additional moderate slope at the very beginning of the reaction can be observed (FIG. 4b-inset, marked by dark arrow) due to the relatively high hydrophobicity of the surface which hinders the access of the aqueous dissolved substrate.

Altogether, these results demonstrate that the Type 1 system results in lowered enzymatic activity, especially for large proteins such as β-GAL, which cannot diffuse through the shell pores. The fact that Type 1 fibers are hydrophobic and non-porous and thus inhibit the entrance of these substrates seems to make Type 1 fibers less efficacious for their use as flow-through reactors. This is in contrast to the remarkably efficient system obtained with Type 2 fibers.

The Enzymatic Reaction Occurs within Type I Microtubes (Hollow Fibers)—

Visual evidence that the enzymatic reaction occurs within the type 1 fibers was obtained by using a substrate in which one of the products is fluorescent. For both AP and 13-GAL enzymes the substrates used liberate 4-methyumbelliferone after hydrolysis which allows imaging by fluorescence microscopy. As is clearly seen in FIGS. 7a-b, the interior of the fibers is fluorescent while the surrounding medium is dark. Thus, these results clearly show that both enzymatic reactions (of AP and β-GAL), in fact, take place within the fibers. It is important to emphasize that, in contrast to the mat immersion experiments, this method is very sensitive and enables the detection of very small amounts of product which accumulates within a relatively short time. Indeed, these images were acquired within 1-2 minutes after the substrate was applied, a time scale which is larger than the characteristic time [about 10 seconds, as was calculated by the present inventors (Dror Y., et al., 2007)] of the diffusion through the micro-tubes wall. Hence, these results are not in contradiction to those of the mat immersion experiments in which the kinetics were followed over a much longer period during which both the product and the enzyme (in the AP case) can diffuse outside the fibers. In FIG. 7b short slugs (sections) of fluorescent liquid are observed. This phenomenon has been previously found in such fibers (Dror Y., et al., 2007).

The results shown in Examples 1-3 demonstrate the direct incorporation of enzymes into micro-tubes fabricated by co-electrospinning by introduction of the enzymes into the aqueous core solution of the microtube (e.g., PEO). The shell solution in this case was made of PCL dissolved in mixture of chloroform and DMF. The separation between the outer organic and inner aqueous phases was found to preserve enzyme activity during and after spinning when the electrospun fibers (mats) were subsequently placed in an aqueous environment.

Two types of micro-tubes were fabricated which differ in their shell morphology. Type 2 shells were produced by adding PEG to the shell solution. By using a mixture of PEG and PCL in the shell, pores were formed during the solidification process and this, in turn, directly affected the transfer of molecules into and out of the fibers. As a consequence, the more porous fibers (Type 2) exhibited higher rates of enzymatic reaction. In addition two enzymes differing in their molecular weight were incorporated: AP and β-GAL. The difference in the molecular weight between the enzymes was well reflected in the kinetics of the enzymatic reactions for both types of micro-tubes. While AP could diffuse outside the fibers, β-GAL remained in the fibers without any leaching of the enzyme and the progress of the reaction depended only on the arrival of the substrate from the surroundings. Thus, the AP fibers act as an enzyme release device in which the release rate can be tailored by modifying the morphology of the shell and, on the other hand, the β-GAL fibers act as an enzymatic micro-reactor with an efficient provision of the substrate through the entire surface area and efficient discharge of the product. Thus, by manipulating the morphology of the shell, the substrate supply and product release rate can be controlled. This method of encapsulation can be used when a separation between the enzyme and an external aqueous environment is desired (e.g. with living tissue to avoid immunological reactions). The remarkable retention of the enzyme activity for β-GAL Type 2 fibers clearly demonstrates that this approach preserves the activity of the enzyme.

Another advantage of the core-shell fiber method is the small volume within the micro-tubes which enables the quick buildup of the product. This is important for enzymes working in sequence where the local concentration of the product of the first reaction serves as the substrate for a subsequent reaction. In this regard, these nanotubes are somewhat analogous to living cells except that any manner of enzymes may be added to the fibers without regard to their biological origin. Another advantage of this system is that unlike living cells, there is no discrimination as to which type of small molecules may enter these tubes. For example, phosphorylated molecules (like p-nitrophenyl phosphate) which do not enter *Escherichia coli* cells can enter the microtubes described herein.

Example 4

Use of the Electrospun Microtubes as Microreactors for Chemical Transitions

The Microtubes of the Invention as Reactions for Multi-Step Enzymatic Processes—

In order to synthesize or catabolize molecules which require multi-step enzymatic processes the present inventors have devised electrospun microtubes which include the enzymes participating in the multi-step enzymatic process, attached thereto, as follows.

For a biochemical pathway which involves the conversion of A to E via compounds B, C and D, the second polymeric solution for forming the coat over the internal surface of the shell (also referred to as a core solution) is mixed with the following enzymes: the enzyme that converts the starting substrate A to intermediate compound B, the enzyme that converts B to C, the enzyme that converts C to D, and the enzyme that converts D to the end product E (see for example, FIG. 9). It should be noted that due to the proximity of the enzymes to each other in the microtube (which can be a closed micro-reactor), the local concentrations of each of the intermediate molecules, i.e., compounds B, C, and D is relatively high, which enables the kinetics of the reactions to occur, similarly to their concentrations in cells or cell compartments (e.g., mitochondria). The shell solution is made from hydrophobic polymers (water insoluble polymers), with or without the addition of PEG.

Thus, the microtube of the invention enables higher local concentrations of intermediate compounds which can not be reached from the same starting material (substrate A) if an open system (such as any solid substrate to which an enzyme is immobilized) is used.

The creation of micro- and nano-fibers containing enzymes simulates the cellular structure because two or more different enzymes involved in a particular synthesis or degradation can be put into proximity of one another. The interior of the tube is quite parallel to that of cells except that the borders of the tube are made from a water insoluble substance whereas living cells are encompassed by lipid membranes. In addition the microtubes are much longer than cells but quite similar in other dimensions to a bacterial cell. In the electrospun fibers, any small molecule can pass through the water insoluble barrier (pores can be made) regardless of its chemistry with the only provision that the small molecule be water soluble.

Thus, the present technology allows the entrapment of high concentrations of an enzyme or several enzymes within a confined space. Single or multi-step reactions can then take place where the product of one reaction is the substrate of a second and the second enzyme is spatially nearby. While such multi-step reactions can occur in an open system, the time necessary to reach the end product is orders of magnitude greater than within the microtube of the invention.

The Microtubes of the Invention can Include Enzymes from Different Species—

Another very important advantage of these electrospun fibers is that there is no limitation of which enzymes can be embedded. In nature, cells contain enzymes useful for their growth and reproduction. Organisms have not been designed or selected for industrial processes desired by humans. The microtubes of the invention allow any desired combination of enzymes to be brought together. This might mean that enzymes from totally different organisms (e.g. flies and humans) could be placed together for some use while in nature no organism exists with this combination.

The Microtubes of the Invention as Micro-Reactors for the Production of Molecules which are Intermediate Compounds of a Natural Process—

The enzymes encapsulated might be those carrying out part of pathway making the end product a substance that is usually an intermediate molecule in living organisms. This allows one to synthesize molecules that cannot be obtained in any amount from living material because the concentration of intermediates in cells is usually very low (in the order of 10 μM or less). For example, to synthesize indole-glycerol phosphate which is an intermediate in tryptophan synthesis within the cells of lower organisms, the enzymes that participate in the conversion of anthranilate (an inexpensive compound) to indole-glycerol phosphate should be included in the microtube, while the enzymes that continue the synthesis of tryptophan from indole-glycerol phosphate are excluded from the microtube. In summary, many combinations of enzymes from different organisms may be put together without any genetic engineering and partial sets of enzymes can also be used. The number of possible useful combinations is therefore very large.

Thus, the microtubes of the invention can be used as enzymatic micro-reactors where the inner space enables a confined but free reaction space. The substrate diffuses through the shell to the inner space where the enzymatic reaction takes place and the product can then diffuse out.

Example 5

The Electrospun Microtubes as Biosensors

Since the electrospun microtubes of the invention are insoluble in aqueous solutions, they can provide an excellent tool for the construction of biosensors.

Since any enzyme or combination of enzymes can be encapsulated in the electrospun microtubes, a variety of biosensors can be devised. For example, enzymes that are sensitive to heavy metals exhibit loss of activity in the presence of heavy metals. Another example, firefly luciferase, for example can be electrospun with its luciferin cofactor and any reaction affecting ATP production can be used in conjunction with light output the signal.

Example 6

The Electrospun Microtubes for Flow-Through Applications

Water Purification or Detoxification—

The electrospun microtubes of the invention, which are made of a water-insoluble outer shell, enable the flow of liquids. It will be appreciated that enzymes embedded in such microtubes can be used to purify the liquid flowing past the microtubes as molecules diffuse in and out of them.

Thus the present inventors have devised water purification or detoxification apparatuses, as follows. The second polymeric solution which forms the coat over the internal surface of the shell (also referred to as a core solution) [which is made of water-soluble polymer(s)] includes enzymes which remove a toxic moiety from water, such as the gene product of the atzA gene from *Pseudomonas* ADP that removes the chlorine from atrazine, a toxic substance. The shell solution [which is made of water-insoluble polymer(s)] is designed so as to enable water flow within the microtube. The effluent would thereby be rendered free of atrazine and safe for animal and human consumption.

Dialysis—

The microtubes of the invention can be used in various applications which remove certain compounds, such as dialysis procedures on humans. Thus, the electrospun microtubes can be made using a shell polymer which prevents the diffusion of enzymes therethrough, yet enables passage of water and substances that need to be purified. It will be appreciated that such microtubes can be also implanted into a subject in need thereof (e.g., a subject in need of dialysis), and due to the structure of a closed conduit, which prevents passage of embedded enzymes through the shell, there is no immune response to the implanted conduit.

Example 7

The Electrospun Microtubes for Enzyme Therapy

Since the electrospun microtubes of the invention are insoluble in aqueous solutions, they should provide excellent tool for the construction of material for enzyme therapy. Some individuals lack certain enzymes, usually as a result of their being homozygous for recessive alleles that lead to synthesis of an inactive enzyme. Gene therapy attempts to introduce the missing active gene which thereby leads to the production of an active enzyme. However, this technique is still quite inefficient. A different way of treating such patients is enzyme therapy, in which the missing enzyme is exogenously supplied to the subject. The main drawbacks of the second method is that injection of enzymes often leads to the formation of antibodies against them and the half-life of the enzymes within the body may be quite short.

Thus, the present inventors have devised an apparatus for enzyme therapy, as follows. Briefly, the electrospun microtubes which include a water-insoluble shell can include enzymes which are needed for enzyme therapy, and be further implanted in a subject in need thereof.

Enzyme Therapy for PKU—

Phenylketonuria (PKU) occurs in slightly less than 1 per 10000 individuals and is an autosomal recessive genetic disease caused by homozygosity of alleles encoding defective enzymes. Phenylalanine and tyrosine are amino acids that are found in most proteins. In humans, the source of these two amino acids is dietary protein. In normal individuals, excess phenylalanine is converted to tyrosine. Excess tyrosine, in turn, is broken down to fumarate and acetoacetate. Both tyrosine and phenylalanine are essential for human protein synthesis. In addition, tyrosine is the precursor of melanin (skin and eye pigment) and for certain hormone like substances such as thyroxine. Phenylketonuria is caused by the lack of the enzyme (phenylalanine 4-monooxygease EC 1.14.16.1) that converts phenylalanine to tyrosine. The result of this defect is the accumulation of phenylalanine in the blood along with a number of compounds that are derived from it (e.g. phenylpyruvic acid and phenyllacetic acid). The result is brain damage (and an IQ of 30-70) as some of these compounds are toxic. The current method of preventing deterioration of the disease is to limit the intake of phenylalanine. The present inventors have envisaged that PKU can be treated by implanting electrospun microtubes containing the missing enzyme, phenylalanine hydroxylase (PAH; GenBank Accession No. NP_00026), in a subject diagnosed with PKU, and thereby enabling the breakdown of excess phenylalanine in the subject. It will be appreciated that in this case, the microtube can be designed so as to enable release of enzyme from the inner surface through the outer shell (e.g., using PEG in the outer shell) or alternatively can be designed such that the enzyme is entrapped (or remains) within the microtubes and effects its activity there (e.g., by diffusion of the substrate or end-product through the shell pores, or microtube opening(s)). As phenylalanine hydroxylase can be phosphorylated (with a molecular weight of consists of 50,000 Da) or dephosphorylated (with a molecular weight of 49,000 Da), the size of the pores in the shell should enable passage (by diffusion) of each of these forms (e.g., about 5 nm in diameter). Microtubes can be made with smaller pores that will prevent the loss of the enzyme which will remain within the microtube.

Example 8

The Desorption Process

FIG. 8 schematically depicts the desorption of a molecule-of-interest to the microtube of the invention. After the electrospinning process, the molecule-of-interest (e.g., a protein, an enzyme) is adsorbed to the inner side of the microtubes. As mentioned, the porosity of the microtubes can be controlled (e.g., adding PEG to the shell polymer), therefore the shell consists of nanopores (see #3 in FIG. 8) with an opening to the outer surface of the microtube, which herein the pores are considered to have a cylindrical shape. When immersing the microtubes in a solution (e.g., a tissue culture medium, a physiological solution or any buffer) most nanopores opening are accessible to the solution.

Once the microtubes are immersed in the solution the nanopores are filled by the solution through capillary rise (see arrow #1 in FIG. 8). It will be appreciated that the time of the capillary rise depends on the solution rheological properties (viscosity and surface tension), the wetting angle and the geometry of the nanopore (length and radius). The solution penetrates to the microtube and start wetting and filling its entire inner volume. Desorption of the molecule-of-interest from the microtube wall depends mainly on the rate of the release of the molecule-of-interest from the polymer of the second polymeric solution. Finally, the molecule-of-interest (e.g., protein/enzymes) diffuses (see arrow #2 in FIG. 8) into the solution and released to the surroundings of the microtubes (assuming that the major release is through the microtubes envelope.

Note that the geometry (radius and length) of the nanopore is controllable, by adjusting the shell thickness, or by blending, more PEG to the shell polymer. Therefore, the release from or confinement in the microtube of the invention is controllable, e.g., in certain cases the molecule-of-interest is released from the microtube, whereas in other cases, the molecule-of-interest remains in the inner volume of the microtube. As shown in FIG. 2*a*, a molecule-of-interest is released from the microtube of the invention in a controlled manner, which can be extended beyond 2500, minutes, e.g., for several days and months.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

REFERENCES

Additional References are Cited in Text (1) Xie, J.; Hsieh, Y. L. J. Mater. Sci. 2003, 38, 2125-2133.

(2) Zhang, Y. Z.; Wang, X.; Lim, C. T.; Ramakrishna, S. Biomacromolecules 2006, 7, 1049-1057.

(3) Jiang, H.; Hu, Y.; Zhao, P.; Li, Y.; Zhu, K. J. Biomed. Mater. Res. Part B: Appl. Biomater. 2006, 79B, 50-57.

(4) Patel, A. C.; Li, S.; Yuan, J. M.; Wei, Y. Nano Letters 2006, 6, 1042-1046.

(5) Salalha, W.; Kuhn, J.; Dror, Y.; Zussman, E. Nanotechnology 2006, 17, 4675-4681.

(6) Sun, Z.; Zussman, E.; Yarin, A. L.; Wendorff, J. H.; Greiner, A. Adv. Mater. 2003, 15, 1929-1932.

(7) Ye, P.; Xu, Z. K.; Wu, J.; Innocent, C.; Seta, P. Macromolecules 2006, 39, 1041-1045.

(8) Jia, H.; Zhu, G.; Vugrinovich, B.; Kataphinan, W.; Reneker, D. H.; Wang, P. Biotechnol. Prog. 2002, 18, 1027-1032.

(9) Kim, T. G.; Park, T. G. Biotechnol. Prog. 2006, 22, 1108-1113.

(10) Huang, X. J.; Xu, Z. K.; Wan, L. S.; Innocent, C.; Seta, P. Macromol. Rapid Commun. 2006, 27, 1341-1345.

(11) Wu, L.; Yuan, X.; Sheng, J. J. Membr. Sci. 2005, 250, 167-173.

(12) Jiang, H.; Fang, D.; Hsiao, B. S.; Chu, B.; Chen, W. Biomacromolecules 2004, 4, 326-333.

(13) Zeng, J.; Aigner, A.; Czubayko, F.; Kissel, T.; Wendorff, J. H.; Greiner, A. Biomacromolecules 2005, 6, 1484-1488.

(14) Herricks, T. E.; Kim, S. H.; Kim, J.; Li, D.; Kwak, J. H.; Grate, J. W.; Kim, S. H.; Xia, Y. J. Mater. Chem. 2005, 15, 3241-3245.

(15) Dror, Y.; Salalha, W.; Avrahami, R.; Zussman, E.; Yarin, A. L.; Dersch, R.; Greiner, A.; Wendorff, J. H. 2007, Small 3:1064-73.

(16) Zabin, I.; Flower, A. V. b-Galactosidase, the Lactose Permease Protein and Thiogalactoside Transacetylase; in The Operon pp 89-121, Cold Spring Harbor Laboratory: NY, 1980.

(17) Zussman, E.; Yarin, A. L.; Bazilevsky, V.; Avrahami, R.; Feldman, M. Adv. Mater. 2006, 18, 348-353.

(18) Theron, A.; Zussman, E.; Yarin, A. L. Nanotechnology 2001, 12, 384.

(19) Coleman, M. M.; Graf, J. F.; Painter, P. C. Specific Interactions and the Miscibility of Polymer Blends; Technomic Publishing Company: Pennsylvania, 1991.

(20) Reznik, S, N.; Yarin, A. L.; Zussman, E.; Bercovici, L. Physics of Fluids 2006, 18, 1-13.

(21) D. H. Reneker, A. L. Yarin, E. Zussman, H. Xu, Advances in Applied Mechanics 2006, 40.

(22) S. Ramakrishna, K. Fujihara, W.-e. Teo, Lim, T. C., Z. Ma, An Introduction to Electrospinning and Nanofibers, 1 ed., World Scientific Publishing Company, 2005.

(23) D. Li, Y. N. Xia, Advanced Materials 2004, 16, 1151.

What is claimed is:

1. A microtube comprising:
   an electrospun shell,
   an electrospun coat polymer over an internal surface of said shell and a molecule-of-interest attached to the microtube,
   wherein said electrospun shell comprises pores,
   wherein said electrospun shell is formed of a first polymeric solution comprising a first solvent and said electrospun coat is formed of a second polymeric solution comprising a second solvent,
   wherein said second solvent of said second polymeric solution is incapable of dissolving the polymer of said first polymeric solution,
   wherein said first polymeric solution solidifies faster than said second polymeric solution,
   wherein said second polymeric solution is capable of wetting said internal surface of said shell during or following solidification of said first polymeric solution,
   wherein said electrospun shell comprises a polymer selected from the group consisting of poly (e-caprolactone) (PCL), polyamide, poly(siloxane), poly(silicone), poly(ethylene), poly(vinyl pyrrolidone), poly(2-hydroxy ethylmethacrylate), poly(N-vinyl pyrrolidone), poly(methyl methacrylate), poly(vinyl alcohol), poly (acrylic acid), poly(vinyl acetate), polyacrylamide, poly(ethylene-co-vinyl acetate), poly(methacrylic acid), polylactide, polyglycolide, poly(lactide-coglycolide), polyanhydride, polyorthoester, poly(carbonate), poly(acrylo nitrile), polyaniline, polyvinyl carbazole, polystyrene, poly(vinyl phenol), polyhydroxyacid, poly(caprolactone), polyanhydride, polyhydroxyalkanoate, and polyurethane, and whereas said electrospun coat comprises a polymer selected from the group consisting of poly(acrylic acid), poly(vinyl acetate), polyacrylamide, poly(ethylene-co-vinyl acetate), poly(ethylene glycol), poly(methacrylic acid), polylactide polyglycolide, poly(lactide-coglycolide), polyanhydride, polyorthoester, poly(carbonate), poly(ethylene oxide), polyaniline, polyvinyl carbazole, polystyrene, poly(vinyl phenol), and polyhydroxyacid,
   wherein said polymer of said first polymeric solution and said polymer of said second polymeric solution are different,
   wherein said molecule-of-interest is selected from the group consisting of: a polypeptide, a polynucleotide, a carbohydrate, a polysaccharide, a lipid, a drug molecule, and a small molecule, and
   wherein said small molecule is selected from the group consisting of a nucleotide base, an amino acid, a nucleotide, an antibiotic, and a vitamin.

2. The microtube of claim 1, wherein said first solvent of said first polymeric solution evaporates faster than said second solvent of said second polymeric solution.

3. The microtube of claim 1, wherein said second solvent of said second polymeric solution is capable of evaporating through said internal surface of said shell.

4. The microtube of claim 1, wherein a thickness of said shell is from about 100 nm to about 20 micrometer.

5. The microtube of claim 1, wherein an internal diameter of the microtube is from about 50 nm to about 20 micrometer.

6. The microtube of claim 1, wherein said first and said second polymeric solutions are selected from the group consisting of: 10% poly (e-caprolactone) (PCL) in chloroform ($CHCl_3$) and dimethylforamide (DMF) (80:20 by weight) as said first polymeric solution and 4% poly(ethylene oxide) (PEO) in water ($H_2O$) and ethanol (60:40 by weight) as said second polymeric solution, 10% PCL in $CHCl_3$ and DMF (80:20 by weight) as said first polymeric solution and 6% PEO in H₂O and ethanol (60:40 by weight) as said second polymeric solution, 9% PCL in CHCl₃ and DMF (90:10 by weight) as said first polymeric solution and 7% PEO in H₂O as said second polymeric solution, 10% PCL in CHCl₃ and DMF (80:20 by weight) as said first polymeric solution and 9% poly(vinyl alcohol) (PVA) in water and ethanol (50:50 by weight) as said second polymeric solution, and 10% PCL in CHCl₃ and DMF (90:10 by weight) as the first polymeric solution and 4% (by weight) PEO in ethanol:H₂O (26:74 by weight) as a second polymeric solution.

7. The microtube of claim 1, wherein said microtube is filled with a liquid.

8. The microtube of claim 1, wherein said molecule-of-interest is attached to said coat over said internal surface of said shell.

9. The microtube of claim 1, wherein said cell or said membrane-coated particle-of-interest is attached to said shell of the microtube.

10. The microtube of claim 1, wherein said first polymeric solution further comprises polyethylene glycol (PEG).

11. The microtube of claim 1, wherein said shell prevents diffusion of the molecule-of-interest therethrough.

12. A microfluidic device comprising a plurality of the microtubes of claim 1.

13. The microtube of claim 1, wherein said microtube is a single or separated microtube.

14. The microtube of claim 1, wherein said microtube comprises a plurality of microtubes.

15. The microtube of claim 14, wherein said plurality of microtubes form an aligned array.

16. The microtube of claim 7, wherein said liquid is blood.

17. The microtube of claim 1, wherein said polymer comprises a co-polymer.

18. The microtube of claim 1, wherein said polymer comprises a blend of polymers.

* * * * *